United States Patent
Hennequin

(10) Patent No.: US 6,887,874 B2
(45) Date of Patent: May 3, 2005

(54) CINNOLINE COMPOUNDS

(75) Inventor: Laurent Francois Andre Hennequin, Alderley Park (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/333,592

(22) PCT Filed: Aug. 7, 2001

(86) PCT No.: PCT/GB01/03533

§ 371 (c)(1), (2), (4) Date: Jan. 22, 2003

(87) PCT Pub. No.: WO02/12228

PCT Pub. Date: Feb. 14, 2002

(65) Prior Publication Data

US 2003/0212055 A1 Nov. 13, 2003

(30) Foreign Application Priority Data

Aug. 9, 2000 (EP) .............................................. 00402255

(51) Int. Cl.⁷ ..................... C07D 471/04; C07D 401/12; C07D 401/14; A61K 31/502; A61P 9/10
(52) U.S. Cl. ....................................... 514/248; 544/235
(58) Field of Search ........................... 544/235; 514/248

(56) References Cited

U.S. PATENT DOCUMENTS

| | | | |
|---|---|---|---|
| 5,646,153 A | 7/1997 | Spada et al. | |
| RE36,256 E | 7/1999 | Spada et al. | |
| 6,057,320 A | 5/2000 | Spada et al. | |
| 6,162,804 A | 12/2000 | Bilodeau et al. | |

FOREIGN PATENT DOCUMENTS

| | | |
|---|---|---|
| EP | 0326330 | 8/1989 |
| EP | 0 622 361 A | 11/1994 |
| WO | 87/04321 | 7/1987 |
| WO | 92/20642 | 11/1992 |
| WO | 98/14431 | 4/1998 |
| WO | 98/54093 | 12/1998 |
| WO | 99/21859 | 5/1999 |
| WO | 01/02369 | 1/2001 |

Primary Examiner—Richard L. Raymond
Assistant Examiner—Kahsay Habte
(74) Attorney, Agent, or Firm—Morgan, Lewis & Bockius LLP

(57) ABSTRACT

The invention relatest to compounds of the formula (I) wherein either any one of $G_1$, $G_2$, $G_3$, $G_4$ and $G_5$ is nitrogen and the other four are —CH—, or $G_1$, $G_2$, $G_3$, $G_4$ and $G_5$ are all —CH—; Z is —O—, —NH—, —S—, —$CH_2$— or a direct bond; Z is linked to any one of $G_1$, $G_2$, $G_3$ and $G_4$ which is a free carbon atom; n is an integer from 0 to 5; any of the substitutents $R^1$ may be attached at any free carbon atom of the indole, azaindole or indazole group; m is an integer from 0 to 3; $R^a$ represents hydrogen; $R^b$ represents hydrogen or another value as defined herein; $R^1$ represents hydrogen, oxo, hydroxy, halogeno, $C_{1-4}$alkyl, $C_{1-4}$alkoxy, $C_{1-4}$alkoxy, $C_{1-4}$-alkyl, amino$C_{1-4}$alkyl, $C_{1-3}$alkylamino $C_{1-4}$alkyl, di($C_{1-3}$alkyl)amino$C_{1-4}$alkyl, —$C_{1-5}$alkyl(ring B) wherein ring B is selected from azetidinyl, pyrrolidinyl, piperidinyl, piperazinyl, N-methylpiperazinly, N-ethylpiperazinyl, morpholino and thiomorpholino; $R^2$ represents hydrogen, hydroxy, halogeno, cyano, nitro, trifluoromethyl, $C_{1-3}$alkyl, $C_{1-3}$alkoxy, $C_{1-3}$aklylsulphanyl, —$NR^3R^4$ (wherein $R^3$ and $R^4$, which may be the same or different, each represents hydrogen or $C_{1-3}$alkyl), or $R^5X^1$— (wherein $R^5$ and $X^1$ are as defined herein) and salts thereof, processes for the preparation of such compounds, pharmaceutical compositions containing a compound of formula I or a pharmaceutically acceptable salt thereof as active ingredient and the use of a compound of formula I in the manufacture of medicament for the production of an anti-angiogenic and/or vascular permeability reducing effect in warm-blooded animals. The compounds of formula I and the pharmaceutically acceptable salts thereof inhibit the effects of VEGF, a property of value in the treatment of a number of disease states including cancer and rheumatoid arthritis.

15 Claims, No Drawings

CINNOLINE COMPOUNDS

The present invention relates to cinnoline derivatives, processes for their preparation, pharmaceutical compositions containing them as active ingredient, methods for the treatment of disease states associated with angiogenesis and/or increased vascular permeability, to their use as medicaments and to their use in the manufacture of medicaments for use in the production of antiangiogenic and/or vascular permeability reducing effects in warm-blooded animals such as humans.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacol. Sci. 16: 57–66; Folkman, 1995, Nature Medicine 1: 27–31). Alteration of vascular permeability is thought to play a role in both normal and pathological physiological processes (Cullinan-Bove et al, 1993, Endocrinology 133: 829–837; Senger et al, 1993, Cancer and Metastasis Reviews, 12: 303–324). Several polypeptides with in vitro endothelial cell growth promoting activity have been identified including, acidic and basic fibroblast growth factors (aFGF & bFGF) and vascular endothelial growth factor (VEGF). By virtue of the restricted expression of its receptors, the growth, factor activity of VEGF, in contrast to that of the FGFs, is relatively specific towards endothelial cells. Recent evidence indicates that VEGF is an important stimulator of both normal and pathological angiogenesis (Jakeman et al, 1993, Endocrinology, 133: 848–859; Kolch et al, 1995, Breast Cancer Research and Treatment, 36:139–155) and vascular permeability (Connolly et al, 1989, J. Biol. Chem. 264: 20017–20024). Antagonism of VEGF action by sequestration of VEGF with antibody can result in inhibition of tumour growth (Kim et al, 1993, Nature 362: 841–844). Basic FGF (bFGF) is a potent stimulator of angiogenesis (e.g. Hayek et al, 1987, Biochem. Biophys. Res. Commun. 147: 876–880) and raised levels of FGFs have been found in the serum (Fujimoto et al, 1991, Biochem. Biophys. Res. Commun. 180: 386–392) and urine (Nguyen et al, 1993, J. Natl. Cancer. Inst. 85: 241–242) of patients with cancer.

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity which leads to phosphorylation of tyrosine residues on both the receptor and other intracellular molecules. These changes in tyrosine phosphorylation initiate a signaling cascade leading to a variety of cellular responses. To date, at least nineteen distinct RTK subfamilies, defined by amino acid sequence homology, have been identified. One of these subfamilies is presently comprised by the fms-like tyrosine kinase receptor, Flt or Flt1, the kinase insert domain-containing receptor, KDR (also referred to as Flk-1), and another fms-like tyrosine kinase receptor, Flt4. Two of these related RTKs, Flt and KDR, have been shown to bind VEGF with high affinity (De Vries et al, 1992, Science 255: 989–991; Terman et al, 1992, Biochem. Biophys. Res. Commun. 1992, 187: 1579–1586). Binding of VEGF to these receptors expressed in heterologous cells has been associated with changes in the tyrosine phosphorylation status of cellular proteins and calcium fluxes.

The present invention is based on the discovery of compounds that surprisingly inhibit the effects of VEGF, a property of value in the treatment of disease states associated with angiogenesis and/or increased vascular permeability such as cancer, diabetes, psoriasis, rheumatoid arthritis, Kaposi's sarcoma, haemangioma, acute and chronic nephropathies, atheroma, arterial restenosis, autoimmune diseases, acute inflammation, excessive scar formation and adhesions, lymphoedema, endometriosis, dysfunctional uterine bleeding and ocular diseases with retinal vessel proliferation. Compounds of the present invention generally possess higher potency against VEGF receptor tyrosine kinase than against epidermal growth factor (EGF) receptor tyrosine kinase. Compounds of the invention which have been tested possess activity against VEGF receptor tyrosine kinase such that they may be used in an amount sufficient to inhibit VEGF receptor tyrosine kinase whilst demonstrating no significant activity against EGF receptor tyrosine kinase. Compounds of the present invention generally possess higher potency against VEGF receptor tyrosine kinase than against FGF R1 receptor tyrosine kinase. Compounds of the invention which have been tested possess activity against VEGF receptor tyrosine kinase such that they may be used in an amount sufficient to inhibit VEGF receptor tyrosine kinase whilst demonstrating no significant activity against FGF $R^1$ receptor tyrosine kinase.

According to one aspect of the present invention there is provided the use of a compound of the formula I:

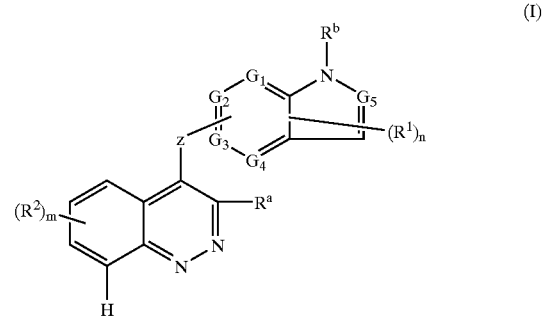

(I)

wherein:
either any one of $G_1$, $G_2$, $G_3$, $G_4$ and $G_5$ is nitrogen and the other four are —CH—, or $G_1$, $G_2$, $G_3$, $G_4$ and $G_5$ are all —CH—;
Z is —O—, —NH—, —S—, —CH$_2$— or a direct bond; Z is linked to any one of $G_1$, $G_2$, $G_3$ and $G_4$ which is a free carbon atom;
n is an integer from 0 to 5; any of the substitutents $R^1$ may be attached at any free carbon atom of the indole, azaindole or indazole group, such free carbon atoms may be $G_1$, $G_2$, $G_3$, $G_4$ or $G_5$ or may be at the 3-position of the indole, azaindole or indazole group;
m is an integer from 0 to 3;
$R^a$ represents hydrogen;
$R^b$ represents hydrogen, $C_{1-4}$alkyl, $C_{1-4}$alkoxyC$_{1-4}$alkyl, aminoC$_{1-4}$alkyl, $C_{1-3}$alkylaminoC$_{1-4}$alkyl, di($C_{1-3}$alkyl)aminoC$_{1-4}$alkyl, $C_{2-5}$alkenylaminoC$_{1-4}$alkyl, $C_{2-5}$alkynylaminoC$_{1-4}$alkyl, —C$_{1-5}$alkyl(ring A) wherein ring A is selected from azetidinyl, pyrrolidinyl, piperidinyl, piperazinyl, morpholino and thiomorpholino and wherein ring A may bear one or more substituents selected from $C_{1-4}$alkyl, $C_{2-5}$alkenyl, $C_{2-5}$alkynyl, hydroxy, oxo, halogeno, cyano, cyanoC$_{1-4}$alkyl, C$_{1-4}$alkylsulphonyl and C$_{1-4}$alkanoyl;

R$^1$ represents hydrogen, oxo, hydroxy, halogeno, C$_{1-4}$alkyl, C$_{1-4}$alkoxy, C$_{1-4}$alkoxyC$_{1-4}$alkyl, aminoC$_{1-4}$alkyl, C$_{1-3}$alkylaminoC$_{1-4}$alkyl, di(C$_{1-3}$alkyl)aminoC$_{1-4}$alkyl, —C$_{1-5}$alkyl(ring B) wherein ring B is selected from azetidinyl, pyrrolidinyl, piperidinyl, piperazinyl, N-methylpiperazinyl, N-ethylpiperazinyl, morpholino and thiomorpholino;

R$^2$ represents hydrogen, hydroxy, halogeno, cyano, nitro, trifluoromethyl, C$_{1-3}$alkyl, C$_{1-3}$alkoxy, C$_{1-3}$alkylsulphanyl, —NR$^3$R$^4$ (wherein R$^3$ and R$^4$, which may be the same or different, each represents hydrogen or C$_{1-3}$alkyl), or R$^5$X$^1$— (wherein X$^1$ represents a direct bond, —O—, —CH$_2$—, —OC(O)—, —C(O)—, —S—, —SO—, —SO$_2$—, —NR$^6$C(O)—, —C(O)NR$^7$—, —SO$_2$NR$^8$—, —NR$^9$SO$_2$— or —NR$^{10}$— (wherein R$^6$, R$^7$, R$^8$, R$^9$ and R$^{10}$ each independently represents hydrogen, C$_{1-3}$alkyl or C$_{1-3}$alkoxyC$_{2-3}$alkyl), and R$^5$ is selected from one of the following twenty-two groups:

1) hydrogen, oxiranylC$_{1-4}$alkyl or C$_{1-5}$alkyl which may be unsubstituted or which may be substituted with one or more groups selected from hydroxy, fluoro, chloro, bromo and amino;

2) C$_{1-5}$alkylX$^2$C(O)R$^{11}$ (wherein X$^2$ represents —O— or —NR$^{12}$— (in which R$^{12}$ represents hydrogen, C$_{1-3}$alkyl or C$_{1-3}$alkoxyC$_{2-3}$alkyl) and R$^{11}$ represents C$_{1-3}$alkyl, —N$^{13}$R$^{14}$ or —OR$^{15}$ (wherein R$^{13}$, R$^{14}$ and R$^{15}$ which may be the same or different each represents hydrogen, C$_{1-5}$alkyl or C$_{1-3}$alkoxyC$_{2-3}$alkyl));

3) C$_{1-5}$alkylX$^3$R$^{16}$ (wherein X$^3$ represents —O—, —S—, —SO—, —SO$_2$—, —OC(O)—, —NR$^{17}$C(O)—, —C(O)NR$^{18}$—, —SO$_2$NR$^{19}$—, —NR$^{20}$SO$_2$— or —NR$^{21}$— (wherein R$^{17}$, R$^{18}$, R$^{19}$, R$^{20}$ and R$^{21}$ each independently represents hydrogen, C$_{1-3}$alkyl or C$_{1-3}$alkoxyC$_{2-3}$alkyl) and R$^{16}$ represents hydrogen, C$_{1-3}$alkyl, cyclopentyl, cyclohexyl or a 4-, 5- or 6-membered saturated heterocyclic group with 1–2 heteroatoms, selected independently from O, S and N, which C$_{1-3}$alkyl group may bear 1 or 2 substituents selected from oxo, hydroxy, halogeno and C$_{1-4}$alkoxy and which cyclic group may bear 1 or 2 substituents selected from oxo, hydroxy, halogeno, cyano, C$_{1-4}$cyanoalkyl, C$_{1-4}$alkyl, C$_{1-4}$hydroxyalkyl, C$_{1-4}$alkoxy, C$_{1-4}$alkoxyC$_{1-4}$alkyl, C$_{1-4}$alkylsulphonylC$_{1-4}$alkyl, C$_{1-4}$alkoxycarbonyl, C$_{1-4}$aminoalkyl, C$_{1-4}$alkylamino, di(C$_{1-4}$alkyl)amino, C$_{1-4}$alkylaminoC$_{1-4}$alkyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy and a group —(—O—)$_f$(C$_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from C$_{1-4}$alkyl));

4) C$_{1-5}$alkylX$^4$C$_{1-5}$alkylX$^5$R$^{22}$ (wherein X$^4$ and X$^5$ which may be the same or different are each —O—, —S—, —SO—, —SO$_2$—, —NR$^{23}$C(O)—, —C(O)NR$^{24}$—, —SO$_2$NR$^{25}$, —NR$^{26}$SO$_2$— or —NR$^{27}$— (wherein R$^{23}$, R$^{24}$, R$^{25}$, R$^{26}$ and R$^{27}$ each independently represents hydrogen, C$_{1-3}$alkyl or C$_{1-3}$alkoxyC$_{2-3}$alkyl) and R$^{22}$ represents hydrogen, C$_{1-3}$alkyl or C$_{1-3}$alkoxyC$_{2-3}$alkyl);

5) R$^{28}$ (wherein R$^{28}$ is a 4-, 5- or 6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, cyano, C$_{1-4}$cyanoalkyl, C$_{1-4}$alkyl, C$_{1-4}$hydroxyalkyl, C$_{1-4}$alkoxy, C$_{1-4}$alkanoyl, C$_{1-4}$alkoxyC$_{1-4}$alkyl, C$_{1-4}$alkylsulphonyl, C$_{1-4}$akylsulphonylC$_{1-4}$alkyl, C$_{1-4}$alkoxycarbonyl, C$_{1-4}$aminoalkyl, C$_{1-4}$alkylamino, di(C$_{1-4}$alkyl)amino, C$_{1-4}$alkylaminoC$_{1-4}$alkyl, di(C$_{1-4}$alkyl)aminoC$_{1-4}$alkyl, C$_{1-4}$alkylaminoC$_{1-4}$alkoxy, di(C$_{1-4}$alkyl)amino C$_{1-4}$alkoxy and a group —(—O—)$_f$(C$_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from C$_{1-4}$alkyl));

6) C$_{1-5}$alkylR$^{28}$ (wherein R$^{28}$ is as defined hereinbefore);
7) C$_{2-5}$alkenylR$^{28}$ (wherein R$^{28}$ is as defined hereinbefore);
8) C$_{2-5}$alkenylR$^{28}$ (wherein R$^{28}$ is as defined hereinbefore);
9) R$^{29}$ (wherein R$^{29}$ represents a pyridone group, a phenyl group or a 5–6-membered aromatic heterocyclic group (linked via carbon or nitrogen) with 1–3 heteroatoms selected from O, N and S, which pyridone, phenyl or aromatic heterocyclic group may carry up to 5 substituents selected from hydroxy, halogeno, amino, C$_{1-4}$alkyl, C$_{1-4}$alkoxy, C$_{1-4}$hydroxyalkyl, C$_{1-4}$aminoalkyl, C$_{1-4}$alkylamino, C$_{1-4}$hydroxyalkoxy, carboxy, trifluoromethyl, cyano, —C(O)NR$^{30}$R$^{31}$, —NR$^{32}$C(O) R$^{33}$ (wherein R$^{30}$, R$^{31}$ R$^{32}$ and R$^{33}$, which may be the same or different, each represents hydrogen, C$_{1-4}$alkyl or C$_{1-3}$alkoxyC$_{2-3}$alkyl) and a group —(—O—)$_f$(C$_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from C$_{1-4}$alkyl));

10) C$_{1-5}$alkylR$^{29}$ (wherein R$^{29}$ is as defined hereinbefore);
11) C$_{2-5}$alkenylR$^{29}$ (wherein R$^{29}$ is as defined hereinbefore);
12) C$_{2-5}$akynylR$^{29}$ (wherein R$^{29}$ is as defined hereinbefore);
13) C$_{1-5}$alkylX$^6$ R$^{29}$ (wherein X$^6$ represents —O—, —S—, —SO$_2$—, —SO$_2$—, —NR$^{34}$C(O)—, —C(O)NR$^{35}$—, —SO$_2$NR$^{36}$, —NR$^{37}$SO$_2$— or —NR$^{38}$ — (wherein R$^{34}$, R$^{35}$, R$^{36}$, R$^{37}$ and R$^{38}$ each independently represents hydrogen, C$_{1-3}$alkyl or C$_{1-3}$alkoxyC$_{2-3}$alkyl) and R$^{29}$ is as defined hereinbefore);

14) C$_{2-5}$alkenylX$^7$R$^{29}$ (wherein X$^7$ represents —O—, —S—, —SO—, —SO$_2$—, —NR$^{39}$C(O)—, —C(O) N$^{40}$—, —SO$_2$NR$^{41}$—, —NR$^{42}$SO$_2$— or —NR$^{43}$— (wherein R$^{39}$, R$^{40}$, R$^{41}$, R$^{42}$ and R$^{43}$ each independently represents hydrogen, C$_{1-3}$alkyl or C$_{1-3}$alkoxyC$_{2-3}$alkyl) and R$^{29}$ is as defined hereinbefore);

15) C$_{2-5}$alkynylX$^8$R$^{29}$ (wherein X$^8$ represents —O—, —S—, —SO—, —SO$_2$—, —NR$^{44}$C(O)—, —C(O) NR$^{45}$—, SO$_2$N$^{46}$—, —NR$^{47}$SO$_2$— or —NR$^{48}$ — (wherein R$^{44}$, R$^{45}$, R$^{46}$, R$^{47}$ and R$^{48}$ each independently represents hydrogen, C$_{1-3}$alkyl or C$_{1-3}$alkoxyC$_{2-3}$alkyl) and R$^{29}$ is as defined hereinbefore);

16) C$_{1-4}$alkylX$^9$C$_{1-4}$alkylR$^{29}$ (wherein X$^9$ represents —O—, —S—, —SO$_2$—, —SO$_2$—, —NR$^{49}$C(O)—, —C(O) NR$^{50}$—, —SO$_2$NR$^{51}$—, —NR$^{52}$SO$_2$— or —NR$^{53}$— (wherein R$^{49}$, R$^{50}$, R$^{51}$, R$^{52}$ and R$^{53}$ each independently represents hydrogen, C$_{1-3}$alkyl or C$_{1-3}$alkoxyC$_{2-3}$alkyl) and R$^{29}$ is as defined hereinbefore);

17) C$_{1-4}$alkylX$^9$C$_{1-4}$alkylR$^{28}$ (wherein X$^9$ and R$^{28}$ are as defined hereinbefore);

18) C$_{2-5}$alkenyl which may be unsubstituted or which may be substituted with one or more groups selected from hydroxy, fluoro, amino, C$_{1-4}$alkylamino, N,N-di(C$_{1-4}$alkyl)amino, aminosulphonyl, N-C$_{1-4}$alkylaminosulphonyl and N,N-di(C$_{1-4}$alkyl) aminosulphonyl;

19) C$_{2-5}$alkynyl which may be unsubstituted or which may be substituted with one or more groups selected from hydroxy, fluoro, amino, $C_{1-4}$alkylamino, N,N-di($C_{1-4}$alkyl)amino, aminosulphonyl, N-$C_{1-4}$alkylaminosulphonyl and N,N-di($C_{1-4}$alkyl)aminosulphonyl;
20) $C_{2-5}$alkenylX$^9$C$_{1-4}$alkylR$^{28}$ (wherein X$^9$ and R$^{28}$ are as defined hereinbefore);
21) $C_{2-5}$alkynylX$^9$C$_{1-4}$alkylR$^{28}$ (wherein X$^9$ and R$^{28}$ are as defined hereinbefore); and
22) $C_{1-4}$alkylR$^{54}$(C$_{1-4}$alkyl)$_q$(X$^9$)$_r$R$^{55}$ (wherein X$^9$ is as defined hereinbefore, q is 0 or 1, r is 0 or 1, and R$^{54}$ and R$^{55}$ are each independently selected from hydrogen, $C_{1-3}$alkyl, cyclopentyl, cyclohexyl and a 4-, 5- or 6-membered saturated heterocyclic group with 1–2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxyC$_{1-4}$alkyl, $C_{1-4}$alkylsulphonylC$_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylaminoC$_{1-4}$alkyl, di($C_{1-4}$alkyl)aminoC$_{1-4}$alkyl, $C_{1-4}$alkylaminoC$_{1-4}$alkoxy, di($C_{1-4}$alkyl)aminoC$_{1-4}$alkoxy and a group —(—O—)$_f$ (C$_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from $C_{1-4}$alkyl), with the proviso that R$^{54}$ cannot be hydrogen);
and additionally wherein any $C_{1-5}$alkyl, $C_{2-5}$alkenyl or $C_{2-5}$alkynyl group in R$^5$X$^1$— may bear one or more substituents selected from hydroxy, halogeno and amino);
or a salt thereof, or a prodrug thereof for example an ester or an amide, in the manufacture of a medicament for use in the production of an antiangiogenic and/or vascular permeability reducing effect in warm-blooded animals such as humans.

According to another aspect of the present invention there is provided the use of a compound of the formula I$^1$:

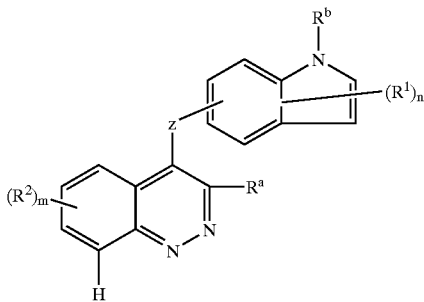

(I$^1$)

wherein:
Z is —O—, —NH—, —S—, —CH$_2$— or a direct bond; Z is linked to the benz ring of the indole group at any of the positions 4-, 5-, 6- or 7- of the indole group;
n is an integer from 0 to 5; any of the substituents R$^1$ maybe attached at any free carbon atom of the indole group, such free carbon atoms may be at positions 2-, 3-, 4-, 5-, 6-, or 7- of the indole group;
m is an integer from 0 to 3;
R$^a$ represents hydrogen;
R$^b$ represents hydrogen, $C_{1-4}$alkyl, $C_{1-4}$alkoxyC$_{1-4}$alkyl, aminoC$_{1-4}$alkyl, $C_{1-3}$alkylaminoC$_{1-4}$alkyl, di($C_{1-3}$alkyl)aminoC$_{1-4}$alkyl, —C$_{1-5}$alkyl(ring A) wherein ring A is selected from azetidinyl, pyrrolidinyl, piperidinyl, piperazinyl, N-methylpiperazinyl, N-ethylpiperazinyl, morpholino and thiomorpholino;
R$^1$ represents hydrogen, oxo, hydroxy, halogeno, $C_{1-4}$alkyl, $C_{1-4}$alkoxy, $C_{1-4}$alkoxyC$_{1-4}$alkyl, aminoC$_{1-4}$alkyl, $C_{1-3}$alkylaminoC$_{1-4}$alkyl, di($C_{1-3}$alkyl)aminoC$_{1-4}$alkyl, —C$_{1-5}$alkyl(ring B) wherein ring B is selected from azetidinyl, pyrrolidinyl, piperidinyl, piperazinyl, N-methylpiperazinyl, N-ethylpiperazinyl, morpholino and thiomorpholino;
R$^2$ represents hydrogen, hydroxy, halogeno, cyano, nitro, trifluoromethyl, $C_{1-3}$alkyl, $C_{1-3}$alkoxy, $C_{1-3}$alkylsulphanyl, —NR$^3$R$^4$ (wherein R$^3$ and R$^4$, which may be the same or different, each represents hydrogen or $C_{1-3}$alkyl), or R$^5$X$^1$— (wherein X$^1$ represents a direct bond, —O—, —CH$_2$—, —OC(O)—, —C(O)—, —S—, —SO—, —SO$_2$—, —NR$^6$C(O)—, —C(O)NR$^7$—, —SO$_2$NR$^7$—, —NR$^9$SO$_2$— or —NR$^{10}$ (wherein R$^6$, R$^7$, R$^8$, R$^9$ and R$^{10}$ each independently represents hydrogen, $C_{1-3}$alkyl or $C_{1-3}$alkoxyC$_{2-3}$alkyl), and R$^5$ is selected from one of the following twenty-two groups:
1) hydrogen, oxiranylC$_{1-4}$alkyl or $C_{1-5}$alkyl which maybe unsubstituted or which may be substituted with one or more groups selected from hydroxy, fluoro, chloro, bromo and amino;
2) $C_{1-5}$alkylX$^2$C(O)R$^{11}$ (wherein X$^2$ represents —O— or —NR$^{12}$— (in which R$^{12}$ represents hydrogen, $C_{1-3}$alkyl or $C_{1-3}$alkoxyC$_{2-3}$alkyl) and R$^{11}$ represents $C_{1-3}$alkyl, —NR$^{13}$R$^{14}$ or —OR$^{15}$ (wherein R$^{13}$, R$^{14}$ and R$^{15}$ which may be the same or different each represents hydrogen, $C_{1-5}$alkyl or $C_{1-3}$alkoxyC$_{2-3}$alkyl));
3) $C_{1-5}$alkylX$^3$R$^{16}$ (wherein X$^3$ represents —O—, —S—, —SO—, —SO$_2$—, —OC(O)—, —NR$^{17}$C(O)—, —C(O)NR$^{18}$—, —SO$_2$NR$^{19}$, —NR$^{20}$SO$_2$— or —N$^{21}$— (wherein R$^{17}$, R$^{18}$, R$^{19}$, R$^{20}$ and R$^{21}$ each independently represents hydrogen, $C_{1-3}$alkyl or $C_{1-3}$alkoxyC$_{2-3}$alkyl) and R$^{16}$ represents hydrogen, $C_{1-3}$alkyl, cyclopentyl, cyclohexyl or a 4-, 5- or 6-membered saturated heterocyclic group with 1–2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxyC$_{1-4}$alkyl, $C_{1-4}$alkylsulphonylC$_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylaminoC$_{1-4}$alkyl, di($C_{1-4}$alkyl)aminoC$_{1-4}$alkyl, $C_{1-4}$alkylaminoC$_{1-4}$alkoxy, di($C_{1-4}$alkyl)aminoC$_{1-4}$alkoxy and a group —(—O—)$_f$ (C$_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from $C_{1-4}$alkyl));
4) $C_{1-5}$alkylX$^4$C$_{1-5}$alkylX$^5$R$^{22}$ (wherein X$^4$ and X$^5$ which may be the same or different are each —O—, —S—, —SO—, —SO$_2$—, —NR$^{23}$C(O)—, —C(O)NR$^{24}$, —SO$_2$NR$^{25}$—, —NR$^{26}$SO$_2$— or —NR$^{27}$— (wherein R$^{23}$, R$^{24}$, R$^{25}$, R$^{26}$ and R$^{27}$ each independently represents hydrogen, $C_{1-3}$alkyl or $C_{1-3}$alkoxyC$_{2-3}$alkyl) and R$^{22}$ represents hydrogen, $C_{1-3}$alkyl or $C_{1-3}$alkoxyC$_{2-3}$alkyl);
5) R$^{28}$ (wherein R$^{28}$ is a 4-, 5- or 6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from $C_{1-4}$alkyl));

6) $C_{1-5}$alkyl$R^{28}$ (wherein $R^{28}$ is as defined hereinbefore);
7) $C_{2-5}$alkenyl$R^{28}$ (wherein $R^{28}$ is as defined hereinbefore);
8) $C_{2-5}$alkynyl$R^{28}$ (wherein $R^{28}$ is as defined hereinbefore);
9) $R^{29}$ (wherein $R^{29}$ represents a pyridone group, a phenyl group or a 5–6-membered aromatic heterocyclic group (linked via carbon or nitrogen) with 1–3 heteroatoms selected from O, N and S, which pyridone, phenyl or aromatic heterocyclic group may carry up to 5 substituents selected from hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —C(O)NR$^{30}$R$^{31}$, NR$^{32}$C(O)R$^{33}$ (wherein $R^{30}$, $R^{31}$, $R^{32}$ and $R^{33}$, which may be the same or different, each represents hydrogen, $C_{1-4}$alkyl or $C_{1-3}$alkoxy$C_{2-3}$alkyl) and a group —(—O—)$_f$($C_{1-4}$alkyl)$_g$ringD (wherein f is 0 or 1, is 0 or 1 and ring D is a 4-, 5- or 6-membered saturated heterocyclic group with 1–2 heteroatoms, selected independently from O, S and N, which cyclic group may bear one or more substituents selected from $C_{1-4}$alkyl));
10) $C_{1-5}$alkyl$R^{29}$ (wherein $R^{29}$ is as defined hereinbefore);
11) $C_{2-5}$alkenyl$R^{29}$ (wherein $R^{29}$ is as defined hereinbefore);
12) $C_{2-5}$alkynyl$R^{29}$ (wherein $R^{29}$ is as defined hereinbefore);
13) $C_{1-5}$alkyl$X^6R^{29}$ (wherein $X^6$ represents —O—, —S—, —SO—, —SO$_2$—, —N$^{34}$C(O)—, —C(O)NR$^{35}$—, SO$_2$NR$^{36}$—, —NR$^{37}$SO$_2$— or —NR$^{38}$— (wherein $R^{34}$, $R^{35}$, $R^{36}$, $R^{37}$ and $R^{38}$ each independently represents hydrogen, $C_{1-3}$alkyl or $C_{1-3}$alkoxy$C_{2-3}$alkyl) and $R^{29}$ is as defined hereinbefore);
14) $C_{2-5}$alkenyl$X^7R^{29}$ (wherein $X^7$ represents —O—, —S—, —SO—, —SO$_2$—, —NR$^{39}$C(O)—, —C(O)NR$^{40}$—, —SO$_2$NR$^{41}$—, —NR$^{42}$SO$_2$— or —NR$^{43}$— (wherein $R^{39}$, $R^{40}$, $R^{41}$, $R^{42}$ and $R^{43}$ each independently represents hydrogen, $C_{1-3}$alkyl or $C_{1-3}$alkoxy$C_{2-3}$alkyl) and $R^{29}$ is as defined hereinbefore);
15) $C_{2-5}$alkynyl$X^8R^{29}$ (wherein $X^8$ represents —O—, —S—, —SO—, —SO$_2$—, —NR$^{44}$C(O)—, —C(O)N$^{45}$—, —SO$_2$NR$^{46}$—, —NR$^{47}$SO$_2$— or —NR$^{48}$— (wherein $R^{44}$, $R^{45}$, $R^{46}$, $R^{47}$ and $R^{48}$ each independently represents hydrogen, $C_{1-3}$alkyl or $C_{1-3}$alkoxy$C_{2-3}$alkyl) and $R^{29}$ is as defined hereinbefore);
16) $C_{1-4}$alkyl$X^9C_{1-4}$alkyl$R^{29}$ (wherein $X^9$ represents —O—, —S—, —SO—, —SO$_2$—, —NR$^{49}$C(O)—, —C(O)NR$^{50}$—, —SO$_2$NR$^{51}$—, —NR$^{52}$SO$_2$— or —NR$^{53}$— (wherein $R^{49}$, $R^{50}$, $R^{51}$, $R^{52}$ and $R^{53}$ each independently represents hydrogen, $C_{1-3}$alkyl or $C_{1-3}$alkoxy$C_{2-3}$alkyl) and $R^{29}$ is as defined hereinbefore);
17) $C_{1-4}$alkyl$X^9C_{1-4}$alkyl$R^{28}$ (wherein $X^9$ and $R^{28}$ are as defined hereinbefore);
18) $C_{2-5}$alkenyl which may be unsubstituted or which may be substituted with one or more groups selected from hydroxy, fluoro, amino, $C_{1-4}$alkylamino, N,N-di($C_{1-4}$alkyl)amino, aminosulphonyl, N-$C_{1-4}$alkylaminosulphonyl and N,N-di($C_{1-4}$alkyl) aminosulphonyl;
19) $C_{2-5}$alkynyl which may be unsubstituted or which may be substituted with one or more groups selected from hydroxy, fluoro, amino, $C_{1-4}$alkylamino, N,N-di($C_{1-4}$alkyl)amino, aminosulphonyl, N-$C_{1-4}$alkylaminosulphonyl and N,N-di($C_{1-4}$alkyl) aminosulphonyl;
20) $C_{2-5}$alkenyl$X^9C_{1-4}$alkyl$R^{28}$ (wherein $X^9$ and $R^{28}$ are as defined hereinbefore);
21) $C_{2-5}$alkynyl$X^9C_{1-4}$alkyl$R^{28}$ (wherein $X^9$ and $R^{28}$ are as defined hereinbefore); and
22) $C_{1-4}$alkyl$R^{54}(C_{1-4}$alkyl)$_q(X^9)_rR^{55}$ (wherein $X^9$ is as defined hereinbefore, q is 0 or 1, r is 0 or 1, and $R^{54}$ and $R^{55}$ are each independently selected from hydrogen, $C_{1-3}$alkyl, cyclopentyl, cyclohexyl and a 4-, 5- or 6-membered saturated heterocyclic group with 1–2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy $C_{1-4}$alkyl, $C_{1-4}$alkylsulphonyl$C_{1-4}$alkyl, $C_{1-4}$alkoxycarbonyl, $C_4$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from $C_{1-4}$alkyl), with the proviso that $R^{54}$ cannot be hydrogen);

and additionally wherein any $C_{1-5}$alkyl, $C_{2-5}$alkenyl or $C_{2-5}$alkynyl group in $R^5X^1$— may bear one or more substituents selected from hydroxy, halogeno and amino);

or a salt thereof, or a prodrug thereof for example an ester or an amide, in the manufacture of a medicament for use in the production of an antiangiogenic and/or vascular permeability reducing effect in warm-blooded animals such as humans.

Preferably Z is —O—, —NH—, —S— or a direct bond.
More preferably Z is —O—, —NH— or —S—.
Particularly Z is —O— or —NH—, especially —O—.
Preferably Z is linked to the indole, azaindole or indazole group at the 5- or 6-positions of the indole, azaindole or indazole group.
More preferably Z is linked to the indole, azaindole or indazole group at the 5-position of the indole, azaindole or indazole group.
Preferably Z is linked to an indole group at the 5- or 6-positions of the indole group.
More preferably Z is linked to an indole group at the 5-position of the indole group.

Preferably $R^b$ represents hydrogen, $C_{1-2}$alkyl, $C_{2-3}$alkenylamino$C_{2-3}$alkyl, $C_{2-3}$alkynylamino$C_{2-3}$alkyl or —$C_{2-4}$alkyl(ring A) wherein ring A is selected from piperidinyl and piperazinyl and wherein ring A may bear one or more substituents selected from $C_{1-2}$alkyl, $C_{2-3}$alkenyl, $C_{2-3}$alkynyl, hydroxy, cyano, cyano$C_{1-2}$alkyl, $C_{1-2}$alkylsulphonyl and $C_{1-2}$alkanoyl.

More preferably $R^b$ represents hydrogen, methyl, $C_{2-3}$alkenylamino$C_{2-3}$alkyl, $C_{2-3}$alkynylamino$C_{2-3}$alkyl or —$C_{2-3}$alkyl(ring A) wherein ring A is selected from 4-acetylpiperazin-1-yl, 4-methylsulphonylpiperazin-1-yl, 4-cyanopiperazin-1-yl, 4-cyanomethylpiperazin-1-yl, 4-(prop-2-en-1-yl)piperazin-1-yl, 4-(prop-2-yn-1-yl)piperazin-1-yl and 4-hydroxypiperidino.

Particularly $R^b$ is hydrogen or methyl, especially hydrogen.

Advantageously R¹ represents hydrogen, oxo, hydroxy, halogeno, $C_{1-4}$alkyl, $C_{1-4}$alkoxy, $C_{1-4}$alkoxy$C_{1-4}$alkyl, amino$C_{1-4}$alkyl, $C_{1-3}$alkylamino$C_{1-4}$alkyl, di($C_{1-3}$alkyl)amino$C_{1-4}$alkyl, —$C_{1-5}$alkyl(ring B) wherein ring B is selected from azetidin-1-yl, pyrrolidin-1-yl, piperidin-1-yl, piperazin-1-yl, N-methylpiperazin-1-yl, N-ethylpiperazin-1-yl, morpholino and thiomorpholino.

Particularly R¹ represents methyl, ethyl, trifluoromethyl or halogeno.

Especially R¹ represents methyl, fluoro, chloro or bromo, more especially methyl or fluoro.

Preferably n is an integer from 0 to 3.

More preferably n is 0, 1 or 2.

According to one aspect of the present invention $G_1$ is nitrogen and $G_2$, $G_3$, $G_4$ and $G_5$ are —CH— forming an azaindole moiety which may bear one or more substituents R¹ as defined hereinbefore.

According to another aspect of the present invention $G_5$ is nitrogen and $G_1$, $G_2$, $G_3$ and $G_4$ are —CH— forming an indazole moiety which may bear one or more substituents R¹ as defined hereinbefore.

According to another aspect of the present invention $G_1$, $G_2$, $G_3$, $G_4$ and $G_5$ are all —CH— forming an indole moiety which may bear one or more substituents R¹ as defined hereinbefore.

In one embodiment of the invention the optionally substituted indole, azaindole or indazole moiety of formula II:

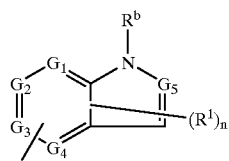

(II)

wherein R¹, $R^b$, $G_1$, $G_2$, $G_3$, $G_4$ and $G_5$ and n are as defined hereinbefore; is selected from the indole moieties:
4-fluoro-2-methylindol-5-yl, 2-methylindol-5-yl, 2-methylindol-6-yl, 2,3-dimethylindol-5-yl, 1-methylindol-5-yl, 1,2-dimethylindol-5-yl, 4-fluoroindol-5-yl, 6-fluoroindol-5-yl and indol-5-yl,
the azaindole moieties:

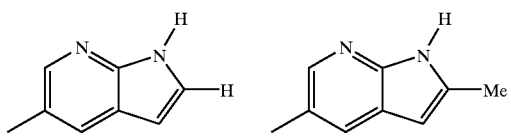

1H-pyrrolo[2,3-b]pyridin-5-yl and 2-methyl-1H-pyrrolo[2,3-b]pyridin-5-yl,
and the indazole moiety:

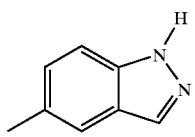

1H-indazol-5-yl.

The indole moieties are preferred over the azaindole and indazole moieties.

In another embodiment of the invention the optionally substituted indole moiety of formula II¹:

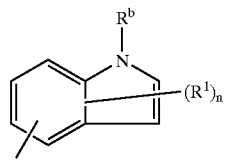

(II¹)

wherein R¹, $R^b$ and n are as defined hereinbefore;
is selected from 4-fluoro-2-methylindol-5-yl, 2-methylindol-5-yl, 2-methylindol-6-yl, 2,3-dimethylindol-5-yl, 1-methylindol-5-yl, 1,2-dimethylindol-5-yl, 4-fluoroindol-5-yl, 6-fluoroindol-5-yl and indol-5-yl.

Particularly the optionally substituted indole moiety of formula II¹ is selected from 4-fluoro-2-methylindol-5-yl, 4-fluoroindol-5-yl and 6-fluoroindol-5-yl, more especially from 4-fluoro-2-methylindol-5-yl.

Preferably m is an integer from 0 to 2, more preferably 1 or 2, most preferably 2.

Advantageously $X^1$ represents a direct bond, —O—, —S—, —NR⁶C(O)—, —NR⁹SO₂— or —NR¹⁰— (wherein R⁶, R⁹ and R¹⁰ each independently represents hydrogen, $C_{1-2}$alkyl or $C_{1-2}$alkoxyethyl).

Preferably $X^1$ represents a direct bond, —O—, —S—, —NR⁶C(O)—, —NR⁹SO₂— (wherein R⁶ and R⁹ each independently represents hydrogen or $C_{1-2}$alkyl) or NH.

More preferably $X^1$ represents —O—, —S—, —NR⁶C(O)— (wherein R⁶ represents hydrogen or $C_{1-2}$alkyl) or NH.

Particularly $X^1$ represents —O— or —NR⁶C(O)— (wherein R⁶ represents hydrogen or $C_{1-2}$alkyl), more particularly —O— or —NHC(O)—, especially —O—.

According to another aspect of the present invention $X^1$ represents —O— or a direct bond.

Advantageously $X^2$ represents —O— or —NR¹² (wherein R¹² represents hydrogen, $C_{1-3}$alkyl or $C_{1-2}$alkoxyethyl).

Advantageously $X^3$ represents —O—, —S—, —SO—, —SO₂—, —NR¹⁷C(O)—, —NR²⁰SO₂— or —NR²¹— (wherein R⁷, R²⁰ and R²¹ each independently represents hydrogen, $C_{1-2}$alkyl or $C_{1-2}$alkoxyethyl).

Preferably $X^3$ represents —O—, —S—, —SO—, —SO₂— or —N²¹— (wherein R²¹ represents hydrogen, $C_{1-2}$alkyl or $C_{1-2}$alkoxyethyl).

More preferably $X^3$ represents —O— or —NR²¹— (wherein R²¹ represents hydrogen or $C_{1-2}$alkyl).

According to another aspect of the present invention $X^3$ represents —O—, —SO₂—, —NR²⁰SO₂— or —NR²¹— (wherein R²⁰ and R²¹ each independently represents hydrogen, $C_{1-2}$alkyl or $C_{1-2}$alkoxyethyl).

Advantageously $X^4$ and $X^5$ which may be the same or different each represents —O—, —S—, —SO—, —SO₂— or —NR²⁷— (wherein R²⁷ represents hydrogen, $C_{1-3}$alkyl or $C_{1-2}$alkoxyethyl).

Preferably $X^4$ and $X^5$ which may be the same or different each represents —O—, —S— or —NR²⁷— (wherein R²⁷ represents hydrogen, $C_{1-2}$alkyl or $C_{1-2}$alkoxyethyl).

More preferably $X^4$ and $X^5$ which may be the same or different each represents —O— or —NH—.

Especially $X^4$ and $X^5$ each represents —O—.

Advantageously $X^6$ represents —O—, —S— or —NR³⁸— (wherein R³⁸ represents hydrogen, $C_{1-2}$alkyl or $C_{1-2}$alkoxyethyl).

Preferably $X^6$ represents —O— or —NR³⁸— (wherein R³⁸ represents hydrogen or $C_{1-2}$alkyl).

Especially $X^6$ represents —O—.

Advantageously $X^7$ represents —O—, —S— or —NR⁴³— (wherein R⁴³ represents hydrogen, $C_{1-2}$alkyl or $C_{1-2}$alkoxyethyl).

Preferably $X^7$ represents —O— or —NR$^{43}$— (wherein $R^{43}$ represents hydrogen, $C_{1-2}$alkyl).

Advantageously $X^8$ represents —O—, —S— or —NR$^{48}$— (wherein $R^{48}$ represents hydrogen, $C_{1-2}$alkyl or $C_{1-2}$alkoxyethyl).

Preferably $X^8$ represents —O— or —NR$^{48}$— (wherein $R^{48}$ represents hydrogen or $C_{1-2}$alkyl).

Advantageously $X^9$ represents —O— or —NR$^{53}$— (wherein $R^{53}$ represents hydrogen, $C_{1-2}$alkyl or $C_{1-2}$alkoxyethyl).

Preferably $X^9$ represents —O— or —NR$^{53}$— (wherein $R^{53}$ represents hydrogen or $C_{1-2}$alkyl).

Accordingly to another aspect of the present invention $X^9$ represents —O—, —CONR$^{50}$— or —NR$^{53}$— (wherein $R^{50}$ and $R^{53}$ each independently represents hydrogen or $C_{1-2}$alkyl).

Conveniently $R^{28}$ is pyrrolidinyl, piperazinyl, piperidinyl, imidazolidinyl, azetidinyl, morpholino or thiomorpholino which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$; alkyl, $C_{1-2}$alkylsulphonyl$C_{1-3}$alkyl, $C_{1-3}$alkoxycarbonyl, $C_{1-3}$alkylamino, di($C_{1-3}$alkyl)amino, $C_{1-3}$alkylamino $C_{1-3}$alkyl, di($C_{1-3}$alkyl)amino$C_{1-3}$alkyl, $C_{1-3}$alkylamino $C_{1-3}$alkoxy, di($C_{1-3}$alkyl)amino$C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, azetidinyl, morpholino and thiomorpholino, which cyclic group may bear one or more substituents selected from $C_{1-3}$alkyl).

Advantageously $R^{28}$ is pyrrolidinyl, piperazinyl, piperidinyl, azetidinyl, morpholino or thiomorpholino which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl, $C_{1-2}$alkylsulphonyl$C_{1-3}$alkyl, $C_{1-3}$alkoxycarbonyl, $C_{1-3}$alkylamino, di($C_{1-3}$alkyl)amino, $C_{1-3}$alkylamino $C_{1-3}$alkyl, di($C_{1-3}$alkyl)amino$C_{1-3}$alkyl, $C_{1-3}$alkylamino $C_{1-3}$alkoxy, di($C_{1-3}$alkyl)amino$C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino).

In one embodiment of the present invention $R^{28}$ is pyrrolidinyl, piperazinyl, piperidinyl, azetidinyl, morpholino or thiomorpholino which group may bear 1 or 2 substituents selected from a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino).

Particularly $R^{28}$ is pyrrolidinyl, piperazinyl, piperidinyl, azetidinyl, morpholino or thiomorpholino which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl and $C_{1-2}$alkylsulphonyl$C_{1-3}$alkyl.

According to another aspect of the present invention, preferably $R^{28}$ is pyrrolidinyl, piperazinyl, piperidinyl, morpholino or thiomorpholino which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl and $C_{1-2}$alkylsulphonyl$C_{1-3}$alkyl.

Where $R^{29}$ is a 5–6-membered aromatic heterocyclic group; it preferably has 1 or 2 heteroatoms, selected from O, N and S, of which more preferably one is N, and may be substituted as hereinbefore defined.

$R^{29}$ is particularly a pyridone, phenyl, pyridyl, imidazolyl, thiazolyl, thienyl, triazolyl or pyridazinyl group which group may be substituted as hereinbefore defined, more particularly a pyridone, pyridyl, imidazolyl, thiazolyl or triazolyl group, especially a pyridone, pyridyl, imidazolyl or triazolyl group which group may be substituted as hereinbefore defined.

In one embodiment of the invention $R^{29}$ represents a pyridone, phenyl or 5–6-membered aromatic heterocyclic group with 1 to 3 heteroatoms selected from O, N and S, which group may preferably carry up to 2 substituents, more preferably up to one substituent, selected from the group of substituents as hereinbefore defined.

In the definition of $R^{29}$, conveniently substituents are selected from halogeno, $C_{1-4}$alkyl, $C_{1-4}$alkoxy, cyano and a group —(—O—)$_f$($C_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, azetidinyl, morpholino and thiomorpholino, which cyclic group may bear one or more substituents selected from $C_{1-3}$alkyl).

In the definition of $R^{29}$, more conveniently substituents are selected from chloro, fluoro, methyl, ethyl and a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino).

According to another embodiment of the present invention in the definition of $R^{29}$, conveniently substituents are selected from halogeno, $C_{1-4}$alkyl, $C_{1-4}$alkoxy and cyano, more conveniently substituents are selected from chloro, fluoro, methyl and ethyl.

Advantageously $R^{54}$ and $R^{55}$ are each independently a 4-, 5- or 6-membered saturated heterocyclic group with 1–2 heteroatoms, selected independently from O, S and N, which cyclic group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl, $C_{1-2}$alkylsulphonyl$C_{1-3}$alkyl, $C_{1-3}$alkoxycarbonyl and a group —(—O—)$_f$($C_{1-3}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from $C_{1-3}$alkyl).

Preferably $R^{54}$ and $R^{55}$ are each selected from pyrrolidinyl, piperazinyl, piperidinyl, imidazolidinyl, azetidinyl, morpholino and thiomorpholino which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl , $C_{1-2}$alkylsulphonyl$C_{1-3}$alkyl, $C_{1-3}$alkoxycarbonyl and a group —(—O—)$_f$($C_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, azetidinyl, morpholino and thiomorpholino, which cyclic group may bear one or more substituents selected from $C_{1-3}$alkyl).

More preferably $R^{54}$ and $R^{55}$ are each selected from pyrrolidinyl, piperazinyl, piperidinyl, azetidinyl, morpholino and thiomorpholino which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl, $C_{1-2}$alkylsulphonyl$C_{1-3}$alkyl, $C_{1-3}$alkoxycarbonyl and a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino).

Particularly $R^{54}$ and $R^{55}$ are each selected from pyrrolidinyl, piperazinyl, piperidinyl, azetidinyl, morpholino and thiomorpholino which group may bear 1 or 2 substituents selected from a group —(—O—)$_f$(C$_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino).

More particularly $R^{54}$ and $R^{55}$ are each selected from pyrrolidinyl, piperazinyl, piperidinyl, azetidinyl, morpholino and thiomorpholino which group is unsubstituted.

Conveniently $R^2$ represents hydroxy, halogeno, cyano, nitro, trifluoromethyl, $C_{1-3}$alkyl, amino or $R^5X^1$— [wherein $X^1$ is as hereinbefore defined and $R^5$ is selected from one of the following twenty-two groups:

1) oxiranylC$_{1-4}$alkyl or C$_{1-5}$alkyl which may be unsubstituted or which may be substituted with one or more groups selected from fluoro, chloro and bromo, or C$_{2-5}$alkyl which may be unsubstituted or substituted with one or more groups selected from hydroxy and amino;
2) C$_{2-3}$alkylX$^2$C(O)R$^{11}$ (wherein X$^2$ is as hereinbefore defined and R$^{11}$ represents C$_{1-3}$alkyl, —NR$^{13}$R$^{14}$ or —OR$^{15}$ (wherein R$^{13}$, R$^{14}$ and R$^{15}$ which may be the same or different are each C$_{1-4}$alkyl or C$_{1-2}$alkoxyethyl));
3) C$_{2-4}$alkylX$^3$R$^{16}$ (wherein X$^3$ is as hereinbefore defined and R$^{16}$ represents hydrogen, C$_{1-3}$alkyl, cyclopentyl, cyclohexyl or a 4-, 5- or 6-membered saturated heterocyclic group with 1–2 heteroatoms, selected independently from O, S and N, which C$_{1-3}$alkyl group may bear 1 or 2 substituents selected from oxo, hydroxy, halogeno and C$_{1-3}$alkoxy and which cyclic group may bear 1 or 2 substituents selected from oxo, hydroxy, halogeno, cyano, C$_{1-4}$cyanoalkyl, C$_{1-4}$alkyl, C$_{1-4}$hydroxyalkyl, C$_{1-4}$alkoxy, C$_{1-4}$alkoxyC$_{1-4}$alkyl, C$_{1-4}$alkylsulphonylC$_{1-4}$alkyl, C$_{1-4}$alkoxycarbonyl, C$_{1-4}$alkylamino, di(C$_{1-4}$alkyl)amino, C$_{1-4}$alkylaminoC$_{1-4}$alkyl, di(C$_{1-4}$alkylaminoC$_{1-4}$alkyl, C$_{1-4}$alkylaminoC$_{1-4}$alkoxy, di(C$_{1-4}$alkyl)amino C$_{1-4}$alkoxy and a group —(—O—)$_f$(C$_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from C$_{1-4}$alkyl));
4) C$_{2-3}$alkylX$^4$C$_{2-3}$alkylX$^5$R$^{22}$ (wherein X$^4$ and X$^5$ are as hereinbefore defined and R$^{22}$ represents hydrogen or C$_{1-3}$alkyl);
5) R$^{28}$ (wherein R$^{28}$ is as defined hereinbefore);
6) C$_{1-5}$alkylR$^{56}$ (wherein R$^{56}$ is a 4-, 5- or 6-membered saturated heterocyclic group with 1–2 heteroatoms, selected independently from O, S and N, which heterocyclic group is linked to C$_{1-5}$alkyl through a carbon atom and which heterocyclic group may bear 1 or 2 substituents selected from oxo, hydroxy, halogeno, cyano, C$_{1-4}$cyanoalkyl, C$_{1-4}$alkyl, C$_{1-4}$hydroxyalkyl, C$_{1-4}$alkoxy, C$_{1-4}$alkanoyl, C$_{1-4}$alkoxyC$_{1-4}$alkyl, C$_{1-4}$alkylsulphonyl, C$_{1-4}$alkylsulphonylC$_{1-4}$alkyl, C$_{1-4}$alkoxycarbonyl, C$_{1-4}$alkylamino, di(C$_{1-4}$alkyl)amino, C$_{1-4}$alkylamino C$_{1-4}$alkyl, di(C$_{1-4}$alkyl)aminoC$_{1-4}$alkyl, C$_{1-4}$alkylaminoC$_{1-4}$alkoxy, di(C$_{1-4}$alkyl)amino C$_{1-4}$alkoxy and a group —(—O—)$_f$(C$_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from C$_{1-4}$alkyl)) or C$_{2-5}$alkylR$^{57}$ (wherein R$^{57}$ is a 4-, 5- or 6-membered saturated heterocyclic group with 1–2 heteroatoms, of which one is N and the other may be selected independently from O, S and N, which heterocyclic group is linked to C$_{2-5}$alkyl through a nitrogen atom and which heterocyclic group may bear 1 or 2 substituents selected from oxo, hydroxy, halogeno, cyano, C$_{1-4}$cyanoalkyl, C$_{1-4}$alkyl, C$_{1-4}$hydroxyalkyl, C$_{1-4}$alkoxy, C$_{1-4}$alkanoyl, C$_{1-4}$alkoxyC$_{1-4}$alkyl, C$_{1-4}$alkylsulphonyl, C$_{1-4}$alkylsulphonylC$_{1-4}$alkyl, C$_{1-4}$alkoxycarbonyl, C$_{1-4}$alkylamino, di(C$_{1-4}$alkyl)amino, C$_{1-4}$alkylamino C$_{1-4}$alkyl, di(C$_{1-4}$alkyl)aminoC$_{1-4}$alkyl, C$_{1-4}$alkylaminoC$_{1-4}$ alkoxy, di(C$_{1-4}$alkyl)amino C$_{1-4}$alkoxy and a group —(—O—)$_f$(C$_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from C$_{1-4}$alkyl));
7) C$_{3-4}$alkenylR$^{58}$ (wherein R$^{58}$ represents R$^{56}$ or R$^{57}$ as defined hereinbefore);
8) C$_{3-4}$alkynylR$^{58}$ (wherein R$^{58}$ represents R$^{56}$ or R$^{57}$ as defined hereinbefore);
9) R$^{29}$ (wherein R$^{29}$ is as defined hereinbefore);
10) C$_{1-5}$alkylR$^{29}$ (wherein R$^{29}$ is as defined hereinbefore);
11) C$_{3-5}$alkenylR$^{29}$ (wherein R$^{29}$ is as defined hereinbefore);
12) C$_{3-5}$alkynylR$^{29}$ (wherein R$^{29}$ is as defined hereinbefore);
13) C$_{1-5}$alkylX$^6$R$^{29}$ (wherein X$^6$ and R$^{29}$ are as defined hereinbefore);
14) C$_{4-5}$alkenylX$^7$R$^{29}$ (wherein X$^7$ and R$^{29}$ are as defined hereinbefore);
15) C$_{4-5}$alkynylX$^8$R$^{29}$ (wherein X$^8$ and R$^{29}$ are as defined hereinbefore);
16) C$_{2-3}$alkylX$^9$C$_{1-3}$alkylR$^{29}$ (wherein X$^9$ and R$^{29}$ are as defined hereinbefore);
17) C$_{2-3}$alkylX$^9$C$_{1-3}$alkylR$^{28}$ (wherein X$^9$ and R$^{28}$ are as defined hereinbefore);
18) C$_{2-5}$alkenyl which may be unsubstituted or which may be substituted with one or more groups selected from hydroxy, fluoro, amino, C$_{1-4}$alkylamino, N,N-di(C$_{1-4}$alkyl)amino, aminosulphonyl, N-C$_{1-4}$alkylaminosulphonyl and N,N-di(C$_{1-4}$alkyl)aminosulphonyl;
19) C$_{2-5}$alkynyl which may be unsubstituted or which may be substituted with one or more groups selected from hydroxy, fluoro, amino, C$_{1-4}$alkylamino, N,N-di(C$_{1-4}$alkyl)amino, aminosulphonyl, N-C$_{1-4}$alkylaminosulphonyl and N,N-di(C$_{1-4}$alkyl)aminosulphonyl;
20) C$_{2-5}$alkenylX$^9$C$_{1-3}$alkylR$^{28}$ (wherein X$^9$ and R$^{28}$ are as defined hereinbefore);
21) C$_{2-5}$alkynylX$^9$C$_{1-3}$alkylR$^{28}$ (wherein X$^9$ and R$^{28}$ are as defined hereinbefore); and
22) C$_{1-3}$alkylR$^{54}$(C$_{1-3}$alkyl)$_q$(X$^9$)$_r$R$^{55}$ (wherein X$^9$, q, r, R$^{54}$ and R$^{55}$ are as defined hereinbefore);
and additionally wherein any C$_{1-5}$alkyl, C$_{2-5}$alkenyl or C$_{2-5}$alkynyl group in R$^5$X$^1$— may bear one or more substituents selected from hydroxy, halogeno and amino].

Advantageously $R^2$ represents hydroxy, halogeno, cyano, nitro, trifluoromethyl, C$_{1-3}$alkyl, amino or R$^5$X$^1$— [wherein X$^1$ is as hereinbefore defined and R$^5$ is selected from one of the following twenty-two groups:

1) C$_{1-4}$alkyl which may be unsubstituted or which may be substituted with one or more groups selected from fluoro, chloro and bromo, or C$_{2-5}$alkyl which may be unsubstituted or substituted with one or more groups selected from hydroxy and amino;
2) C$_{2-3}$alkylX$^2$C(O)R$^{11}$ (wherein X$^2$ is as hereinbefore defined and R$^{11}$ represents —NR$^{13}$R$^{14}$ or —OR$^{15}$ (wherein R$^{13}$, R$^{14}$ and R$^{15}$ which may be the same or different are each C$_{1-4}$alkyl or C$_{1-2}$alkoxyethyl));

3) $C_{2-4}$alkyl$X^3R^{16}$ (wherein $X^3$ is as hereinbefore defined and $R^{16}$ is a group selected from $C_{1-3}$alkyl, cyclopentyl, cyclohexyl, pyrrolidinyl, piperazinyl, piperidinyl, imidazolidinyl, azetidinyl and tetrahydropyranyl, which $C_{1-3}$alkyl group may bear 1 or 2 substituents selected from oxo, hydroxy, halogeno and $C_{1-2}$alkoxy and which cyclopentyl, cyclohexyl, pyrrolidinyl, piperazinyl, piperidinyl, imidazolidinyl, azetidinyl or tetrahydropyranyl group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl, $C_{1-2}$alkylsulphonyl$C_{1-3}$alkyl, $C_{1-3}$alkoxycarbonyl, $C_{1-3}$alkylamino, di($C_{1-3}$alkyl)amino, $C_{1-3}$alkylamino $C_{1-3}$alkyl, di($C_{1-3}$alkyl)amino($C_{1-3}$alkyl, $C_{1-3}$alkylamino$C_{1-3}$alkoxy, di($C_{1-3}$alkyl)amino $C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, azetidinyl, morpholino and thiomorpholino, which cyclic group may bear one or more substituents selected from $C_{1-3}$alkyl));

4) $C_{2-3}$alkyl$X^4C_{2-3}$alkyl$X^5R^{22}$ (wherein $X^4$ and $X^5$ are as hereinbefore defined and $R^{22}$ represents hydrogen or $C_{1-3}$alkyl);

5) $R^{28}$ (wherein $R^{28}$ is as defined hereinbefore);

6) $C_{1-4}$alkyl$R^{59}$ (wherein $R^{59}$ is a group selected from pyrrolidinyl, piperazinyl, piperidinyl, imidazolidin-1-yl, azetidinyl, 1,3-dioxolan-2-yl, 1,3-dioxan-2-yl, 1,3-dithiolan-2-yl and 1,3-dithian-2-yl, which group is linked to $C_{1-4}$alkyl through a carbon atom and which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkanoyl, $C_{1-2}$alkoxy$C_{1-3}$alkyl, $C_{1-2}$alkylsulphonyl, $C_{1-2}$alkylsulphonyl$C_{1-3}$alkyl, $C_{1-3}$alkoxycarbonyl, $C_{1-3}$alkylamino, di($C_{1-3}$alkyl)amino, $C_{1-3}$alkylamino $C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino $C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, azetidinyl, morpholino and thiomorpholino, which cyclic group may bear one or more substituents selected from $C_{1-3}$alkyl)) or $C_{2-4}$alkyl$R^{60}$ (wherein $R^{60}$ is a group selected from morpholino, thiomorpholino, azetidin-1-yl, pyrrolidin-1-yl, piperazin-1-yl and piperidino which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkanoyl, $C_{1-2}$alkoxy$C_{1-3}$alkyl, $C_{1-2}$alkylsulphonyl, $C_{1-2}$alkylsulphonyl$C_{1-3}$alkyl, $C_{1-3}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino $C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, azetidinyl, morpholino and thiomorpholino, which cyclic group may bear one or more substituents selected from $C_{1-3}$alkyl));

7) $C_{3-4}$alkenyl$R^{61}$ (wherein $R^{61}$ represents $R^{59}$ or $R^{60}$ as defined hereinbefore);

8) $C_{3-4}$alkynyl$R^{61}$ (wherein $R^{61}$ represents $R^{59}$ or $R^{60}$ as defined hereinbefore);

9) $R^{29}$ (wherein $R^{29}$ is as defined hereinbefore);

10) $C_{1-4}$alkyl$R^{29}$ (wherein $R^{29}$ is as defined hereinbefore);

11) 1-$R^{29}$prop-1-en-3-yl or 1-$R^{29}$but-2-en-4-yl (wherein $R^{29}$ is as defined hereinbefore with the proviso that when $R^5$ is 1-$R^{29}$prop-1-en-3-yl, $R^{29}$ is linked to the alkenyl group via a carbon atom);

12) 1-$R^{29}$prop-1-yl-3-yl or 1-$R^{29}$but-2-yn-4-yl (wherein $R^{29}$ is as defined hereinbefore with the proviso that when $R^5$ is 1-$R^{29}$prop-1-yn-3-yl, $R^{29}$ is linked to the alkynyl group via a carbon atom);

13) $C_{1-5}$alkyl$X^6R^{29}$ (wherein $X^6$ and $R^{29}$ are as defined hereinbefore);

14) 1-($R^{29}X^7$)but-2-en-4-yl (wherein $X^7$ and $R^{29}$ are as defined hereinbefore);

15) 1-($R^{29}X^8$)but-2-yn-4-yl (wherein $X^8$ and $R^{29}$ are as defined hereinbefore);

16) $C_{2-3}$alkyl$X^9C_{1-3}$alkyl$R^{29}$ (wherein $X^9$ and $R^{29}$ are as defined hereinbefore);

17) $C_{2-3}$alkyl$X^9C_{1-3}$alkyl$R^{28}$ (wherein $X^9$ and $R^{28}$ are as defined hereinbefore);

18) $C_{2-5}$alkenyl which may be unsubstituted or which may be substituted with one or more fluorine atoms or with one or two groups selected from hydroxy, fluoro, amino, $C_{1-4}$alkylamino, N,N-di($C_{1-4}$alkyl)amino, aminosulphonyl, N-$C_{1-4}$alkylaminosulphonyl and N,N-di($C_{1-4}$alkyl)aminosulphonyl;

19) $C_{2-5}$alkynyl which may be unsubstituted or which may be substituted with one or more fluorine atoms or with one or two groups selected from hydroxy, fluoro, amino, $C_{1-4}$alkylamino, N,N-di($C_{1-4}$alkyl)amino, aminosulphonyl, N-$C_{1-4}$alkylaminosulphonyl and N,N-di($C_{1-4}$alkyl)aminosulphonyl;

20) $C_{2-4}$alkenyl$X^9C_{1-3}$alkyl$R^{28}$ (wherein $X^9$ and $R^{28}$ are as defined hereinbefore);

21) $C_{2-4}$alkynyl$X^9C_{1-3}$alkyl$R^{28}$ (wherein $X^9$ and $R^{28}$ are as defined hereinbefore); and 22) $C_{1-3}$alkyl$R^{54}$($C_{1-3}$alkyl)$_q$($X^9$)$_r$$R^{55}$ (wherein $X^9$, q, r, $R^{54}$ and $R^{55}$ are as defined hereinbefore);

and additionally wherein any $C_{1-5}$alkyl, $C_{2-5}$alkenyl or $C_{2-5}$alkynyl group in $R^5X^1$— may bear one or more substituents selected from hydroxy, halogeno and amino].

Preferably $R^2$ represents hydroxy, halogeno, nitro, trifluoromethyl, $C_{1-3}$alkyl, cyano, amino or $R^5X^1$— [wherein $X^1$ is as hereinbefore defined and $R^5$ is selected from one of the following twenty groups:

1) $C_{1-3}$alkyl which may be unsubstituted or which may be substituted with one or more groups selected from fluoro, chloro and bromo, or $C_{2-3}$alkyl which may be unsubstituted or substituted with one or more groups selected from hydroxy and amino;

2) 2-(3,3-dimethylureido)ethyl, 3-(3,3-dimethylureido)propyl, 2-(3-methylureido)ethyl, 3-(3-methylureido)propyl, 2-ureidoethyl, 3-ureidopropyl, 2-(N,N-dimethylcarbamoyloxy)ethyl, 3-(N,N-dimethylcarbamoyloxy)propyl, 2-(N-methylcarbamoyloxy)ethyl, 3-(N-methylcarbamoyloxy)propyl, 2-(carbamoyloxy)ethyl, 3-(carbamoyloxy)propyl, or 2-(N-methyl-N-(butoxycarbonyl)amino)ethyl;

3) $C_{2-3}$alkyl$X^3R^{16}$ (wherein $X^3$ is as hereinbefore defined and $R^{16}$ is a group selected from $C_{1-3}$alkyl, cyclopentyl, cyclohexyl, pyrrolidinyl, piperidinyl, piperazinyl, azetidinyl, imidazolidinyl and tetrahydropyranyl which group is linked to $X^3$ through a carbon atom and which $C_{1-3}$alkyl group may bear 1 or 2 substituents selected from hydroxy, halogeno and $C_{1-2}$alkoxy and which cyclopentyl, cyclohexyl, pyrrolidinyl, piperidinyl, piperazinyl, azetidinyl, imidazolidinyl or tetralhydropyranyl group may bear one substituent selected from oxo, hydroxy, halogeno, cyano, $C_{1-2}$cyanoalkyl, $C_{1-2}$alkyl, $C_{1-2}$hydroxyalkyl, $C_{1-2}$alkoxy, $C_{1-2}$alkoxy$C_{1-3}$alkyl, $C_{1-2}$alkylsulphonyl$C_{1-3}$alkyl, $C_{1-2}$alkoxycarbonyl, $C_{1-3}$alkylamino, di($C_{1-3}$alkyl)amino, $C_{1-3}$alkylamino $C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino $C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino));
4) $C_{2-3}$alkyl$X^4C_{2-3}$alkyl$X^5R^{22}$ (wherein $X^4$ and $X^5$ are as hereinbefore defined and $R^{22}$ represents hydrogen or $C_{1-2}$alkyl);
5) $R^{28}$ (wherein $R^{28}$ is as defined hereinbefore);
6) $C_{1-3}$alkyl$R^{59}$ (wherein $R^{59}$ is a group selected from pyrrolidinyl, piperazinyl, piperidinyl, azetidinyl, imidazolidinyl, 1,3-dioxolan-2-yl, 1,3-dioxan-2-yl, 1,3-dithiolan-2-yl and 1,3-dithian-2-yl, which group is linked to $C_{1-3}$alkyl through a carbon atom and which group may bear 1 or 2 substituents selected from oxo, hydroxy, halogeno, cyano, $C_{1-2}$cyanoalkyl, $C_{1-2}$alkyl, $C_{1-2}$hydroxyalkyl, $C_{1-2}$alkoxy, $C_{1-2}$alkanoyl, $C_{1-2}$alkoxy$C_{1-3}$alkyl, $C_{1-2}$alkylsulphonyl, $C_{1-2}$alkylsulphonyl$C_{1-3}$alkyl, $C_{1-2}$alkoxycarbonyl, $C_{1-3}$alkylamino, di($C_{1-3}$alkyl)amino, $C_{1-3}$alkylamino $C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino $C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino)) or $C_{2-3}$alkyl$R^{60}$ (wherein $R^{60}$ is a group selected from morpholino, thiomorpholino, azetidin-1-yl, pyrrolidin-1-yl, piperazin-1-yl and piperidino which group may bear 1 or 2 substituents selected from oxo, hydroxy, halogeno, cyano, $C_{1-2}$cyanoalkyl, $C_{1-2}$alkyl, $C_{1-2}$hydroxyalkyl, $C_{1-2}$alkoxy, $C_{1-2}$alkanoyl, $C_{1-2}$alkoxy$C_{1-3}$alkyl, $C_{1-2}$alkylsulphonyl, $C_{1-2}$alkylsulphonyl$C_{1-3}$alkyl, $C_{1-2}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino $C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino));
7) $R^{29}$ (wherein $R^{29}$ is as defined hereinbefore);
8) $C_{1-4}$alkyl$R^{29}$ (wherein $R^{29}$ is as defined hereinbefore);
9) 1-$R^{29}$but-2-en-4-yl (wherein $R^{29}$ is as defined hereinbefore);
10) 1-$R^{29}$but-2-yn-4-yl (wherein $R^{29}$ is as defined hereinbefore);
11) $C_{1-3}$alkyl$X^6R^{29}$ (wherein $X^6$ and $R^{29}$ are as defined hereinbefore);
12) 1-($R^{29}X^7$)but-2-en-4-yl (wherein $X^7$ and $R^{29}$ are as defined hereinbefore);
13) 1-($R^{29}X^8$)but-2-yn-4-yl (wherein $X^8$ and $R^{29}$ are as defined hereinbefore);
14) $C_{2-3}$alkyl$X^9C_{1-3}$alkyl$R^{29}$ (wherein $X^9$ and $R^{29}$ are as defined hereinbefore);
15) $C_{2-3}$alkyl$X^9C_{1-3}$alkyl$R^{28}$ (wherein $X^9$ and $R^{28}$ are as defined hereinbefore);
16) $C_{2-5}$alkenyl which may be unsubstituted or which may be substituted with one or more fluorine atoms or with one or two groups selected from hydroxy, fluoro, amino, $C_{1-4}$alkylamino, N,N-di($C_{1-4}$alkyl)amino, aminosulphonyl, N-$C_{1-4}$alkylaminosulphonyl and N,N-di($C_{1-4}$alkyl)aminosulphonyl;
17) $C_{2-5}$alkynyl which may be unsubstituted or which may be substituted with one or more fluorine atoms or with one or two groups selected from hydroxy, fluoro, amino, $C_{1-4}$alkylamino, N,N-di($C_{1-4}$alkyl)amino, aminosulphonyl, N-$C_{1-4}$alkylaminosulphonyl and N,N-di($C_{1-4}$alkyl)aminosulphonyl;
18) $C_{2-3}$alkenyl$X^9C_{1-3}$alkyl$R^{28}$ (wherein $X^9$ and $R^{28}$ are as defined hereinbefore);
19) $C_{2-3}$alkynyl$X^9C_{1-3}$alkyl$R^{28}$ (wherein $X^9$ and $R^{28}$ are as defined hereinbefore); and
20) $C_{1-3}$alkyl$R^{54}$($C_{1-3}$alkyl)$_q$($X^9$)$_r$$R^{55}$ (wherein $X^9$, q, r, $R^{54}$ and $R^{55}$ are as defined hereinbefore);
and additionally wherein any $C_{1-5}$alkyl, $C_{2-5}$alkenyl or $C_{2-5}$alkynyl group in $R^5X^1$— may bear one or more substituents selected from hydroxy, halogeno and amino].

More preferably $R^2$ represents hydroxy, $C_{1-3}$alkyl, amino or $R^5X^1$— [wherein $X^1$ is as hereinbefore defined and $R^5$ represents methyl, ethyl, benzyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(ethylsulphinyl)ethyl, 2-(ethylsulphonyl)ethyl, 2-(N,N-dimethylsulphamoyl)ethyl, 2-(N-methylsulphamoyl)ethyl, 2-sulphamoylethyl, 2-(methylamino)ethyl, 3-(methylamino)propyl, 2-(ethylamino)ethyl, 3-(ethylamino)propyl, 2-(N,N-dimethylamino)ethyl, 3-(N,N-dimethylamino)propyl, 2-(N,N-diethylamino)ethyl, 3-(N,N-diethylamino)propyl, 2-(N-methyl-N-methylsulphonylamino)ethyl, 3-(N-methyl-N-methylsulphonylamino)propyl, 2-morpholinoethyl, 3-morpholinopropyl, 2-piperidinoethyl, 3-piperidinopropyl, 2-(methylpiperidino)ethyl, 3-(methylpiperidino)propyl, 2-(ethylpiperidino)ethyl, 3-(ethylpiperidino)propyl, 2-((2-methoxyethyl)piperidino)ethyl, 3-((2-methoxyethyl)piperidino)propyl, 2-((2-methylsulphonyl)ethylpiperidino)ethyl, 3-((2-methylsulphonyl)ethylpiperidino)propyl, piperidin-3-ylmethyl, piperidin-4-ylmethyl, 2-(piperidin-3-yl)ethyl, 2-(piperidin-4-yl)ethyl, 3-(piperidin-3-yl)propyl, 3-(piperidin-4-yl)propyl, 2-(piperidin-2-yl)ethyl, 3-(piperidin-2-yl)propyl, (1-methylpiperidin-3-yl)methyl, (1-methylpiperidin-4-yl)methyl, 2-(4-hydroxypiperidino)ethyl, 3-(4-hydroxypiperidino)propyl, (1-cyanomethylpiperidin-3-yl)methyl, (1-cyanomethylpiperidin-4-yl)methyl, 2-(methylpiperidin-3-yl)ethyl, 2-(methylpiperidin-4-yl)ethyl, 2-(1-cyanomethylpiperidin-3-yl)ethyl, 2-(1-cyanomethylpiperidin-4-yl)ethyl, 3-(methylpiperidin-3-yl)propyl, 3-(methylpiperidin-4-yl)propyl, 3-(1-cyanomethylpiperidin-3-yl)propyl, 3-(1-cyanomethylpiperidin-4-yl)propyl, 2-(ethylpiperidin-3-yl)ethyl, 2-(ethylpiperidin-4-yl)ethyl, 3-(ethylpiperidin-3-yl)propyl, 3-(ethylpiperidin-4-yl)propyl, ((2-methoxyethyl)piperidin-3-yl)methyl, ((2-methoxyethyl)piperidin-4-yl)methyl, 2-((2-methoxyethyl)piperidin-3-yl)ethyl, 2-((2-methoxyethyl)piperidin-4-yl)ethyl, 3-((2-methoxyethyl)piperidin-3-yl)propyl, 3-((2-methoxyethyl)piperidin-4-yl)propyl, (1-(2-methylsulphonylethyl)piperidin-3-yl)methyl, (1-(2-methylsulphonylethyl)piperidin-4-yl)methyl, 2-((2-methylsulphonylethyl)piperidin-3-yl)ethyl, 2-((2-methylsulphonylethyl)piperidin-4-yl)ethyl, 3-((2-methylsulphonylethyl)piperidin-3-yl)propyl, 3-((2-methylsulphonylethyl)piperidin-4-yl)propyl, 1-isopropylpiperidin-2-ylmethyl, 1-isopropylpiperidin-3-ylmethyl, 1-isopropylpiperidin-4-ylmethyl, 2-(1-isopropylpiperidin-2-yl)ethyl, 2-(1-isopropylpiperidin-3-yl)ethyl, 2-(1-isopropylpiperidin-4-yl)ethyl, 3-(1-isopropylpiperidin-2-yl)propyl, 3-(1-isopropylpiperidin-3-yl)propyl, 3-(1-isopropylpiperidin-4-yl)propyl, 2-(piperidin-4-yloxy)ethyl, 3-(piperidin-4-yloxy)propyl, 2-(1-(cyanomethyl)piperidin-4-yloxy)ethyl, 3-(1-(cyanomethyl)piperidin-4-yloxy)propyl, 2-(1-(2-cyanoethyl)piperidin-4- yloxy)ethyl, 3-(1-(2-cyanoethyl)piperidin-4-yloxy)propyl, 2-(piperazin-1-yl)ethyl, 3-piperazin-1-yl)propyl, (pyrrolidin-2-yl)methyl, 2-(pyrrolidin-1-yl)ethyl, 3-(pyrrolidin-1-yl)propyl, (2-oxo-tetrahydro-2H-pyrrolidin-5-yl)methyl, 5(R)-(2-oxo-tetrahydro-2H-pyrrolidin-5-yl)methyl, (5S)-(2-oxo-tetrahydro-2H-pyrrolidin-5-yl)methyl, (1,3-dioxolan-2-yl)methyl, 2-(1,3-dioxolan-2-yl)ethyl, 2-(2-methoxyethylamino)ethyl, 2-(N-(2-methoxyethyl)-N-methylamino)ethyl, 2-(2-hydroxyethylamino)ethyl, 3-(2-methoxyethylamino)propyl, 3-(N-(2-methoxyethyl)-N-methylamino)propyl, 3-(2-hydroxyethylamino)propyl, 2-methylthiazol-4-ylmethyl, 2-acetamidothiazol-4-ylmethyl, 1-methylimidazol-2-ylmethyl, 2-(imidazol-1-yl)ethyl, 2-(2-methylimidazol-1-yl)ethyl, 2-(2-ethylimidazol-1-yl)ethyl, 3-(2-methylimidazol-1-yl)propyl, 3-(2-ethylimidazol-1-yl)propyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, 3-pyridylmethyl, 2-(3-pyridyl)ethyl, 3-(3-pyridyl)propyl, 2-(4-pyridyloxy)ethyl, 2-(4-pyridylamino)ethyl, 2-(4-oxo-1,4-dihydro-1-pyridyl)ethyl, 2-(2-oxo-imidazolidin-1-yl)ethyl, 3-(2-oxo-imidazolidin-1-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy)ethyl, 2-(4-methylpiperazin-1-yl)ethyl, 3-(4-methylpiperazin-1-yl)propyl, 2-(4-cyanomethylpiperazin-1-yl)ethyl, 3-(4-cyanomethylpiperazin-1-yl)propyl, 2-(4-acetylpiperazin-1-yl)ethyl, 3-(4-acetylpiperazin-1-yl)propyl, 2-(4-methylsulphonylpiperazin-1-yl)ethyl, 3-(4-methylsulphonylpiperazin-1-yl)propyl, 3-(methylsulphinyl)propyl, 3-(methylsulphonyl)propyl, 3-(ethylsulphinyl)propyl, 3-(ethylsulphonyl)propyl, 2-(5-methyl-1,2,4-triazol-1-yl)ethyl, morpholino, 2-((N-(1-methylimidazol-4-ylsulphonyl)-N-methyl)amino)ethyl, 2-((N-(3-morpholinopropylsulphonyl)-N-methyl)amino)ethyl, 2-((N-methyl-N-4-pyridyl)amino)ethyl, 3-(4-oxidomorpholino)propyl, 2-(2-(4-methylpiperazin-1-yl)ethoxy)ethyl, 3-(2-(4-methylpiperazin-1-yl)ethoxy)propyl, 2-(2-morpholinoethoxy)ethyl, 3-(2-morpholinoethoxy)propyl, 2-(tetrahydropyran-4-yloxy)ethyl, 3-(tetrahydropyran-4-yloxy)propyl, 2-((2-(pyrrolidin-1-yl)ethyl)carbamoyl)vinyl, 3-((2-(pyrrolidin-1-yl)ethyl)carbamoyl)prop-2-en-1-yl, 1-(2-pyrrolidinylethyl)piperidin-4-ylmethyl, 1-(3-pyrrolidinylpropyl)piperidin-4-ylmethyl, 1-(2-piperidinylethyl)piperidin-4-ylmethyl, 1-(2-piperidinylpropyl)piperidin-4-ylmethyl, 1-(2-morpholinoethyl)piperidin-4-ylmethyl, 1-(3-morpholinopropyl)piperidin-4-ylmethyl, 1-(2-thiomorpholinoethyl)piperidin-4-ylmethyl, 1-(3-thiomorpholinopropyl)piperidin-4-ylmethyl, 1-(2-azetidinylethyl)piperidin-4-ylmethyl, 1-(3-azetidinylpropyl)piperidin-4-ylmethyl, 2-(1-(2-pyrrolidinylethyl)piperidin-4-yl)ethyl, 2-(1-(3-pyrrolidinylpropyl)piperidin-4-yl)ethyl, 2-(1-(2-piperidinylethyl)piperidin-4-yl)ethyl, 2-(1-(3-piperidinylpropyl)piperidin-4-yl)ethyl, 2-(1-(2-morpholinoethyl)piperidin-4-yl)ethyl, 2-(1-(3-morpholinopropyl)piperidin-4-yl)ethyl, 2-(1-(2-thiomorpholinoethyl)piperidin-4-yl)ethyl, 2-(1-(3-thiomorpholinopropyl)piperidin-4-yl)ethyl, 2-(1-(2-azetidinylethyl)piperidin-4-yl)ethyl, 2-(1-(3-azetidinylpropyl)piperidin-4-yl)ethyl, 3-morpholino-2-hydroxypropyl, (2R)-3-morpholino-2-hydroxypropyl, (2S)-3-morpholino-2-hydroxypropyl, 3-piperidino-2-hydroxypropyl, (2R)-3-piperidino-2-hydroxypropyl, (2S)-3-piperidino-2-hydroxypropyl, 3-pyrrolidin-1-yl-2-hydroxypropyl, (2R)-3-pyrrolidin-1-yl-2-hydroxypropyl, (2S)-3-pyrrolidin-1-yl-2-hydroxypropyl, 3-(1-methylpiperazin-4-yl)-2-hydroxypropyl, (2R)-3-(1-methylpiperazin-4-yl)-2-hydroxypropyl, (2S)-3-(1-methylpiperazin-4-yl-2-hydroxypropyl, 3-N,N-diethylamino)-2hydroxypropyl, (2R)-3-(N,N-diethylamino)-2-hydroxypropyl, (2S)-3-(N,N-diethylamino)-2-hydroxypropyl, 3-(isopropylamino)-2-hydroxypropyl, (2R)-3-(isopropylamino)-2-hydroxypropyl, (2R)-3-(N,N-diisopropylamino)-2-hydroxypropyl or (2S)-3-(N,N-diisopropylamino)-2-hydroxypropyl].

Particularly $R^2$ represents $C_{1-3}$alkyl, amino or $R^5X^1$—[wherein $X^1$ is as hereinbefore defined and $R^5$ represents ethyl, benzyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(ethylsulphinyl)ethyl, 2-(ethylsulphonyl)ethyl, 2-(N,N-dimethylsulphamoyl)ethyl, 2-(N-methylsulphamoyl)ethyl, 2-sulphamoylethyl, 2-(methylamino)ethyl, 3-(methylamino)propyl, 2-(ethylamino)ethyl, 3-(ethylamino)propyl, 2-(N,N-dimethylamino)ethyl, 3-(N,N-dimethylamino)propyl, 2-(N,N-diethylamino)ethyl, 3-(N,N-diethylamino)propyl, 2-(N-methyl-N-methylsulphonylamino)ethyl, 3-(N-methyl-N-methylsulphonylamino)propyl, 2-morpholinoethyl, 3-morpholinopropyl, 2-piperidinoethyl, 3-piperidinopropyl, 2-(methylpiperidino)ethyl, 3-(methylpiperidino)propyl, 2-(ethylpiperidino)ethyl, 3-(ethylpiperidino)propyl, 2-((2-methoxyethyl)piperidino)ethyl, 3-((2-methoxyethyl)piperidino)propyl, 2-((2-methylsulphonyl)ethylpiperidino)ethyl, 3-((2-methylsulphonyl)ethylpiperidino)propyl, piperidin-3-ylmethyl, piperidin-4-ylmethyl, 2-(piperidin-3-yl)ethyl, 2-(piperidin-4-yl)ethyl, 3-(piperidin-3-yl)propyl, 3-(piperidin-4-yl)propyl, 2-(piperidin-2-yl)ethyl, 3-(piperidin-2-yl)propyl, (1-methylpiperdin-3-yl)methyl, (1-methylpiperidin-4-yl)methyl, 2-(4-hydroxypiperidino)ethyl, 3-(4-hydroxypiperidino)propyl, (1-cyanomethylpiperidin-3-yl)methyl, (1-cyanomethylpiperidin-4-yl)methyl, 2-(methylpiperidin-3-yl)ethyl, 2-(methylpiperidin-4-yl)ethyl, 2-(2-cyanomethylpiperidin-3-methylpiperidin-4-yl)propyl, 3-(1-cyanomethylpiperidin-3-yl)propyl, 3-(1-cyanomethylpiperidin-4-yl)propyl, 2-(ethylpiperidin-3-yl)ethyl, 2-(ethylpiperidin-4-yl)ethyl, 3-(ethylpiperidin-3-yl)propyl, 3-(ethylpiperidin-4-yl)propyl, ((2-methoxyethyl)piperidin-3-yl)methyl, ((2-methoxyethyl)piperidin-4-yl)methyl, 2-((2-methoxyethyl)piperidin-3-yl)ethyl, 2-((2-methoxyethyl)piperidin-4-yl)ethyl, 3-((2-methoxyethyl)piperidin-3-yl)propyl, 3-((2-methoxyethyl)piperidin-4-yl)propyl, (1-(2-methylsulphonylethyl)piperidin-3-yl)methyl, (1-(2-methylsulphonylethyl)piperidin-4-yl)methyl, 2-((2-methylsulphonylethyl)piperidin-3-yl)ethyl, 2-((2-methylsulphonylethyl)piperidin-4-yl)ethyl, 3-((2-methylsulphonylethyl)piperidin-3-yl)propyl, 3-((2-methylsulphonylethyl)piperidin-4-yl)propyl, 1-isopropylpiperidin-2-ylmethyl, 1-isopropylpiperidin-3-ylmethyl, 1-isopropylpiperidin-4-ylmethyl, 2-(1-isopropylpiperidin-2-yl)ethyl, 2-(1-isopropylpiperidin-3-yl)ethyl, 2-(1-isopropylpiperidin-4-yl)ethyl, 3-(1-isopropylpiperidin-2-yl)propyl, 3-(1-isopropylpiperidin-3-yl)propyl, 3-(1-isopropylpiperidin-4-yl)propyl, 2-(piperidin-4-yloxy)ethyl, 3-(piperidin-4-yloxy)propyl, 2-(1-(cyanomethyl)piperidin-4-yloxy)ethyl, 3-(1-(cyanomethyl)piperidin-4-yloxy)propyl, 2-(1-(2-cyanoethyl)piperidin-4-yloxy)ethyl, 3-(1-(2-cyanoethyl)piperidin-4-yloxy)propyl, 2-(piperazin-1-yl)ethyl, 3-(piperazin-1-yl)propyl, (pyrrolidin-2-yl)methyl, 2-(pyrrolidin-1-yl)ethyl, 3-(pyrrolidin-1-yl)propyl, (2-oxo-tetrahydro-2H-pyrrolidin- 5-yl)methyl, 5(R)-(2-oxo-tetrahydro-2H-pyrrolidin-5-yl) methyl, (5S)-(2-oxo-tetrahydro-2H-pyrrolidin-5-yl)methyl, (1,3-dioxolan-2-yl)methyl, 2-(1,3-dioxolan-2-yl)ethyl, 2-(2-methoxyethylamino)ethyl, 2-(N-(2-methoxyethyl)-N-methylamino)ethyl, 2-(2-hydroxyethylamino)ethyl, 3-(2-methoxyethylamino)propyl, 3-(N-(2-methoxyethyl)-N-methylamino)propyl, 3-(2-hydroxyethylamino)propyl, 2-methylthiazol-4-ylmethyl, 2-acetamidothiazol-4-ylmethyl, 1-methylimidazol-2-ylmethyl, 2-(imidazol-1-yl) ethyl, 2-(2-methylimidazol-1-yl)ethyl, 2-(2-ethylimidazol-1-yl)ethyl, 3-(2-methylimidazol-1-yl)propyl, 3-(2-ethylimidazol-1-yl)propyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, 3-pyridylmethyl, 2-(3-pyridyl)ethyl, 3-(3-pyridyl)propyl, 2-(4-pyridyloxy)ethyl, 2-(4-pyridylamino) ethyl, 2-(4-oxo-1,4-dihydro-1-pyridyl)ethyl, 2-(2-oxo-imidazolidin-1-yl)ethyl, 3-(2-oxo-imidazolidin-1-yl)propyl, 2-thiomorpholinoethyl, 3-thiomorpholinopropyl, 2-(1,1-dioxothiomorpholino)ethyl, 3-(1,1-dioxothiomorpholino) propyl, 2-(2-methoxyethoxy)ethyl, 2-(4-methylpiperazin-1-yl)ethyl, 3-(4-methylpiperazin-1-yl)propyl, 2-(4-cyanomethylpiperazin-1-yl)ethyl, 3-(4-cyanomethylpiperazin-1-yl)propyl, 2-(4-acetylpiperazin-1-yl)ethyl, 3-(4-acetylpiperazin-1-yl)propyl, 2-(4-methylsulphonylpiperazin-1-yl)ethyl, 3-(4-methylsulphonylpiperazin-1-yl)propyl, 3-(methylsulphinyl) propyl, 3-(methylsulphonyl)propyl, 3-(ethylsulphinyl) propyl, 3-(ethylsulphonyl)propyl, 2-(5-methyl-1,2,4-triazol-1-yl)ethyl, morpholino, 2-((N-(1-methylimidazol-4-ylsulphonyl)-N-methyl)amino)ethyl, 2-((N-(3-morpholinopropylsulphonyl)-N-methyl)amino)ethyl, 2-((N-methyl-N-4-pyridyl)amino)ethyl, 3-(4-oxidomorpholino) propyl, 2-(2-(4-methylpiperazin-1-yl)ethoxy)ethyl, 3-(2-(4-methylpiperazin-1-yl)ethoxy)propyl, 2-(2-morpholinoethoxy)ethyl, 3-(2-morpholinoethoxy)propyl, 2-(tetrahydropyran-4-yloxy)ethyl, 3-(tetrahydropyran-4-yloxy)propyl, 2-((2-(pyrrolidin-1-yl)ethyl)carbamoyl)vinyl, 3-((2-(pyrrolidin-1-yl)ethyl)carbamoyl)prop-2-en-1-yl, 1-(2-pyrrolidinylethyl)piperidin-4-ylmethyl, 1-(3-pyrrolidinylpropyl)piperidin-4-ylmethyl, 1-(2-piperidinylethyl)piperidin-4-ylmethyl, 1-(3-piperidinylpropyl)piperidin-4-ylmethyl, 1-(2-morpholinoethyl)piperidin-4-ylmethyl, 1-(3-morpholinopropyl)piperidin-4-ylmethyl, 1-(2-thiomorpholinoethyl)piperidin-4-ylmethyl, 1-(3-thiomorpholinopropyl)piperidin-4-ylmethyl, 1-(2-azetidinylethyl)piperidin-4-ylmethyl, 1-(3-azetidinylpropyl) piperidin-4-ylmethyl, 2-(1-(2-pyrrolidinylethyl)piperidin-4-yl)ethyl, 2-(1-(3-pyrrolidinylpropyl)piperidin-4-yl)ethyl, 2-(1-(2-piperidinylethyl)piperidin-4-yl)ethyl, 2-(1-(3-piperidinylpropyl)piperidin-4-yl)ethyl, 2-(1-(2-morpholinoethyl)piperidin-4-yl)ethyl, 2-(1-(3-morpholinopropyl)piperidin-4-yl)ethyl, 2-(1-(2-thiomorpholinoethyl)piperidin-4-yl)ethyl, 2-(1-(3-thiomorpholinopropyl)piperidin-4-yl)ethyl, 2-(1-(2-azetidinylethyl)piperidin-4-yl)ethyl, 2-(1-(3-azetidinylpropyl)piperidin-4-yl)ethyl, 3-morpholino-2-hydroxypropyl, (2R)-3-morpholino-2-hydroxypropyl, (2S)-3-morpholino-2-hydroxypropyl, 3-piperidino-2-hydroxypropyl, (2R)-3-piperidino-2-hydroxypropyl, (2S)-3-piperidino-2-hydroxypropyl, 3-pyrrolidin-1-yl-2-hydroxypropyl, (2R)-3-pyrrolidin-1-yl-2-hydroxypropyl, (2S)-3-pyrrolidin-1-yl-2-hydroxypropyl, 3-(1-methylpiperazin-4-yl)-2-hydroxypropyl, (2R)-3-(1-methylpiperazin-4-yl)-2-hydroxypropyl, (2S)-3-(1-methylpiperazin-4-yl)-2-hydroxypropyl, 3-(N,N-diethylamino)-2-hydroxypropyl, (2R)-3-(N,N-diethylamino)-2-hydroxypropyl, (2S)-3-(N,N-diethylamino)-2-hydroxypropyl, 3-(isopropylamino)-2-hydroxypropyl, (2R)-3-(isopropylamino)-2-hydroxypropyl, (2S)-3-(isopropylamino)-2-hydroxypropyl, 3-(N,N-diisopropylamino)-2-hydroxypropyl, (2R)-3-(N,N-diisopropylamino)-2-hydroxypropyl or (2S)-3-(N,N-diisopropylamino)-2-hydroxypropyl].

More particularly $R^2$ represents $C_{1-3}$alkyl, amino or $R^5X^1$— [wherein $X^1$ is as hereinbefore defined and $R^5$ represents ethyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(ethylsulphinyl)ethyl, 2-(ethylsulphonyl)ethyl, 2-(N,N-dimethylsulphamoyl)ethyl, 2-(N-methylsulphamoyl)ethyl, 2-sulphamoylethyl, 2-(methylamino)ethyl, 3-(methylamino)propyl, 2-(ethylamino)ethyl, 3-(ethylamino)propyl, 2-(N,N-dimethylamino)ethyl, 3-(N,N-dimethylamino)propyl, 2-(N,N-diethylamino)ethyl, 3-(N,N-diethylamino)propyl, 2-(N-methyl-N-methylsulphonylamino)ethyl, 3-(N-methyl-N-methylsulphonylamino)propyl, 2-morpholinoethyl, 3-morpholinopropyl, 2-piperidinoethyl, 3-piperidinopropyl, 2-(methylpiperidino)ethyl, 3-(methylpiperidino)propyl, 2-(ethylpiperidino)ethyl, 3-(ethylpiperidino)propyl, 2-((2-methoxyethyl)piperidino)ethyl, 3-((2-methoxyethyl) piperidino)propyl, 2-((2-methylsulphonyl)ethylpiperidino) ethyl, 3-((2-methylsulphonyl)ethylpiperidino)propyl, piperidin-3-ylmethyl, piperidin-4-ylmethyl, 2-(piperidin-3-yl)ethyl, 2-(piperidin-4-yl)ethyl, 3-(piperidin-3-yl)propyl, 3-(piperidin-4-yl)propyl, 2-(piperidin-2-yl)ethyl, 3-(piperidin-2-yl)propyl, (1-methylpiperidin-3-yl)methyl, (1-methylpiperidin-4-yl)methyl, 2-(4-hydroxypiperidino) ethyl, 3-(4-hydroxypiperidino)propyl, (1-cyanomethylpiperidin-3-yl)methyl, (1-cyanomethylpiperidin-4-yl)methyl, 2-(methylpiperidin-3-yl)ethyl, 2-(methylpiperidin-4-yl)ethyl, 2-(1-cyanomethylpiperidin-3-yl)ethyl, 2-(1-cyanomethylpiperidin-4-yl)ethyl, 3-(methylpiperidin-3-yl) propyl, 3-(methylpiperidin-4-yl)propyl, 3-(1-cyanomethylpiperidin-3-yl)propyl, 3-(1-cyanomethylpiperidin-4-yl)propyl, 2-(ethylpiperidin-3-yl) ethyl, 2-(ethylpiperidin-4-yl)ethyl, 3-(ethylpiperidin-3-yl) propyl, 3-(ethylpiperidin-4-yl)propyl, ((2-methoxyethyl) piperidin-3-yl)methyl, ((2-methoxyethyl)piperidin-4-yl) methyl, 2-((2-methoxyethyl)piperidin-3-yl)ethyl, 2-((2-methoxyethyl)piperidin-4-yl)ethyl, 3-((2-methoxyethyl) piperidin-3-yl)propyl, 3-((2-methoxyethyl)piperidin-4-yl) propyl, (1-(2-methylsulphonylethyl)piperidin-3-yl)methyl, (1-(2-methylsulphonylethyl)piperidin-4-yl)methyl, 2-((2-methylsulphonylethyl)piperidin-3-yl)ethyl, 2-((2-methylsulphonylethyl)piperidin-4-yl)ethyl, 3-((2-methylsulphonylethyl)piperidin-3-yl)propyl, 3-((2-methylsulphonylethyl)piperidin-4-yl)propyl, 1-isopropylpiperidin-2-ylmethyl, 1-isopropylpiperidin-3-ylmethyl, 1-isopropylpiperidin-4-ylmethyl, 2-(1-isopropylpiperidin-2-yl)ethyl, 2-(1-isopropylpiperidin-3-yl) ethyl, 2-(1-isopropylpiperidin-4-yl)ethyl, 3-(1-isopropylpiperidin-2-yl)propyl, 3-(1-isopropylpiperidin-3-yl)propyl, 3-(1-isopropylpiperidin-4-yl)propyl, 2-(piperidin-4-yloxy)ethyl, 3-(piperidin-4-yloxy)propyl, 2-(1-(cyanomethyl)piperidin-4-yloxy)ethyl, 3-(1-(cyanomethyl) piperidin-4-yloxy)propyl, 2-(1-(2-cyanoethyl)piperidin-4-yloxy)ethyl, 3-(1-(2-cyanoethyl)piperidin-4-yloxy)propyl, 2-(piperazin-1-yl)ethyl, 3-(piperazin-1-yl)propyl, (pyrrolidin-2-yl)methyl, 2-(pyrrolidin-1-yl)ethyl, 3-pyrrolidin-1-yl)propyl, (2-oxo-tetrahydro-2H-pyrrolidin- 5-yl)methyl, 5(R)-(2-oxo-tetrahydro-2H-pyrrolidin-5-yl)methyl, (5S)-(2-oxo-tetrahydro-2H-pyrrolidin-5-yl)methyl, (1,3-dioxolan-2-yl)methyl, 2-(1,3-dioxolan-2-yl)ethyl, 2-(2-methoxyethylamino)ethyl, 2-(N-(2-methoxyethyl)-N-methylamino)ethyl, 2-(2-hydroxyethylamino)ethyl, 3-(2-methoxyethylamino)propyl, 3-(N-(2-methoxyethyl)-N-methylamino)propyl, 3-(2-hydroxyethylamino)propyl, 2-(1,2,3-triazol-1-yl)ethyl, 2-(1,2,3-triazol-1-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, 3-pyridylmethyl, 2-(3-pyridyl)ethyl, 3-(3-pyridyl)propyl, 2-(4-pyridyloxy)ethyl, 2-(4-pyridylamino)ethyl, 2-(4-oxo-1,4-dihydro-1-pyridyl)ethyl, 2-(2-oxo-imidazolidin-1-yl)ethyl, 3-(2-oxo-imidazolidin-1-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy)ethyl, 2-(4-methylpiperazin-1-yl)ethyl, 3-(4-methylpiperazin-1-yl)propyl, 2-(4-cyanomethylpiperazin-1-yl)ethyl, 3-(4-cyanomethylpiperazin-1-yl)propyl, 2-(4-acetylpiperazin-1-yl)ethyl, 3-(4-acetylpiperazin-1-yl)propyl, 2-(4-methylsulphonylpiperazin-1-yl)ethyl, 3-(4-methylsulphonylpiperazin-1-yl)propyl, 3-(methylsulphinyl)propyl, 3-(methylsulphonyl)propyl, 3-(ethylsulphinyl)propyl, 3-(ethylsulphonyl)propyl, 2-(5-methyl-1,2,4-triazol-1-yl)ethyl, morpholino, 2-((N-(3-morpholinopropylsulphonyl)-N-methyl)amino)ethyl, 2-((N-methyl-N-4-pyridyl)amino)ethyl, 3-(4-oxidomorpholino)propyl, 2-(2-(4-methylpiperazin-1-yl)ethoxy)ethyl, 3-(2-(4-methylpiperazin-1-yl)ethoxy)propyl, 2-(2-morpholinoethoxy)ethyl, 3-(2-morpholinoethoxy)propyl, 2-(tetrahydropyran-4-yloxy)ethyl, 3-(tetrahydropyran-4-yloxy)propyl, 2-((2-(pyrrolidin-1-yl)ethyl)carbamoyl)vinyl, 3-((2-(pyrrolidin-1-yl)ethyl)carbamoyl)prop-2-en-1-yl, 1-(2-pyrrolidinylethyl)piperidin-4-ylmethyl, 1-(3-pyrrolidinylpropyl)piperidin-4-ylmethyl, 1-(2-piperidinylethyl)piperidin-4-ylmethyl, 1-(3-piperidinylpropyl)piperidin-4-ylmethyl, 1-(2-morpholinoethyl)piperidin-4-ylmethyl, 1-(3-morpholinopropyl)piperidin-4-ylmethyl, 1-(2-thiomorpholinoethyl)piperidin-4-ylmethyl, 1-(3-thiomorpholinopropyl)piperidin-4-ylmethyl, 1-(2-azetidinylethyl)piperidin-4-ylmethyl or 1-(3-azetidinylpropyl)piperidin-4-ylmethyl, 2-(1-(2-pyrrolidinylethyl)piperidin-4-yl)ethyl, 2-(1-(3-pyrrolidinylpropyl)piperidin-4-yl)ethyl, 2-(1-(2-piperidinylethyl)piperidin-4-yl)ethyl, 2-(1-(3-piperidinylpropyl)piperidin-4-yl)ethyl, 2-(1-(2-morpholinoethyl)piperidin-4-yl)ethyl, 2-(1-(3-morpholinopropyl)piperidin-4-yl)ethyl, 2-(1-(2-thiomorpholinoethyl)piperidin-4-yl)ethyl, 2-(1-(3-thiomorpholinopropyl)piperidin-4-yl)ethyl; 2-(1-(2-azetidinylethyl)piperidin-4-yl)ethyl, 2-(1-(3-azetidinylpropyl)piperidin-4-yl)ethyl, 3-morpholino-2-hydroxypropyl, (2R)-3-morpholino-2-hydroxypropyl, (2S)-3-morpholino-2-hydroxypropyl, 3-piperidino-2-hydroxypropyl, (2R)-3-piperidino-2-hydroxypropyl, (2S)-3-piperidino-2-hydroxypropyl, 3-pyrrolidin-1-yl-2-hydroxypropyl, (2R)-3-pyrrolidin-1-yl-2-hydroxypropyl, (2S)-3-pyrrolidin-1-yl-2-hydroxypropyl, 3-(1-methylpiperazin-4-yl)-2-hydroxypropyl, (2R)-3-(1-methylpiperazin-4-yl)-2-hydroxypropyl, (2S)-3-(1-methylpiperazin-4-yl)-2-hydroxypropyl, 3-(N,N-diethylamino)-2-hydroxypropyl, (2R)-3-N,N-diethylamino)-2-hydroxypropyl, (2S)-3-(N,N-diethylamino)-2-hydroxypropyl, 3-(isopropylamino)-2-hydroxypropyl, (2R)-3-(isopropylamino)-2-hydroxypropyl, (2S)-3-(isopropylamino)-2-hydroxypropyl, 3-(N,N-diisopropylamino)-2-hydroxypropyl, (2R)-3-(N,N-diisopropylamino)-2-hydroxypropyl or (2S)-3-(N,N-diisopropylamino)-2hydroxypropyl].

In another aspect $R^2$ represents ethoxy, trifluoromethoxy, 2,2,2-trifluoroethoxy, 2-hydroxyethoxy, 3-hydroxypropoxy, 2-methoxyethoxy, 3-methoxypropoxy, 2-(methylsulphinyl)ethoxy, 2-(methylsulphonyl)ethoxy, 2-(ethylsulphinyl)ethoxy, 2-(ethylsulphonyl)ethoxy, 2-N,N-dimethylsulphamoyl)ethoxy, 2-(N-methylsulphamoyl)ethoxy, 2-sulphamoylethoxy, 2-(methylamino)ethoxy, 3-(methylamino)propoxy, 2-(ethylamino)ethoxy, 3-(ethylamino)propoxy, 2-(N,N-dimethylamino)ethoxy, 3-(N,N-dimethylamino)propoxy, 2-(N,N-diethylamino)ethoxy, 3-(N,N-diethylamino)propoxy, 2-(N-methyl-N-methylsulphonylamino)ethoxy, 3-(N-methyl-N-methylsulphonylamino)propoxy, 2-morpholinoethoxy, 3-morpholinopropoxy, 2-piperidinoethoxy, 3-piperidinopropoxy, 2-(methylpiperidino)ethoxy, 3-(methylpiperidino)propoxy, 2-(ethylpiperidino)ethoxy, 3-(ethylpiperidino)propoxy, 2-((2-methoxyethyl)piperidino)ethoxy, 3-((2-methoxyethyl)piperidino)propoxy, 2-((2-methylsulphonyl)ethylpiperidino)ethoxy, 3-((2-methylsulphonyl)ethylpiperidino)propoxy, piperidin-3-ylmethoxy, piperidin-4-ylmethoxy, 2-(piperidin-3-yl)ethoxy, 2-(piperidin-4-yl)ethoxy, 3-(piperidin-3-yl)propoxy, 3-(piperidin-4-yl)propoxy, 2-piperidin-2-yl)ethoxy, 3-(piperidin-2-yl)propoxy, (1-methylpiperidin-3-yl)methoxy, (1-methylpiperidin-4-yl)methoxy, 2-(4-hydroxypiperidino)ethoxy, 3-(4-hydroxypiperidino)propoxy, (1-cyanomethylpiperidin-3-yl)methoxy, (1-cyanomethylpiperidin-4-yl)methoxy, 2-(methylpiperidin-3-yl)ethoxy, 2-(methylpiperidin-4-yl)ethoxy, 2-(1-cyanomethylpiperidin-3-yl)ethoxy, 2-(1-cyanomethylpiperidin-4-yl)ethoxy, 3-(methylpiperidin-3-yl)propoxy, 3-(methylpiperidin-4-yl)propoxy, 3-(1-cyanomethylpiperidin-3-yl)propoxy, 3-(1-cyanomethylpiperidin-4-yl)propoxy, 2-(ethylpiperidin-3-yl)ethoxy, 2-(ethylpiperidin-4-yl)ethoxy, 3-(ethylpiperidin-3-yl)propoxy, 3-(ethylpiperidin-4-yl)propoxy, ((2-methoxyethyl)piperidin-3-yl)methoxy, ((2-methoxyethyl)piperidin-4-yl)methoxy, 2-((2-methoxyethyl)piperidin-3-yl)ethoxy, 2-((2-methoxyethyl)piperidin-4-yl)ethoxy, 3-((2-methoxyethyl)piperidin-3-yl)propoxy, 3-((2-methoxyethyl)piperidin-4-yl)propoxy, (1-(2-methylsulphonylethyl)piperidin-3-yl)methoxy, (1-(2-methylsulphonylethyl)piperidin-4-yl)methoxy, 2-((2-methylsulphonylethyl)piperidin-3-yl)ethoxy, 2-((2-methylsulphonylethyl)piperidin-4-yl)ethoxy, 3-((2-methylsulphonylethyl)piperidin-3-yl)propoxy, 3-((2-methylsulphonylethyl)piperidin-4-yl)propoxy, 1-isopropylpiperidin-2-ylmethoxy, 1-isopropylpiperidin-3-ylmethoxy, 1-isopropylpiperidin-4-ylmethoxy, 2-(1-isopropylpiperidin-2-yl)ethoxy, 2-(1-isopropylpiperidin-3-yl)ethoxy, 2-(1-isopropylpiperidin-4-yl)ethoxy, 3-(1-isopropylpiperidin-2-yl)propoxy, 3-(1-isopropylpiperidin-3-yl)propoxy, 3-(1-isopropylpiperidin-4-yl)propoxy, 2-(piperidin-4-yloxy)ethoxy, 3-(piperidin-4-yloxy)propoxy, 2-(1-(cyanomethyl)piperidin-4-yloxy)ethoxy, 3-(1-(cyanomethyl)piperidin-4-yloxy)propoxy, 2-(1-(2-cyanoethyl)piperidin-4-yloxy)ethoxy, 3-(1-(2-cyanoethyl)piperidin-4-yloxy)propoxy, 2-(piperazin-1-yl)ethoxy, 3-(piperazin-1-yl)propoxy, (pyrrolidin-2-yl)methoxy, 2-(pyrrolidin-1-yl)ethoxy, 3-(pyrrolidin-1-yl)propoxy, (2-oxo-tetrahydro-2H-pyrrolidin-5-yl)methoxy, 5(R)-(2-oxo-tetrahydro-2H-pyrrolidin-5-yl)methoxy, (5S)-(2-oxo-tetrahydro-2H-pyrrolidin-5-yl)methoxy, (1,3-dioxolan-2-yl)methoxy, 2-(1,3-dioxolan-2-yl)ethoxy, 2-(2- methoxyethylamino)ethoxy, 2-(N-(2-methoxyethyl)-N-methylamino)ethoxy, 2-(2-hydroxyethylamino)ethoxy, 3-(2-methoxyethylamino)propoxy, 3-(N-(2-methoxyethyl)-N-methylamino)propoxy, 3-(2-hydroxyethylamino)propoxy, 2-(1,2,3-triazol-1-yl)ethoxy, 2-(1,2,3-triazol-2-yl)ethoxy, 2-(1,2,4-triazol-1-yl)ethoxy, 2-(1,2,4-triazol-4-yl)ethoxy, 4-pyridylmethoxy, 2-(4-pyridyl)ethoxy, 3-(4-pyridyl)propoxy, 3-pyridylmethoxy, 2-(3-pyridyl)ethoxy, 3-(3-pyridyl)propoxy, 2-(4-pyridyloxy)ethoxy, 2-(4-pyridylamino)ethoxy, 2-(4-oxo-1,4-dihydro-1-pyridyl)ethoxy, 2-(2-oxo-imidazolidin-1-yl)ethoxy, 3-(2-oxo-imidazolidin-1-yl)propoxy, 2-thiomorpholinoethoxy, 3-thiomorpholinopropoxy, 2-(1,1-dioxothiomorpholino)ethoxy, 3-(1,1-dioxothiomorpholino)propoxy, 2-(2-methoxyethoxy)ethoxy, 2-(4-methylpiperazin-1-yl)ethoxy, 3-(4-methylpiperazin-1-yl)propoxy, 2-(4-cyanomethylpiperazin-1-yl)ethoxy, 3-(4-cyanomethylpiperazin-1-yl)propoxy, 2-(4-acetylpiperazin-1-yl)ethoxy, 3-(4-acetylpiperazin-1-yl)propoxy, 2-(4-methylsulphonylpiperazin-1-yl)ethoxy, 3-(4-methylsulphonylpiperazin-1-yl)propoxy, 3-(methylsulphinyl)propoxy, 3-(methylsulphonyl)propoxy, 3-(ethylsulphinyl)propoxy, 3-(ethylsulphonyl)propoxy, 2-(5-methyl-1,2,4-triazol-1-yl)ethoxy, 2-((N-(3-morpholinopropylsulphonyl)-N-methyl)amino)ethoxy, 2-((N-methyl-N-4-pyridyl)amino)ethoxy, 3-(4-oxidomorpholino)propoxy, 2-(2-(4-methylpiperazin-1-yl)ethoxy)ethoxy, 3-(2-(4-methylpiperazin-1-yl)ethoxy)propoxy, 2-(2-morpholinoethoxy)ethoxy, 3-(2-morpholinoethoxy)propoxy, 2-(tetrahydropyran-4-yloxy)ethoxy, 3-(tetrahydropyran-4-yloxy)propoxy, 2-((2-(pyrrolidin-1-yl)ethyl)carbamoyl)vinyl, 3-((2-(pyrrolidin-1-yl)ethyl)carbamoyl)prop-2-en-1-yloxy, 1-(2-pyrrolidinylethyl)piperidin-4-ylmethoxy, 1-(3-pyrrolidinylpropyl)piperidin-4-ylmethyoxy, 1-(2-piperidinylethyl)piperidin-4-ylmethoxy, 1-(3-piperidinylpropyl)piperidin-4-ylmethoxy, 1-(2-morpholinoethyl)piperidin-4-ylmethoxy, 1-(3-morpholinopropyl)piperidin-4-ylmethoxy, 1-(2-thiomorpholinoethyl)piperidin-4-ylmethoxy, 1-(3-thiomorpholinopropyl)piperidin-4-ylmethoxy, 1-(2-azetidinylethyl)piperidin-4-ylmethoxy, 1-(3-azetidinylpropyl)piperidin-4-ylmethoxy, 2-(1-(2-pyrrolidinylethyl)piperidin-4-yl)ethoxy, 2-(1-(3-pyrrolidinylpropyl)piperidin-4-yl)ethoxy, 2-(1-(2-piperidinylethyl)piperidin-4-yl)ethoxy, 2-(1-(3-piperidinylpropyl)piperidin-4-yl)ethoxy, 2-(1-(2-morpholinoethyl)piperidin-4-yl)ethoxy, 2-(1-(3-morpholinopropyl)piperidin-4-yl)ethoxy, 2-(1-(2-thiomorpholinoethyl)piperidin-4-yl)ethoxy, 2-(1-(3-thiomorpholinopropyl)piperidin-4-yl)ethoxy, 2-(1-(2-azetidinylethyl)piperidin-4-yl)ethoxy, 2-(1-(3-azetidinylpropyl)piperidin-4-yl)ethoxy, 3-morpholino-2-hydroxypropoxy, (2R)-3-morpholino-2-hydroxypropoxy, (2S)-3-morpholino-2-hydroxypropoxy, 3-piperidino-2-hydroxypropoxy, (2R)-3-piperidino-2-hydroxypropoxy, (2S)-3-piperidino-2-hydroxypropoxy, 3-pyrrolidin-1-yl-2-hydroxypropoxy, (2R)-3-pyrrolidin-1-yl-2-hydroxypropoxy, (2S)-3-pyrrolidin-1-yl-2-hydroxypropoxy, 3-(1-methylpiperazin-4-yl)-2-hydroxypropoxy, (2R)-3-(1-methylpiperazin-4-yl)-2-hydroxypropoxy, (2S)-3-(1-methylpiperazin-4-yl)-2-hydroxypropoxy, 3-(N,N-diethylamino)-2-hydroxypropoxy, (2R)-3-(N,N-diethylamino)-2-hydroxypropoxy, (2S)-3-(N,N-diethylamino)-2-hydroxypropoxy, 3-(isopropylamino)-2-hydroxypropoxy, (2R)-3-(isopropylamino)-2-hydroxypropoxy, (2S)-3-(isopropylamino)-2-hydroxypropoxy, 3-(N,N-diisopropylamino)-2-hydroxypropoxy, (2R)-3-(N,N-diisopropylamino)-2-hydroxypropoxy or (2S)-3-(N,N-diisopropylamino)-2-hydroxypropoxy.

According to another aspect of the present invention conveniently $R^2$ represents hydroxy, halogeno, cyano, nitro, trifluoromethyl, $C_{1-3}$alkyl, amino or $R^5X^1$— [wherein $X^1$ is as hereinbefore defined and $R^5$ is selected from one of the following twenty-two groups:

1) oxiranyl$C_{1-4}$alkyl or $C_{1-5}$alkyl which may be unsubstituted or which may be substituted with one or more groups selected from fluoro, chloro and bromo, or $C_{2-5}$alkyl which may be unsubstituted or substituted with one or more groups selected from hydroxy and amino;

2) $C_{2-3}$alkyl$X^2$C(O)$R^{11}$ (wherein $X^2$ is as hereinbefore defined and $R^{11}$ represents $C_{1-3}$alkyl, —NR$^{13}$R$^{14}$ or —OR$^{15}$ (wherein $R^{13}$, $R^{14}$ and $R^{15}$ which may be the same or different are each $C_{1-4}$alkyl or $C_{1-2}$alkoxyethyl));

3) $C_{2-4}$alkyl$X^3$R$^{16}$ (wherein $X^3$ is as hereinbefore defined and $R^{16}$ represents hydrogen, $C_{1-3}$alkyl, cyclopentyl, cyclohexyl or a 4-, 5- or 6-membered saturated heterocyclic group with 1–2 heteroatoms, selected independently from O, S and N, which $C_{1-3}$alkyl group may bear 1 or 2 substituents selected from oxo, hydroxy, halogeno and $C_{1-3}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino $C_{1-4}$alkoxy and a group —(—O—)$_f$($C_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from $C_{1-4}$alkyl));

4) $C_{2-3}$alkyl$X^4$C$_{2-3}$alkyl$X^5$R$^{22}$ (wherein $X^4$ and $X^5$ are as hereinbefore defined and $R^{22}$ represents hydrogen or $C_{1-3}$alkyl);

5) $R^{28}$ (wherein $R^{28}$ is as defined hereinbefore);

6) $C_{1-5}$alkyl$R^{56}$ (wherein $R^{56}$ is a 4-, 5- or 6-membered saturated heterocyclic group with 1–2 heteroatoms, selected independently from O, S and N, which heterocyclic group is linked to $C_{1-5}$alkyl through a carbon atom and which heterocyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino $C_{1-4}$alkoxy and a group —(—O—)$_f$($C_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from $C_{1-4}$alkyl)) or $C_{2-5}$alkyl$R^{57}$ (wherein $R^{57}$ is a 4-, 5- or 6-membered saturated heterocyclic group with 1–2 heteroatoms, of which one is N and the other may be selected independently from O, S and N, which heterocyclic group is linked to $C_{2-5}$alkyl through a nitrogen atom and which heterocyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$akylsulphonyl$C_{1-4}$alkyl, $C_{1-4}$alkoxycarbonyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino $C_{1-4}$alkoxy and a group —(—O—)$_f$($C_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from $C_{1-4}$alkyl));

7) $C_{3-4}$alkenyl$R^{58}$ (wherein $R^{58}$ represents $R^{56}$ or $R^{57}$ as defined hereinbefore);
8) $C_{3-4}$alkynyl$R^{58}$ (wherein $R^{58}$ represents $R^{56}$ or $R^{57}$ as defined hereinbefore);
9) $R^{29}$ (wherein $R^{29}$ is as defined hereinbefore);
10) $C_{1-5}$alkyl$R^{29}$ (wherein $R^{29}$ is as defined hereinbefore);
11) $C_{3-5}$alkenyl$R^{29}$ (wherein $R^{29}$ is as defined hereinbefore);
12) $C_{3-5}$alkynyl$R^{29}$ (wherein $R^{29}$ is as defined hereinbefore);
13) $C_{1-5}$alkyl$X^6R^{29}$ (wherein $X^6$ and $R^{29}$ are as defined hereinbefore);
14) $C_{4-5}$alkenyl$X^7R^{29}$ (wherein $X^7$ and $R^{29}$ are as defined hereinbefore);
15) $C_{4-5}$alkynyl$X^8R^{29}$ (wherein $X^8$ and $R^{29}$ are as defined hereinbefore);
16) $C_{2-3}$alkyl$X^9C_{1-3}$alkyl$R^{29}$ (wherein $X^9$ and $R^{29}$ are as defined hereinbefore);
17) $C_{2-3}$alkyl$X^9C_{1-3}$alkyl$R^{28}$ (wherein $X^9$ and $R^{28}$ are as defined hereinbefore);
18) $C_{2-5}$alkenyl which may be unsubstituted or which may be substituted with one or more groups selected from hydroxy, fluoro, amino, $C_{1-4}$alkylamino, N,N-di($C_{1-4}$alkyl)amino, aminosulphonyl, N-$C_{1-4}$alkylaminosulphonyl and N,N-di($C_{1-4}$alkyl)aminosulphonyl;
19) $C_{2-5}$alkynyl which may be unsubstituted or which may be substituted with one or more groups selected from hydroxy, fluoro, amino, $C_{1-4}$alkylamino, N,N-di($C_{1-4}$alkyl)amino, aminosulphonyl, N-$C_{1-4}$alkylaminosulphonyl and N,N-di($C_{1-4}$alkyl)aminosulphonyl;
20) $C_{2-5}$alkenyl$X^9C_{1-3}$alkyl$R^{28}$ (wherein $X^9$ and $R^{28}$ are as defined hereinbefore);
21) $C_{2-5}$alkynyl$X^9C_{1-3}$alkyl$R^{28}$ (wherein $X^9$ and $R^{28}$ are as defined hereinbefore); and
22) $C_{1-3}$alkyl$R^{54}(C_{1-3}$alkyl)$_q(X^9)_rR^{55}$ (wherein $X^9$, q, r, $R^{54}$ and $R^{55}$ are as defined hereinbefore);

and additionally wherein any $C_{1-5}$alkyl, $C_{2-5}$alkenyl or $C_{2-5}$alkynyl group in $R^5X^1$— may bear one or more substituents selected from hydroxy, halogeno and amino].

According to another aspect of the present invention advantageously $R^2$ represents hydroxy, halogeno, cyano, nitro, trifluoromethyl, $C_{1-3}$alkyl, amino or $R^5X^1$— [wherein $X^1$ is as hereinbefore defined and $R^5$ is selected from one of the following twenty-two groups:

1) $C_{1-4}$alkyl which may be unsubstituted or which may be substituted with one or more groups selected from fluoro, chloro and bromo, or $C_{2-5}$alkyl which may be unsubstituted or substituted with one or more groups selected from hydroxy and amino;
2) $C_{2-3}$alkyl$X^2C(O)R^{11}$ (wherein $X^2$ is as hereinbefore defined and $R^{11}$ represents —NR$^{13}R^{14}$ or —OR$^{15}$ (wherein $R^{13}$, $R^{14}$ and $R^{15}$ which may be the same or different are each $C_{1-4}$alkyl or $C_{1-2}$alkoxyethyl));
3) $C_{2-4}$alkyl$X^3R^{16}$ (wherein $X^3$ is as hereinbefore defined and $R^{16}$ is a group selected from $C_{1-3}$alkyl, cyclopentyl, cyclohexyl, pyrrolidinyl, piperazinyl, piperidinyl, imidazolidinyl, azetidinyl and tetrahydropyranyl, which $C_{1-3}$alkyl group may bear 1 or 2 substituents selected from oxo, hydroxy, halogeno and $C_{1-2}$alkoxy and which cyclopentyl, cyclohexyl, pyrrolidinyl, piperazinyl, piperidinyl, imidazolidinyl, azetidinyl or tetrahydropyranyl group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl, $C_{1-2}$alkylsulphonyl$C_{1-3}$alkyl, $C_{1-3}$alloxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino $C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, azetidinyl, morpholino and thiomorpholino, which cyclic group may bear one or more substituents selected from $C_{1-3}$alkyl));
4) $C_{2-3}$alkyl$X^4C_{2-3}$alkyl$X^5R^{22}$ (wherein $X^4$ and $X^5$ are as hereinbefore defined and $R^{22}$ represents hydrogen or $C_{1-3}$alkyl);
5) $R^{28}$ (wherein $R^{28}$ is as defined hereinbefore);
6) $C_{1-4}$alkyl$R^{59}$ (wherein $R^{59}$ is a group selected from pyrrolidinyl, piperazinyl, piperidinyl, imidazolidin-1-yl, azetidinyl, 1,3-dioxolan-2-yl, 1,3-dioxan-2-yl, 1,3-dithiolan-2-yl and 1,3-dithian-2-yl, which group is linked to $C_{1-4}$alkyl through a carbon atom and which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl, $C_{1-2}$alkylsulphonyl$C_{1-3}$alkyl, $C_{1-3}$alkoxycarbonyl, $C_{1-3}$alkylamino, di($C_{1-3}$alkyl)amino, $C_{1-3}$alkylamino $C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino $C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, azetidinyl, morpholino and thiomorpholino, which cyclic group may bear one or more substituents selected from $C_{1-3}$alkyl)) or $C_{2-4}$alkyl$R^{60}$ (wherein $R^{60}$ is a group selected from morpholino, thiomorpholino, azetidin-1-yl, pyrrolidin-1-yl, piperazin-1-yl and piperidino which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl, $C_{1-2}$alkylsulphonyl $C_{1-3}$alkyl, $C_{1-3}$alkoxycarbonyl, $C_{1-3}$alkylamino, di($C_3$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino$C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, azetidinyl, morpholino and thiomorpholino, which cyclic group may bear one or more substituents selected from $C_{1-3}$alkyl));
7) $C_{3-4}$alkenyl$R^{61}$ (wherein $R^{61}$ represents $R^{59}$ or $R^{60}$ as defined hereinbefore);
8) $C_{3-4}$alkynyl$R^{61}$ (wherein $R^{61}$ represents $R^{59}$ or $R^{60}$ as defined hereinbefore);
9) $R^{29}$ (wherein $R^{29}$ is as defined hereinbefore);
10) $C_{1-4}$alkyl$R^{29}$ (wherein $R^{29}$ is as defined hereinbefore);
11) 1-$R^{29}$prop-1-en-3-yl or 1-$R^{29}$but-2-en-4-yl (wherein $R^{29}$ is as defined hereinbefore with the proviso that when $R^5$ is 1-$R^{29}$prop-1-en-3-yl, $R^{29}$ is linked to the alkenyl group via a carbon atom);
12) 1-$R^{29}$prop-1-yn-3-yl or 1-$R^{29}$but-2-yn-4-yl (wherein $R^{29}$ is as defined hereinbefore with the proviso that when $R^5$ is 1-$R^{29}$prop-1-yn-3-yl, $R^{29}$ is linked to the alkynyl group via a carbon atom);
13) $C_{1-5}$alkyl$X^6R^{29}$ (wherein $X^6$ and $R^{29}$ are as defined hereinbefore);

14) 1-($R^{29}X^7$)but-2-en-4-yl (wherein $X^7$ and $R^{29}$ are as defined hereinbefore);
15) 1-($R^{29}X^8$)but-2-yn-4-yl (wherein $X^8$ and $R^{29}$ are as defined hereinbefore);
16) $C_{2-3}$alkyl$X^9C_{1-3}$alkyl$R^{29}$ (wherein $X^9$ and $R^{29}$ are as defined hereinbefore);
17) $C_{2-3}$alkyl$X^9C_{1-3}$alkyl$R^{28}$ (wherein $X^9$ and $R^{28}$ are as defined hereinbefore);
18) $C_{2-5}$alkenyl which may be unsubstituted or which may be substituted with one or more fluorine atoms or with one or two groups selected from hydroxy, fluoro, amino, $C_{1-4}$alkylamino, N,N-di($C_{1-4}$alkyl)amino, aminosulphonyl, N-$C_{1-4}$alkylaminosulphonyl and N,N-di($C_{1-4}$alkyl)aminosulphonyl;
19) $C_{2-5}$alkynyl which may be unsubstituted or which may be substituted with one or more fluorine atoms or with one or two groups selected from hydroxy, fluoro, amino, $C_{1-4}$alkylamino, N,N-di($C_{1-4}$alkyl)amino, aminosulphonyl, N-$C_{1-4}$alkylaminosulphonyl and N,N-di($C_{1-4}$alkyl)aminosulphonyl;
20) $C_{2-4}$alkenyl$X^9C_{1-3}$alkyl$R^{28}$ (wherein $X^9$ and $R^{28}$ are as defined hereinbefore);
21) $C_{2-4}$alkynyl$X^9C_{1-3}$alkyl$R^{28}$ (wherein $X^9$ and $R^{28}$ are as defined hereinbefore); and
22) $C_{1-3}$alkyl$R^{54}(C_{1-3}$alkyl$)_q(X^9)_rR^{55}$ (wherein $X^9$, q, r, $R^{54}$ and $R^{55}$ are as defined hereinbefore);

and additionally wherein any $C_{1-5}$alkyl, $C_{2-5}$alkenyl or $C_{2-5}$alkynyl group in $R^5X^1$— may bear one or more substituents selected from hydroxy, halogeno and amino].

According to another aspect of the present invention preferably $R^2$ represents hydroxy, halogeno, nitro, trifluoromethyl, $C_{1-3}$alkyl, cyano, amino or $R^5X^1$— [wherein $X^1$ is as hereinbefore defined and $R^5$ is selected from one of the following twenty groups:

1) $C_{1-3}$alkyl which may be unsubstituted or which may be substituted with one or more groups selected from fluoro, chloro and bromo, or $C_{2-3}$alkyl which may be unsubstituted or substituted with one or more groups selected from hydroxy and amino;
2) 2-(3,3-dimethylureido)ethyl, 3-(3,3-dimethylureido)propyl, 2-(3-methylureido)ethyl, 3-(3-methylureido)propyl, 2-ureidoethyl, 3-ureidopropyl, 2-(N,N-dimethylcarbamoyloxy)ethyl, 3-(N,N-dimethylcarbamoyloxy)propyl, 2-(N-methylcarbamoyloxy)ethyl, 3-(N-methylcarbamoyloxy)propyl, 2-(carbamoyloxy)ethyl, 3-(carbamoyloxy)propyl, or 2-(N-methyl-N-(butoxycarbonyl)amino)ethyl;
3) $C_{2-3}$alkyl$X^3R^{16}$ (wherein $X^3$ is as hereinbefore defined and $R^{16}$ is a group selected from $C_{1-3}$alkyl, cyclopentyl, cyclohexyl, pyrrolidinyl, piperidinyl, piperazinyl, azetidinyl, imidazolidinyl and tetrahydropyranyl which group is linked to $X^3$ through a carbon atom and which $C_{1-3}$alkyl group may bear 1 or 2 substituents selected from hydroxy, halogeno and $C_{1-2}$alkoxy and which cyclopentyl, cyclohexyl, pyrrolidinyl, piperidinyl, piperazinyl, azetidinyl, imidazolidinyl or tetrahydropyranyl group may bear one substituent selected from oxo, hydroxy, halogeno, cyano, $C_{1-2}$cyanoalkyl, $C_{1-2}$alkyl, $C_{1-2}$hydroxyalkyl, $C_{1-2}$alkoxy, $C_{1-2}$alkoxy$C_{1-3}$alkyl, $C_{1-2}$alkylsulphonyl$C_{1-3}$alkyl, $C_{1-2}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino$C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino));
4) $C_{2-3}$alkyl$X^4C_{2-3}$alkyl$X^5R^{22}$ (wherein $X^4$ and $X^5$ are as hereinbefore defined and $R^{22}$ represents hydrogen or $C_{1-2}$alkyl),
5) $R^{28}$ (wherein $R^{28}$ is as defined hereinbefore);
6) $C_{1-3}$alkyl$R^{59}$ (wherein $R^{59}$ is a group selected from pyrrolidinyl, piperazinyl, piperidinyl, azetidinyl, imidazolidinyl, 1,3-dioxolan-2-yl, 1,3-dioxan-2-yl, 1,3-dithiolan-2-yl and 1,3-dithian-2-yl, which group is linked to $C_{1-3}$alkyl through a carbon atom and which group may bear 1 or 2 substituents selected from oxo, hydroxy, halogeno, cyano, $C_{1-2}$cyanoalkyl, $C_{1-2}$alkyl, $C_{1-2}$hydroxyalkyl, $C_{1-2}$alkoxy, $C_{1-2}$alkoxy$C_{1-3}$alkyl, $C_{1-2}$alkylsulphonyl$C_{1-3}$alkyl, $C_{1-2}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino$C_{1-3}$alkoxy and a group —(—O—)$_f$($C_{1-3}$alkyl)$_g$ringD (wherein f is 0 or -1, g is 0 or 1 and ring D is a heterocyclic group selected from pyrrolidinyl, methylpiperazinyl, piperidinyl, azetidinyl, morpholino and thiomorpholino)) or $C_{2-3}$alkyl$R^{60}$ (wherein $R^{60}$ is a group selected from morpholino, thiomorpholino, azetidin-1-yl, pyrrolidin-1-yl, piperazin-1-yl and piperidino which group may bear 1 or 2 substituents selected from oxo, hydroxy, halogeno, cyano, $C_{1-2}$cyanoalkyl, $C_{1-2}$alkyl, $C_{1-2}$hydroxyalkyl, $C_{1-2}$alkoxy, $C_{1-2}$alkoxy$C_{1-3}$alkyl, $C_{1-2}$alkylsulphonyl $C_{1-3}$alkyl, $C_{1-2}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino$C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino));
7) $R^{29}$ (wherein $R^{29}$ is as defined hereinbefore);
8) $C_{1-4}$alkyl$R^{29}$ (wherein $R^{29}$ is as defined hereinbefore);
9) 1-$R^{29}$but-2-en-4-yl (wherein $R^{29}$ is as defined hereinbefore);
10) 1-$R^{29}$but-2-yn-4-yl (wherein $R^{29}$ is as defined hereinbefore);
11) $C_{1-3}$alkyl$X^6R^{29}$ (wherein $X^6$ and $R^{29}$ are as defined hereinbefore);
12) 1-($R^{29}X^7$)but-2-en-4-yl (wherein $X^7$ and $R^{29}$ are as defined hereinbefore);
13) 1-($R^{29}X^8$)but-2-yn-4-yl (wherein $X^8$ and $R^{29}$ are as defined hereinbefore);
14) $C_{2-3}$alkyl$X^9C_{1-3}$alkyl$R^{29}$ (wherein $X^9$ and $R^{29}$ are as defined hereinbefore);
15) $C_{2-3}$alkyl$X^9C_{1-3}$alkyl$R^{28}$ (wherein $X^9$ and $R^{28}$ are as defined hereinbefore);
16) $C_{2-5}$alkenyl which may be unsubstituted or which may be substituted with one or more fluorine atoms or with one or two groups selected from hydroxy, fluoro, amino, $C_{1-4}$alkylamino, N,N-di($C_{1-4}$alkyl)amino, aminosulphonyl, N-$C_{1-4}$alkylaminosulplhonyl and N,N-di($C_{1-4}$alkyl)aminosulphonyl;
17) $C_{2-5}$alkynyl which may be unsubstituted or which may be substituted with one or more fluorine atoms or with one or two groups selected from hydroxy, fluoro, amino, $C_{1-4}$alkylamino, N,N-di($C_{1-4}$alkyl)amino, aminosulphonyl, N-$C_{1-4}$alkylaminosulphonyl and N,N-di($C_4$alkyl)aminosulphonyl;
18) $C_{2-3}$alkenyl$X^9C_{1-3}$alkyl$R^{28}$ (wherein $X^9$ and $R^{28}$ are as defined hereinbefore);
19) $C_{2-3}$alkynyl$X^9C_{1-3}$alkyl$R^{28}$ (wherein $X^9$ and $R^{28}$ are as defined hereinbefore); and
20) $C_{1-3}$alkyl$R^{54}(C_{1-3}$alkyl$)_q(X^9)_rR^{55}$ (wherein $X^9$, q, r, $R^{54}$ and $R^{55}$ are as defined hereinbefore);

and additionally wherein any $C_{1-5}$alkyl, $C_{2-5}$alkenyl or $C_{2-5}$alkynyl group in $R^5X^1$— may bear one or more substituents selected from hydroxy, halogeno and amino].

According to another aspect of the present invention more preferably $R^2$ represents hydroxy, $C_{1-3}$alkyl, amino or $R^5X^1$— [wherein $X^1$ is as hereinbefore defined and $R^5$ represents methyl, ethyl, benzyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(ethylsulphinyl)ethyl, 2-(ethylsulphonyl)ethyl, 2-(N,N-dimethylsulphamoyl)ethyl, 2-(N-methylsulphamoyl)ethyl, 2-sulphamoylethyl, 2-(methylamino)ethyl, 3-(methylamino)propyl, 2-(ethylamino)ethyl, 3-(ethylamino)propyl, 2-(N,N-dimethylamino)ethyl, 3-(N,N-dimethylamino)propyl, 2-(N,N-diethylamino)ethyl, 3-(N,N-diethylamino)propyl, 2-(N-methyl-N-methylsulphonylamino)ethyl, 3-(N-methyl-N-methylsulphonylamino)propyl, 2-morpholinoethyl, 3-morpholinopropyl, 2-piperidinoethyl, 3-piperidinopropyl, 2-(methylpiperidino)ethyl, 3-(methylpiperidino)propyl, 2-(ethylpiperidino)ethyl, 3-(ethylpiperidino)propyl, 2-((2-methoxyethyl)piperidino)ethyl, 3-((2-methoxyethyl)piperidino)propyl, 2-((2-methylsulphonyl)ethylpiperidino)ethyl, 3-((2-methylsulphonyl)ethylpiperidino)propyl, piperidin-3-ylmethyl, piperidin-4-ylmethyl, 2-(piperidin-3-yl)ethyl, 2-(piperidin-4-yl)ethyl, 3-(piperidin-3-yl)propyl, 3-(piperidin-4-yl)propyl, 2-(piperidin-2-yl)ethyl, 3-(piperidin-2-yl)propyl, (1-methylpiperidin-3-yl)methyl, (1-methylpiperidin-4-yl)methyl, (1-cyanomethylpiperidin-3-yl)methyl, (1-cyanomethylpiperidin-4-yl)methyl, 2-(methylpiperidin-3-yl)ethyl, 2-(methylpiperidin-4-yl)ethyl, 2-(1-cyanomethylpiperidin-3-yl)ethyl, 2-(1-cyanomethylpiperidin-4-yl)ethyl, 3-(methylpiperidin-3-yl)propyl, 3-(methylpiperidin-4-yl)propyl, 3-(1-cyanomethylpiperidin-3-yl)propyl, 3-(1-cyanomethylpiperidin-4-yl)propyl, 2-(ethylpiperidin-3-yl)ethyl, 2-(ethylpiperidin-4-yl)ethyl, 3-(ethylpiperidin-3-yl)propyl, 3-(ethylpiperidin-4-yl)propyl, ((2-methoxyethyl)piperidin-3-yl)methyl, ((2-methoxyethyl)piperidin-4-yl)methyl, 2-((2-methoxyethyl)piperidin-3-yl)ethyl, 2-((2-methoxyethyl)piperidin-4-yl)ethyl, 3-((2-methoxyethyl)piperidin-3-yl)propyl, 3-((2-methoxyethyl)piperidin-4-yl)propyl, (1-(2-methylsulphonylethyl)piperidin-3-yl)methyl, (1-(2-methylsulphonylethyl)piperidin-4-yl)methyl, 2-((2-methylsulphonylethyl)piperidin-3-yl)ethyl, 2-((2-methylsulphonylethyl)piperidin-4-yl)ethyl, 3-((2-methylsulphonylethyl)piperidin-3-yl)propyl, 3-((2-methylsulphonylethyl)piperidin-4-yl)propyl, 1-isopropylpiperidin-2-ylmethyl, 1-isopropylpiperidin-3-ylmethyl, 1-isopropylpiperidin-4-ylmethyl, 2-(1-isopropylpiperidin-2-yl)ethyl, 2-(1-isopropylpiperidin-3-yl)ethyl, 2-(1-isopropylpiperidin-4-yl)ethyl, 3-(1-isopropylpiperidin-2-yl)propyl, 3-(1-isopropylpiperidin-3-yl)propyl, 3-(1-isopropylpiperidin-4-yl)propyl, 2-(piperidin-4-yloxy)ethyl, 3-(piperidin-4-yloxy)propyl, 2-(1-(cyanomethyl)piperidin-4-yloxy)ethyl, 3-(1-(cyanomethyl)piperidin-4-yloxy)propyl, 2-(1-(2-cyanoethyl)piperidin-4-yloxy)ethyl, 3-(1-(2-cyanoethyl)piperidin-4-yloxy)propyl, 2-(piperazin-1-yl)ethyl, 3-(piperazin-1-yl)propyl, (pyrrolidin-2-yl)methyl, 2-(pyrrolidin-1-yl)ethyl, 3-(pyrrolidin-1-yl)propyl, (2-oxo-tetrahydro-2H-pyrrolidin-5-yl)methyl, 5(R)-(2-oxo-tetrahydro-2H-pyrrolidin-5-yl)methyl, (5S)-(2-oxo-tetrahydro-2H-pyrrolidin-5-yl)methyl, (1,3-dioxolan-2-yl)methyl, 2-(1,3-dioxolan-2-yl)ethyl, 2-(2-methoxyethoxy)ethyl, 2-(N-(2-methoxyethyl)-N-methylamino)ethyl, 2-(2-hydroxyethylamino)ethyl, 3-(2-methoxyethylamino)propyl, 3-(N-(2-methoxyethyl)-N-methylamino)propyl, 3-(2-hydroxyethylamino)propyl, 2-methylthiazol-4-ylmethyl, 2-acetamidothiazol-4-ylmethyl, 1-methylimidazol-2-ylmethyl, 2-(imidazol-1-yl)ethyl, 2-(2-methylimidazol-1-yl)ethyl, 2-(2-ethylimidazol-1-yl)ethyl, 3-(2-methylimidazol-1-yl)propyl, 3-(2-ethylimidazol-1-yl)propyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, 2-(4-pyridyloxy)ethyl, 2-(4-pyridylamino)ethyl, 2-(4-oxo-1,4-dihydro-1-pyridyl)ethyl, 2-(2-oxo-imidazolidin-1-yl)ethyl, 3-(2-oxo-imidazolidin-1-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy)ethyl, 2-(4-methylpiperazin-1-yl)ethyl, 3-(4-methylpiperazin-1-yl)propyl, 3-(methylsulphinyl)propyl, 3-(methylsulphonyl)propyl, 3-(ethylsulphinyl)propyl, 3-(ethylsulphonyl)propyl, 2-(5-methyl-1,2,4-triazol-1-yl)ethyl, morpholino, 2-((N-(1-methylimidazol-4-ylsulphonyl)-N-methyl)amino)ethyl, 2-((N-(3-morpholinopropylsulphonyl)-N-methyl)amino)ethyl, 2-((N-methyl-N-4-pyridyl)amino)ethyl, 3-(4-oxidomorpholino)propyl, 2-(2-(4-methylpiperazin-1-yl)ethoxy)ethyl, 3-(2-(4-methylpiperazin-1-yl)ethoxy)propyl, 2-(2-morpholinoethoxy)ethyl, 3-(2-morpholinoethoxy)propyl, 2-(tetrahydropyran-4-yloxy)ethyl, 3-(tetrahydropyran-4-yloxy)propyl, 2-((2-(pyrrolidin-1-yl)ethyl)carbamoyl)vinyl, 3-((2-(pyrrolidin-1-yl)ethyl)carbamoyl)prop-2-en-1-yl, 1-(2-pyrrolidinylethyl)piperidin-4-ylmethyl, 1-(3-pyrrolidinylpropyl)piperidin-4-ylmethyl, 1-(2-piperidinylethyl)piperidin-4-ylmethyl; 1-(3-piperidinylpropyl)piperidin-4-ylmethyl, 1-(2-morpholinoethyl)piperidin-4-ylmethyl, 1-(3-morpholinopropyl)piperidin-4-ylmethyl, 1-(2-thiomorpholinoethyl)piperidin-4-ylmethyl, 1-(3-thiomorpholinopropyl)piperidin-4-ylmethyl, 1-(2-azetidinylethyl)piperidin-4-ylmethyl or 1-(3-azetidinylpropyl)piperidin-4-ylmethyl, 3-morpholino-2-hydroxypropyl, (2R)-3-morpholino-2-hydroxypropyl, (2S)-3-morpholino-2-hydroxypropyl, 3-piperidino-2-hydroxypropyl, (2R)-3-piperidino-2-hydroxypropyl, (2S)-3-piperidino-2-hydroxypropyl, 3-pyrrolidin-1-yl-2-hydroxypropyl, (2R)-3-pyrrolidin-1-yl-2-hydroxypropyl, (2S)-3-pyrrolidin-1-yl-2-hydroxypropyl, 3-(1-methylpiperazin-4-yl)-2-hydroxypropyl, (2R)-3-(1-methylpiperazin-4-yl)-2-hydroxypropyl, (2S)-3-(1-methylpiperazin-4-yl)-2-hydroxypropyl, 3-(N,N-diethylamino)-2-hydroxypropyl, (2R)-3-(N,N-diethylamino)-2-hydroxypropyl, (2S)-3-(N,N-diethylamino)-2-hydroxypropyl, 3-(isopropylamino)-2-hydroxypropyl, (2R)-3-(isopropylamino)-2-hydroxypropyl, (2S)-3-(isopropylamino)-2-hydroxypropyl, 3-(N,N-diisopropylamino)-2-hydroxypropyl, (2R)-3-(N,N-diisopropylamino)-2-hydroxypropyl or (2S)-3-(N,N-diisopropylamino)-2-hydroxypropyl].

According to another aspect of the present invention particularly $R^2$ represents $C_{1-3}$alkyl, amino or $R^5X^1$— [wherein $X^1$ is as hereinbefore defined and $R^5$ represents ethyl, benzyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(ethylsulphinyl)ethyl, 2-(ethylsulphonyl)ethyl, 2-(N,N-dimethylsulphamoyl)ethyl, 2-(N-methylsulphamoyl)ethyl, 2-sulphamoylethyl, 2-(methylamino)ethyl, 3-(methylamino)propyl, 2-(ethylamino)ethyl, 3-(ethylamino)propyl, 2-(N,N-dimethylamino)ethyl, 3-(N,N-dimethylamino)propyl, 2-(N,N-diethylamino)ethyl, 3-(N,N-diethylamino)propyl, 2-(N- methyl-N-methylsulphonylamino)ethyl, 3-(N-methyl-N-methylsulphonylamino)propyl, 2-morpholinoethyl, 3-morpholinopropyl, 2-piperidinoethyl, 3-piperidinopropyl, 2-(methylpiperidino)ethyl, 3-(methylpiperidino)propyl, 2-(ethylpiperidino)ethyl, 3-(ethylpiperidino)propyl, 2-((2-methoxyethyl)piperidino)ethyl, 3-((2-methoxyethyl)piperidino)propyl, 2-((2-methylsulphonyl)ethylpiperidino)ethyl, 3-((2-methylsulphonyl)ethylpiperidino)propyl, piperidin-3-ylmethyl, piperidin-4-ylmethyl, 2-(piperidin-3-yl)ethyl, 2-(piperidin-4-yl)ethyl, 3-(piperidin-3-yl)propyl, 3-(piperidin-4-yl)propyl, 2-(piperidin-2-yl)ethyl, 3-(piperidin-2-yl)propyl, (1-methylpiperidin-3-yl)methyl, (1-methylpiperidin-4-yl)methyl, (1-cyanomethylpiperidin-3-yl)methyl, (1-cyanomethylpiperidin-4-yl)methyl, 2-(methylpiperidin-3-yl)ethyl, 2-(methylpiperidin-4-yl)ethyl, 2-(1-cyanomethylpiperidin-3-yl)ethyl, 2-(1-cyanomethylpiperidin-4-yl)ethyl, 3-(methylpiperidin-3-yl)propyl, 3-(methylpiperidin-4-yl)propyl, 3-(1-cyanomethylpiperidin-3-yl)propyl, 3-(1-cyanomethylpiperidin-4-yl)propyl, 2-(ethylpiperidin-3-yl)ethyl, 2-(ethylpiperidin-4-yl)ethyl, 3-(ethylpiperidin-3-yl)propyl, 3-(ethylpiperidin-4-yl)propyl, ((2-methoxyethyl)piperidin-3-yl)methyl, ((2-methoxyethyl)piperidin-4-yl)methyl, 2-((2-methoxyethyl)piperidin-3-yl)ethyl, 2-((2-methoxyethyl)piperidin-4-yl)ethyl, 3-((2-methoxyethyl)piperidin-3-yl)propyl, 3-((2-methoxyethyl)piperidin-4-yl)propyl, (1-(2-methylsulphonylethyl)piperidin-3-yl)methyl, (1-(2-methylsulphonylethyl)piperidin-4-yl)methyl, 2-((2-methylsulphonylethyl)piperidin-3-yl)ethyl, 2-((2-methylsulphonylethyl)piperidin-4-yl)ethyl, 3-((2-methylsulphonylethyl)piperidin-3-yl)propyl, 3-((2-methylsulphonylethyl)piperidin-4-yl)propyl, 1-isopropylpiperidin-2-ylmethyl, 1-isopropylpiperidin-3-ylmethyl, 1-isopropylpiperidin-4-ylmethyl, 2-(1-isopropylpiperidin-2-yl)ethyl, 2-(1-isopropylpiperidin-3-yl)ethyl, 2-(1-isopropylpiperidin-4-yl)ethyl, 3-(1-isopropylpiperidin-2-yl)propyl, 3-(1-isopropylpiperidin-3-yl)propyl, 3-(1-isopropylpiperidin-4-yl)propyl, 2-(piperidin-4-yloxy)ethyl, 3-(piperidin-4-yloxy)propyl, 2-(1-(cyanomethyl)piperidin-4-yloxy)ethyl, 3-(1-(cyanomethyl)piperidin-4-yloxy)propyl, 2-(1-(2-cyanoethyl)piperidin-4-yloxy)ethyl, 3-(1-(2-cyanoethyl)piperidin-4-yloxy)propyl, 2-(piperazin-1-yl)ethyl, 3-(piperazin-1-yl)propyl, (pyrrolidin-2-yl)methyl, 2-(pyrrolidin-1-yl)ethyl, 3-(pyrrolidin-1-yl)propyl, (2-oxo-tetrahydro-2H-pyrrolidin-5-yl)methyl, 5(R)-(2-oxo-tetrahydro-2H-pyrrolidin-5-yl)methyl, (5S)-(2-oxo-tetrahydro-2H-pyrrolidin-5-yl)methyl, (1,3-dioxolan-2-yl)methyl, 2-(1,3-dioxolan-2-yl)ethyl, 2-(2-methoxyethylamino)ethyl, 2-(N-(2-methoxyethyl)-N-methylamino)ethyl, 2-(2-hydroxyethylamino)ethyl, 3-(2-methoxyethylamino)propyl, 3-(N-(2-methoxyethyl)-N-methylamino)propyl, 3-(2-hydroxyethylamino)propyl, 2-methylthiazol-4-ylmethyl, 2-acetamidothiazol-4-ylmethyl, 1-methylimidazol-2-ylmethyl, 2-(imidazol-1-yl)ethyl, 2-(2-methylimidazol-1-yl)ethyl, 2-(2-ethylimidazol-1-yl)ethyl, 3-(2-methylimidazol-1-yl)propyl, 3-(2-ethylimidazol-1-yl)propyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, 2-(4-pyridyloxy)ethyl, 2-(4-pyridylamino)ethyl, 2-(4-oxo-1,4-dihydro-1-pyridyl)ethyl, 2-(2-oxo-imidazolidin-1-yl)ethyl, 3-(2-oxo-imidazolidin-1-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy)ethyl, 2-(4-methylpiperazin-1-yl)ethyl, 3-(4-methylpiperazin-1-yl)propyl, 3-(methylsulphinyl)propyl, 3-(methylsulphonyl)propyl, 3-(ethylsulphinyl)propyl, 3-(ethylsulphonyl)propyl, 2-(5-methyl-1,2,4-triazol-1-yl)ethyl, morpholino, 2-((N-(1-methylimidazol-4-ylsulphonyl)-N-methyl)amino)ethyl, 2-((N-(3-morpholinopropylsulphonyl)-N-methyl)amino) ethyl, 2-((N-methyl-N-4-pyridyl)amino)ethyl, 3-(4-oxidomorpholino)propyl, 2-(2-(4-methylpiperazin-1-yl) ethoxy)ethyl, 3-(2-(4-methylpiperazin-1-yl)ethoxy)propyl, 2-(2-morpholinoethoxy)ethyl, 3-(2-morpholinoethoxy) propyl, 2-(tetrahydropyran-4-yloxy)ethyl, 3-(tetrahydropyran-4-yloxy)propyl, 2-((2-(pyrrolidin-1-yl) ethyl)carbamoyl)vinyl, 3-((2-(pyrrolidin-1-yl)ethyl) carbamoyl)prop-2-en-1-yl, 1-(2-pyrrolidinylethyl)piperidin-4-ylmethyl, 1-(3-pyrrolidinylpropyl)piperidin-4-ylmethyl, 1-(2-piperidinylethyl)piperidin-4-ylmethyl, 1-(3-piperidinylpropyl)piperidin-4-ylmethyl, 1-(2-morpholinoethyl)piperidin-4-ylmethyl, 1-(3-morpholinopropyl)piperidin-4-ylmethyl, 1-(2-thiomorpholinoethyl)piperidin-4-ylmethyl, 1-(3-thiomorpholinopropyl)piperidin-4-ylmethyl, 1-(2-azetidinylethyl)piperidin-4-ylmethyl or 1-(3-azetidinylpropyl)piperidin-4-ylmethyl, 3-morpholino-2-hydroxypropyl, (2R)-3-morpholino-2-hydroxypropyl, (2S)-3-morpholino-2-hydroxypropyl, 3-piperidino-2-hydroxypropyl, (2R)-3-piperidino-2-hydroxypropyl, (2S)-3-piperidino-2-hydroxypropyl, 3-pyrrolidin-1-yl-2-hydroxypropyl, (2R)-3-pyrrolidin 1-yl-2-hydroxypropyl, (2S)-3-pyrrolidin-1-yl-2-hydroxypropyl, 3-(1-methylpiperazin-4-yl)-2-hydroxypropyl, (2R)-3-(1-methylpiperazin-4-yl)-2-hydroxypropyl, (2S)-3-(1-methylpiperazin-4-yl)-2-hydroxypropyl, 3-(N,N-diethylamino)-2-hydroxypropyl, (2R)-3-(N,N-diethylamino)-2-hydroxypropyl, (2S)-3-(N,N-diethylamino)-2-hydroxypropyl, 3-(isopropylamino)-2-hydroxypropyl, (2R)-3-(isopropylamino)-2-hydroxypropyl, (2S)-3-(isopropylamino)-2-hydroxypropyl, 3-(N,N-diisopropylamino)-2-hydroxypropyl, (2R)-3-(N,N-diisopropylamino)-2-hydroxypropyl or (2S)-3-(N,N-diisopropylamino)-2-hydroxypropyl].

According to another aspect of the present invention more particularly $R^2$ represents $C_{1-3}$alkyl, amino or $R^5X^1$—[wherein $X^1$ is as hereinbefore defined and $R^5$ represents ethyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(ethylsulphinyl)ethyl, 2-(ethylsulphonyl)ethyl, 2-(N,N-dimethylsulphamoyl)ethyl, 2-(N-methylsulphamoyl)ethyl, 2-sulphamoylethyl, 2-(methylamino)ethyl, 3-(methylamino) propyl, 2-(ethylamino)ethyl, 3-(ethylamino)propyl, 2-(N,N-dimethylamino)ethyl, 3-(N,N-dimethylamino)propyl, 2-(N,N-diethylamino)ethyl, 3-(N,N-diethylamino)propyl, 2-(N-methyl-N-methylsulphonylamino)ethyl, 3-(N-methyl-N-methylsulphonylamino)propyl, 2-morpholinoethyl, 3-morpholinopropyl, 2-piperidinoethyl, 3-piperidinopropyl, 2-(methylpiperidino)ethyl, 3-(methylpiperidino)propyl, 2-(ethylpiperidino)ethyl, 3-(ethylpiperidino)propyl, 2-((2-methoxyethyl)piperidino)ethyl, 3-((2-methoxyethyl)piperidino)propyl, 2-((2-methylsulphonyl)ethylpiperidino) ethyl, 3-((2-methylsulphonyl)ethylpiperidino)propyl, piperidin-3-ylmethyl, piperidin-4-ylmethyl, 2-(piperidin-3-yl)ethyl, 2-(piperidin-4-yl)ethyl, 3-(piperidin-3-yl)propyl, 3-(piperidin-4-yl)propyl, 2-(piperidin-2-yl)ethyl, 3-(piperidin-2-yl)propyl, (1-methylpiperidin-3-yl)methyl, (1-methylpiperidin-4-yl)methyl, (1-cyanomethylpiperidin-3-yl)methyl, (1-cyanomethylpiperidin-4-yl)methyl, 2-(methylpiperidin-3-yl)ethyl, 2-(methylpiperidin-4-yl) ethyl, 2-(1-cyanomethylpiperidin-3-yl)ethyl, 2-(1-cyanomethylpiperidin-4-yl)ethyl, 3-(methylpiperidin-3-yl)

propyl, 3-(methylpiperidin-4-yl)propyl, 3-(1-cyanomethylpiperidin-3-yl)propyl, 3-(1-cyanomethylpiperidin-4-yl)propyl, 2-(ethylpiperidin-3-yl)ethyl, 2-(ethylpiperidin-4-yl)ethyl, 3-(ethylpiperidin-3-yl)propyl, 3-(ethylpiperidin-4-yl)propyl, ((2-methoxyethyl)piperidin-3-yl)methyl, ((2-methoxyethyl)piperidin-4-yl)methyl, 2-((2-methoxyethyl)piperidin-3-yl)ethyl, 2-((2-methoxyethyl)piperidin-4-yl)ethyl, 3-((2-methoxyethyl)piperidin-3-yl)propyl, 3-((2-methoxyethyl)piperidin-4-yl)propyl, (1-(2-methylsulphonylethyl)piperidin-3-yl)methyl, (1-(2-methylsulphonylethyl)piperidin-4-yl)methyl, 2-((2-methylsulphonylethyl)piperidin-3-yl)ethyl, 2-((2-methylsulphonylethyl)piperidin-4-yl)ethyl, 3-((2-methylsulphonylethyl)piperidin-3-yl)propyl, 3-((2-methylsulphonylethyl)piperidin-4-yl)propyl, 1-isopropylpiperidin-2-ylmethyl, 1-isopropylpiperidin-3-ylmethyl, 1-isopropylpiperidin-4-ylmethyl, 2-(1-isopropylpiperidin-2-yl)ethyl, 2-(1-isopropylpiperidin-3-yl)ethyl, 2-(1-isopropylpiperidin-4-yl)ethyl, 3-(1-isopropylpiperidin-2-yl)propyl, 3-(1-isopropylpiperidin-3-yl)propyl, 3-(1-isopropylpiperidin-4-yl)propyl, 2-(piperidin-4-yloxy)ethyl, 3-(piperidin-4-yloxy)propyl, 2-(1-(cyanomethyl)piperidin-4-yloxy)ethyl, 3-(1-(cyanomethyl)piperidin-4-yloxy)propyl, 2-(1-(2-cyanoethyl)piperidin-4-yloxy)ethyl, 3-(1-(2-cyanoethyl)piperidin-4-yloxy)propyl, 2-piperazin-1-yl)ethyl, 3-(piperazin-1-yl)propyl, (pyrrolidin-2-yl)methyl, 2-(pyrrolidin-1-yl)ethyl, 3-(pyrrolidin-1-yl)propyl, (2-oxo-tetrahydro-2H-pyrrolidin-5-yl)methyl, 5(R)-(2-oxo-tetrahydro-2H-pyrrolidin-5-yl)methyl, (5S)-(2-oxo-tetrahydro-2H-pyrrolidin-5-yl)methyl, (1,3-dioxolan-2-yl)methyl, 2-(1,3-dioxolan-2-yl)ethyl, 2-(2-methoxyethylamino)ethyl, 2-(N-(2-methoxyethyl)-N-methylamino)ethyl, 2-(2-hydroxyethylamino)ethyl, 3-(2-methoxyethylamino)propyl, 3-(N-(2-methoxyethyl)-N-methylamino)propyl, 3-(2-hydroxyethylamino)propyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, 2-(4-pyridyloxy)ethyl, 2-(4-pyridylamino)ethyl, 2-(4-oxo-1,4-dihydro-1-pyridyl)ethyl, 2-(2-oxo-imidazolidin-1-yl)ethyl, 3-(2-oxo-imidazolidin-1-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy)ethyl, 2-(4-methylpiperazin-1-yl)ethyl, 3-(4-methylpiperazin-1-yl)propyl, 3-(methylsulphinyl)propyl, 3-(methylsulphonyl)propyl, 3-(ethylsulphinyl)propyl, 3-(ethylsulphonyl)propyl, 2-(5-methyl-1,2,4-triazol-1-yl)ethyl, morpholino, 2-((N-(3-morpholinopropylsulphonyl)-N-methyl)amino)ethyl, 2-((N-methyl-N-4-pyridyl)amino)ethyl, 3-(4-oxidomorpholino)propyl, 2-(2-(4-methylpiperazin-1-yl)ethoxy)ethyl, 3-(2-(4-methylpiperazin-1-yl)ethoxy)propyl, 2-(2-morpholinoethoxy)ethyl, 3-(2-morpholinoethoxy)propyl, 2-(tetrahydropyran-4-yloxy)ethyl, 3-(tetrahydropyran-4-yloxy)propyl, 2-((2-(pyrrolidin-1-yl)ethyl)carbamoyl)vinyl, 3-((2-(pyrrolidin-1-yl)ethyl)carbamoyl)prop-2-en-1-yl, 1-(2-pyrrolidinylethyl)piperidin-4-ylmethyl, 1-(3-pyrrolidinylpropyl)piperidin-4-ylmethyl, 1-(2-piperidinylethyl)piperidin-4-ylmethyl, 1-(3-piperidinylpropyl)piperidin-4-ylmethyl, 1-(2-morpholinoethyl)piperidin-4-ylmethyl, 1-(3-morpholinopropyl)piperidin-4-ylmethyl, 1-(2-thiomorpholinoethyl)piperidin-4-ylmethyl, 1-(3-thiomorpholinopropyl)piperidin-4-ylmethyl, 1-(2-azetidinylethyl)piperidin-4-ylmethyl or 1-(3-azetidinylpropyl)piperidin-4-ylmethyl, 3-morpholino-2-hydroxypropyl, (2R)-3-morpholino-2-hydroxypropyl, (2S)-3-morpholino-2-hydroxypropyl, 3-piperidino-2-hydroxypropyl, (2R)-3-piperidino-2-hydroxypropyl, (2R)-3-piperidino-2-hydroxypropyl, 3-pyrrolidin-1-yl-2-hydroxypropyl, (2R)-3-pyrrolidin-1-yl-2-hydroxypropyl, (2S)-3-pyrrolidin-1-yl-2-hydroxypropyl, 3-(1-methylpiperazin-4-yl)-2-hydroxypropyl, (2R)-3-(1-methylpiperazin-4-yl)-2-hydroxypropyl, (2S)-3-(1-methylpiperazin-4-yl)-2-hydroxypropyl, 3-(N,N-diethylamino)-2-hydroxypropyl, (2R)-3-(N,N-diethylamino)-2-hydroxypropyl, (2S)-3-(N,N-diethylamino)-2-hydroxypropyl, 3-(isopropylamino)-2-hydroxypropyl, (2R)-3-(isopropylamino)-2-hydroxypropyl, (2S)-3-(isopropylamino)-2-hydroxypropyl, 3-(N,N-diisopropylamino)-2-hydroxypropyl, (2R)-3-(N,N-diisopropylamino)-2-hydroxypropyl or (2S)-3-(N,N-diisopropylamino)-2-hydroxypropyl].

In another aspect $R^2$ represents ethoxy, trifluoromethoxy, 2,2,2-trifluoroethoxy, 2-hydroxyethoxy, 3-hydroxypropoxy, 2-methoxyethoxy, 3-methoxypropoxy, 2-(methylsulphinyl)ethoxy, 2-(methylsulphonyl)ethoxy, 2-(ethylsulphinyl)ethoxy, 2-(ethylsulphonyl)ethoxy, 2-(N,N-dimethylsulphamoyl)ethoxy, 2-(4-methylsulphamoyl)ethoxy, 2-sulphamoylethoxy, 2-(methylamino)ethoxy, 3-(methylamino)propoxy, 2-(ethylamino)ethoxy, 3-(ethylamino)propoxy, 2-(N,N-dimethylamino)ethoxy, 3-(N,N-dimethylamino)propoxy, 2-(N,N-diethylamino)ethoxy, 3-(N,N-diethylamino)propoxy, 2-(N-methyl-N-methylsulphonylamino)ethoxy, 3-(N-methyl-N-methylsulphonylamino)propoxy, 2-morpholinoethoxy, 3-morpholinopropoxy, 2-piperidinoethoxy, 3-piperidinopropoxy, 2-(methylpiperidino)ethoxy, 3-(methylpiperidino)propoxy, 2-(ethylpiperidino)ethoxy, 3-(ethylpiperidino)propoxy, 2-((2-methoxyethyl)piperidino)ethoxy, 3-((2-methoxyethyl)piperidino)propoxy, 2-((2-methylsulphonyl)ethylpiperidino)ethoxy, 3-((2-methylsulphonyl)ethylpiperidino)propoxy, piperidin-3-ylmethoxy, piperidin-4-ylmethoxy, 2-(piperidin-3-yl)ethoxy, 2-(piperidin-4-yl)ethoxy, 3-(piperidin-3-yl)propoxy, 3-(piperidin-4-yl)propoxy, 2-(piperidin-2-yl)ethoxy, 3-(piperidin-2-yl)propoxy, (1-methylpiperidin-3-yl)methoxy, (1-methylpiperidin-4-yl)methoxy, (1-cyanomethylpiperidin-3-yl)methoxy, (1-cyanomethylpiperidin-4-yl)methoxy, 2-(methylpiperidin-3-yl)ethoxy, 2-(methylpiperidin-4-yl)ethoxy, 2-(1-cyanomethylpiperidin-3-yl)ethoxy, 2-(1-cyanomethylpiperidin-4-yl)ethoxy, 3-(methylpiperidin-3-yl)propoxy, 3-(methylpiperidin-4-yl)propoxy, 3-(1-cyanomethylpiperidin-3-yl)propoxy, 3-(1-cyanomethylpiperidin-4-yl)propoxy, 2-(ethylpiperidin-3-yl)ethoxy, 2-(ethylpiperidin-4-yl)ethoxy, 3-(ethylpiperidin-3-yl)propoxy, 3-(ethylpiperidin-4-yl)propoxy, ((2-methoxyethyl)piperidin-3-yl)methoxy, ((2-methoxyethyl)piperidin-4-yl)methoxy, 2-((2-methoxyethyl)piperidin-3-yl)ethoxy, 2-((2-methoxyethyl)piperidin-4-yl)ethoxy, 3-((2-methoxyethyl)piperidin-3-yl)propoxy, 3-((2-methoxyethyl)piperidin-4-yl)propoxy, (1-(2-methylsulphonylethyl)piperidin-3-yl)methoxy, (1-(2-methylsulphonylethyl)piperidin-4-yl)methoxy, 2-((2-methylsulphonylethyl)piperidin-3-yl)ethoxy, 2-((2-methylsulphonylethyl)piperidin-4-yl)ethoxy, 3-((2-methylsulphonylethyl)piperidin-3-yl)propoxy, 3-((2-methylsulphonylethyl)piperidin-4-yl)propoxy, 1-isopropylpiperidin-2-ylmethoxy, 1-isopropylpiperidin-3-ylmethoxy, 1-isopropylpiperidin-4-ylmethoxy, 2-(1-isopropylpiperidin-2-yl)ethoxy, 2-(1-isopropylpiperidin-3-yl)ethoxy, 2-(1-isopropylpiperidin-4-yl)ethoxy, 3-(1-isopropylpiperidin-2-yl)propoxy, 3-(1-isopropylpiperidin-3-yl)propoxy, 3-(1-isopropylpiperidin-4- yl)propoxy, 2-(piperidin-4-yloxy)ethoxy, 3-(piperidin-4-yloxy)propoxy, 2-(1-(cyanomethyl)piperidin-4-yloxy) ethoxy, 3-(1-(cyanomethyl)piperidin-4-yloxy)propoxy, 2-(1-(2-cyanoethyl)piperidin-4-yloxy)ethoxy, 3-(1-(2-cyanoethyl)piperidin-4-yloxy)propoxy, 2-(piperazin-1-yl) ethoxy, 3-(piperazin-1-yl)propoxy, (pyrrolidin-2-yl) methoxy, 2-(pyrrolidin-1-yl)ethoxy, 3-(pyrrolidin-1-yl) propoxy, (2-oxo-tetrahydro-2H-pyrrolidin-5-yl)methoxy, 5(R)-(2-oxo-tetrahydro-2H-pyrrolidin-5-yl)methoxy, (5S)-(2-oxo-tetrahydro-2H-pyrrolidin-5-yl)methoxy, (1,3-dioxolan-2-yl)methoxy, 2-(1,3-dioxolan-2-yl)ethoxy, 2-(2-methoxyethylamino)ethoxy, 2-(N-(2-methoxyethyl)-N-methylamino)ethoxy, 2-(2-hydroxyethylamino)ethoxy, 3-(2-methoxyethylamino)propoxy, 3-(N-(2-methoxyethyl)-N-methylamino)propoxy, 3-(2-hydroxyethylamino)propoxy, 2-(1,2,3-triazol-1-yl)ethoxy, 2-(1,2,3-triazol-2-yl)ethoxy, 2-(1,2,4-triazol-1-yl)ethoxy, 2-(1,2,4-triazol-4-yl)ethoxy, 4-pyridylmethoxy, 2-(4-pyridyl)ethoxy, 3-(4-pyridyl) propoxy, 2-(4-pyridyloxy)ethoxy, 2-(4-pyridylamino) ethoxy, 2-(4-oxo-1,4-dihydro-1-pyridyl)ethoxy, 2-(2-oxo-imidazolidin-1-yl)ethoxy, 3-(2-oxo-imidazolidin-1-yl) propoxy, 2-thiomorpholinoethoxy, 3-thiomorpholinopropoxy, 2-(1,1-dioxothiomorpholino) ethoxy, 3-(1,1-dioxothiomorpholino)propoxy, 2-(2-methoxyethoxy)ethoxy, 2-(4-methylpiperazin-1-yl)ethoxy, 3-(4-methylpiperazin-1-yl)propoxy, 3-(methylsulphinyl) propoxy, 3-(methylsulphonyl)propoxy, 3-(ethylsulphinyl) propoxy, 3-(ethylsulphonyl)propoxy, 2-(5-methyl-1,2,4-triazol-1-yl)ethoxy, 2-((N-(3-morpholinopropylsulphonyl)-N-methyl)amino)ethoxy, 2-((N-methyl-N-4-pyridyl)amino) ethoxy, 3-(4-oxidomorpholino)propoxy, 2-(2-(4-methylpiperazin-1-yl)ethoxy)ethoxy, 3-(2-(4-methylpiperazin-1-yl)ethoxy)propoxy, 2-(2-morpholinoethoxy)ethoxy, 3-(2-morpholinoethoxy) propoxy, 2-(tetrahydropyran-4-yloxy)ethoxy, 3-(tetrahydropyran-4-yloxy)propoxy, 2-((2-(pyrrolidin-1-yl) ethyl)carbamoyl)vinyl, 3-((2-(pyrrolidin-1-yl)ethyl) carbamoyl)prop-2-en-1-yloxy, 1-(2-pyrrolidinylethyl) piperidin-4-ylmethoxy, 1-(3-pyrrolidinylpropyl)piperidin-4-ylmethoxy, 1-(2-piperidinylethyl)piperidin-4-ylmethoxy, 1-(3-piperidinylpropyl)piperidin-4-ylmethoxy, 1-(2-morpholinoethyl)piperidin-4-ylmethoxy, 1-(3-morpholinopropyl)piperidin-4-ylmethoxy, 1-(2-thiomorpholinoethyl)piperidin-4-ylmethoxy, 1-(3-thiomorpholinopropyl)piperidin-4-ylmethoxy, 1-(2-azetidinylethyl)piperidin-4-ylmethoxy, 1-(3-azetidinylpropyl)piperidin-4-ylmethoxy, 3-morpholino-2-hydroxypropoxy, (2R)-3-morpholino-2-hydroxypropoxy, (2S)-3-morpholino-2-hydroxypropoxy, 3-piperidino-2-hydroxypropoxy, (2R)-3-piperidino-2-hydroxypropoxy, (2S)-3-piperidino-2-hydroxypropoxy, 3-pyrrolidin-1-yl-2-hydroxypropoxy, (2R)-3-pyrrolidin-1-yl-2-hydroxypropoxy, (2S)-3-pyrrolidin-1-yl-2-hydroxypropoxy, 3-(1-methylpiperazin-4-yl)-2-hydroxypropoxy, (2R)-3-(1-methylpiperazin-4-yl)-2-hydroxypropoxy, (2, S)-3-(1-methylpiperazin-4-yl)-2-hydroxypropoxy, 3-(N,N-diethylamino)-2-hydroxypropoxy, (2R)-3-(N,N-diethylamino)-2-hydroxypropoxy, (2S)-3-(N,N-diethylamino)-2-hydroxypropoxy, 3-(isopropylamino)-2-hydroxypropoxy, (2R)-3-(isopropylamino)-2-hydroxypropoxy, (2S)-3-(isopropylamino)-2-hydroxypropoxy, 3-(N,N-diisopropylamino)-2-hydroxypropoxy, (2R)-3-(N,N-diisopropylamino)-2-hydroxypropoxy or (2S)-3-(N,N-diisopropylamino)-2-hydroxypropoxy.

Where one of the $R^2$ substituents is $R^5X^1$— the substituent $R^5X^1$— is preferably at the 5- or 7-position of the cinnoline ring, more preferably at the 7-position of the cinnoline ring.

When one of the $R^2$ substituents is at the 6-position of the cinnoline ring it is preferably hydrogen, halogeno, $C_{1-3}$alkyl, trifluoromethyl, cyano, $C_{1-3}$alkoxy, $C_{1-3}$alkylsulphanyl or —$NR^3R^4$ (wherein $R^3$ and $R^4$ are as defined hereinbefore).

When one of the $R^2$ substituents is at the 6-position of the cinnoline ring it is more preferably hydrogen, $C_{1-3}$alkoxy, cyano, trifluoromethyl, $C_{1-3}$alkylsulphanyl, fluoro, chloro, bromo or nitro.

When one of the $R^2$ substituents is at the 6-position of the cinnoline ring it is particularly hydrogen, methoxy or cyano.

When one of the $R^2$ substituents is at the 6-position of the cinnoline ring it is especially methoxy.

In another aspect of the present invention there is provided the use of compounds of the formula Ia:

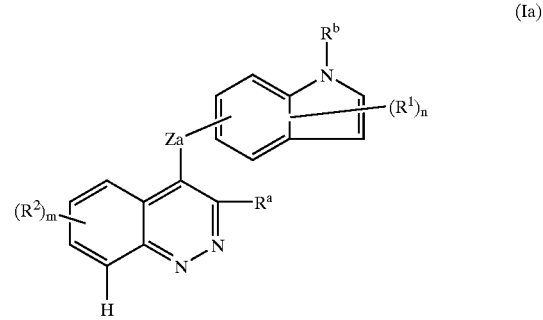

(Ia)

wherein
$R^a$, $R^b$, $R^1$, $R^2$, n and m are as defined hereinbefore and Za represents —O—, —NH— or —S—;
or a salt thereof, or a prodrug thereof for example an ester or an amide, in the manufacture of a medicament for use in the production of an antiangiogenic and/or vascular permeability reducing effect in warm-blooded animals such as humans.

In a further aspect of the present invention there is provided the use of compounds of the formula Ib:

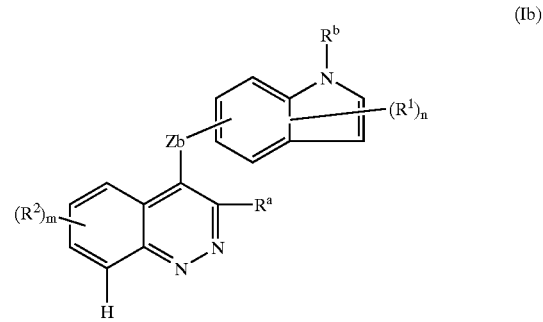

(Ib)

wherein $R^a$, $R^b$, $R^1$, $R^2$, n and m are as defined hereinbefore and Zb represents —O— or —NH—;
or a salt thereof, or a prodrug thereof for example an ester or an amide, in the manufacture of a medicament for use in the production of an antiangiogenic and/or vascular permeability reducing effect in warm-blooded animals such as humans.

In a further aspect of the present invention there is provided the use of compounds of the formula Ib as defined hereinbefore, with the proviso that $R^2$ at the 7-position of the cinnoline ring cannot have any value selected from hydrogen, methyl, methoxy and chloro; or a salt thereof, or a prodrug thereof for example an ester or an amide, in the manufacture of a medicament for use in the production of an antiangiogenic and/or vascular permeability reducing effect in warm-blooded animals such as humans.

According to another aspect of the present invention there is provided a compound of the formula I as defined hereinbefore and salts thereof, and prodrugs thereof for example esters, amides and sulphides, preferably esters and amides.

According to another aspect of the present invention there is provided a compound of the formula $I^1$ as defined hereinbefore and salts thereof, and prodrugs thereof for example esters, amides and sulphides, preferably esters and amides.

According to another aspect of the present invention there is provided a compound of the formula Ia as defined hereinbefore and salts thereof, and prodrugs thereof for example esters, amides and sulphides, preferably esters and amides.

According to another aspect of the present invention there is provided a compound of the formula Ib as defined hereinbefore and salts thereof, and prodrugs thereof for example esters, amides and sulphides, preferably esters and amides.

According to another aspect of the present invention there is provided a compound of the formula Ib as defined hereinbefore with the proviso that $R^2$ at the 7-position of the cinnoline ring cannot have any value selected from hydrogen, methyl, methoxy and chloro; and salts thereof, and prodrugs thereof for example esters, anodes and sulphides, preferably esters and amides.

Preferred compounds of the present invention include
4-(4-fluoro-2-methylindol-5-yloxy)-6-methoxy-7-(3-(pyrrolidin-1-yl)propoxy)cinnoline,
7-(3-(1,1-dioxothiomorpholino)propoxy)-4-(4-fluoro-2-methylindol-5-yloxy)-6-methoxycinnoline,
4-(4-fluoro-2-methylindol-5-yloxy)-7-(R)-(2-hydroxy-3-(piperidin-1-yl)propoxy)-6-methoxycinnoline, and
4-(4-fluoro-2-methylindol-5-yloxy)-6-methoxy-7-(piperidin-4-ylmethoxy)cinnoline, and salts thereof.

More preferred compounds of the present invention include
4-(4-fluoro-2-methylindol-5-yloxy)-6-methoxy-7-(3-(pyrrolidin-1-yl)propoxy)cinnoline,
4-(4-fluoro-2-methylindol-5-yloxy)-6-methoxy-7-(piperidin-4-ylmethoxy)cinnoline,
4-(4-fluoro-2-methylindol-5-yloxy)-7-(R)-(2-hydroxy-3-(piperidin-1-yl)propoxy)-6-methoxycinnoline,
4-(4-fluoro-2-methylindol-5-yloxy)-6-methoxy-7-(1-methylpiperidin-4-ylmethoxy)cinnoline,
7-benzyloxy-4-(4-fluoro-2-methylindol-5-yloxy)-6-methoxycinnoline,
4-(4-fluoro-2-methylindol-5-yloxy)-7-(R)-(2-hydroxy-3-pyrrolidin-1-yl)propoxy)-6-methoxycinnoline,
4-(4-fluoro-2-methylindol-5-yl)oxy-6-methoxy-7-(3-(4-methylpiperazin-1-yl)propoxy)cinnoline,
4-(4-fluoro-2-methylindol-5-yloxy)-6-methoxy-7-(3-(piperidin-1-yl)propoxy)cinnoline, and salts thereof.

For the avoidance of doubt it is to be understood that where in this specification a group is qualified by 'hereinbefore defined' or 'defined hereinbefore' the said group encompasses the first occurring and broadest definition as well as each and all of the preferred definitions for that group.

In this specification unless stated otherwise the term "alkyl" includes both straight and branched chain alkyl groups but references to individual alkyl groups such as "propyl" are specific for the straight chain version only. An analogous convention applies to other generic terms. Unless otherwise stated the term "alkyl" advantageously refers to chains with 1–6 carbon atoms, preferably 1–4 carbon atoms.

The term "alkoxy" as used herein, unless stated otherwise includes "alkyl" —O— groups in which "alkyl" is as hereinbefore defined. The term "aryl" as used herein unless stated otherwise includes reference to a $C_{6-10}$ aryl group which may, if desired, carry one or more substituents selected from halogeno, alkyl, alkoxy, nitro, trifluoromethyl and cyano, (wherein alkyl and alkoxy are as hereinbefore defined). The term "aryloxy" as used herein unless otherwise stated includes "aryl" —O— groups in which "aryl" is as hereinbefore defined. The term "sulphonyloxy" as used herein refers to alkylsulphonyloxy and arylsulphonyloxy groups in which "alkyl" and "aryl" are as hereinbefore defined. The term "alkanoyl" as used herein unless otherwise stated includes formyl and alkylC=O groups in which "alkyl" is as defined hereinbefore, for example $C_2$alkanoyl is ethanoyl and refers to $CH_3C$=O, $C_1$alkanoyl is formyl and refers to CHO. In this specification unless stated otherwise the term "alkenyl" includes both straight and branched chain alkenyl groups but references to individual alkenyl groups such as 2-butenyl are specific for the straight chain version only. Unless otherwise stated the term "alkenyl" advantageously refers to chains with 2–5 carbon atoms, preferably 3–4 carbon atoms. In this specification unless stated otherwise the term "alkynyl" includes both straight and branched chain alkynyl groups but references to individual alkynyl groups such as 2-butynyl are specific for the straight chain version only. Unless otherwise stated the term "alkynyl" advantageously refers to chains with 2–5 carbon atoms, preferably 3–4 carbon atoms. Unless stated otherwise the term "haloalkyl" refers to an alkyl group as defined hereinbefore which bears one or more halogeno groups, such as for example trifluoromethyl.

For the avoidance of any doubt, where $R^2$ has a value of substituted or unsubstituted $C_{1-5}$alkyl, $R^2$ has been selected from $C_{1-3}$alkyl or from a group $R^5X^1$ wherein $X^1$ is a direct bond or —$CH_2$— and $R^5$ is $C_{1-5}$alkyl which may be unsubstituted or which may be substituted with one or more groups selected from hydroxy, fluoro, chloro, bromo and amino.

Within the present invention it is to be understood that a compound of the formula I or a salt thereof may exhibit the phenomenon of tautomerism and that the formulae drawings within this specification can represent only one of the possible tautomeric forms. It is to be understood that the invention encompasses any tautomeric form which inhibits VEGF receptor tyrosine kinase activity and is not to be limited merely to any one tautomeric form utilised within the formulae drawings. The formulae drawings within this specification can represent only one of the possible tautomeric forms and it is to be understood that the specification encompasses all possible tautomeric forms of the compounds drawn not just those forms which it has been possible to show graphically herein.

It will be appreciated that compounds of the formula I or a salt thereof may possess an asymmetric carbon atom. Such an asymmetric carbon atom is also involved in the tautomerism described above, and it is to be understood that the present invention encompasses any chiral form (including both pure enantiomers, scalemic and racemic mixtures) as well as any tautomeric form which inhibits VEGF receptor tyrosine kinase activity, and is not to be limited merely to any one tautomeric form or chiral form utilised within the formulae drawings. It is to be understood that the invention encompasses all optical and diastereomers which inhibit VEGF receptor tyrosine kinase activity. It is further to be understood that in the names of chiral compounds (R,S) denotes any scalemic or racemic mixture while (R) and (S)

denote the enantiomers. In the absence of (R,S), (R) or (S) in the name it is to be understood that the name refers to any scalemic or racemic mixture, wherein a scalemic mixture contains R and S enantiomers in any relative proportions and a racemic mixture contains R and S enantiomers in the ration 50:50.

It is also to be understood that certain compounds of the formula I and salts thereof can exist in solvated as well as unsolvated forms such as, for example, hydrated forms. It is to be understood that the invention encompasses all such solvated forms which inhibit VEGF receptor tyrosine kinase activity.

For the avoidance of any doubt, it is to be understood that when $X^1$ is, for example, a group of formula —$NR^6C(O)$—, it is the nitrogen atom bearing the $R^6$ group which is attached to the cinnoline ring and the carbonyl (C(O)) group is attached to $R^5$, whereas when $X^1$ is, for example, a group of formula —$C(O)NR^7$—, it is the carbonyl group which is attached to the cinnoline ring and the nitrogen atom bearing the $R^7$ group is attached to $R^5$. A similar convention applies to the other two atom $X^1$ linking groups such as —$NR^9SO_2$— and —$SO_2NR^8$—. When $X^1$ is —$NR^{10}$— it is the nitrogen atom bearing the $R^{10}$ group which is linked to the cinnoline ring and to $R^5$. An analogous convention applies to other groups. It is further to be understood that when $X^1$ represents —$NR^{10}$— and $R^{10}$ is $C_{1-3}$alkoxy$C_{2-3}$alkyl it is the $C_{2-3}$alkyl moiety which is linked to the nitrogen atom of $X^1$ and an analogous convention applies to other groups.

For the avoidance of any doubt, it is to be understood that in a compound of the formula I when $R^5$ is, for example, a group of formula $C_{1-3}$alkyl$X^9C_{1-3}$alkyl$R^{29}$, it is the terminal $C_{1-3}$alkyl moiety which is linked to $X^1$, similarly when $R^5$ is, for example, a group of formula $C_{2-5}$alkenyl$R^{28}$ it is the $C_{2-5}$alkenyl moiety which is linked to $X^1$ and an analogous convention applies to other groups. When $R^5$ is a group 1-$R^{29}$prop-1-en-3-yl it is the first carbon to which the group $R^{29}$ is attached and it is the third carbon which is linked to $X^1$ and an analogous convention applies to other groups.

For the avoidance of any doubt, it is to be understood that in a compound of the formula I when $R^5$ is, for example, $R^{28}$ and $R^{28}$ is a pyrrolidinyl ring which bears a group —(—O—)$_f$(C$_{1-4}$alkyl)$_g$ringD, it is the —O— or C$_{1-4}$alkyl which is linked to the pyrrolidinyl ring, unless f and g are both 0 when it is ring D which is linked to the pyrrolidinyl ring and an analogous convention applies to other groups.

For the avoidance of any doubt, it is to be understood that when $R^{29}$ carries a $C_{1-4}$aminoalkyl substituent it is the $C_{1-4}$alkyl moiety which is attached to $R^{29}$ whereas when $R^{29}$ carries a $C_{1-4}$alkylamino substituent it is the amino moiety which is attached to $R^{29}$ and an analogous convention applies to other groups.

For the avoidance of any doubt, it is to be understood that when $R^{28}$ carries a $C_{1-4}$alkoxy$C_{1-4}$alkyl substituent it is the $C_{1-4}$alkyl moiety which is attached to $R^{28}$ and an analogous convention applies to other groups.

For the avoidance of any doubt, it is to be understood that when $R^1$ is —$C_{1-5}$alkyl(ring B) it is the alkyl chain which is linked to the indole group and ring B is attached to the alkyl chain and an analogous convention applies to other groups.

For the avoidance of any doubt, it is to be understood that when $R^b$ is $C_{2-5}$alkenylamino$C_{1-4}$alkyl, it is the $C_{1-4}$alkyl group which is linked to the nitrogen atom of the 5-membered ring and an analogous convention applies to other groups.

The present invention relates to the compounds of formula I as hereinbefore defined as well as to the salts thereof.

Salts for use in pharmaceutical compositions will be pharmaceutically acceptable salts, but other salts may be useful in the production of the compounds of formula I and their pharmaceutically acceptable salts. Pharmaceutically acceptable salts of the invention may, for example, include acid addition salts of the compounds of formula I as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid of which hydrochloric acid is particularly preferred) or with sulphuric or phosphoric acid, or with trifluoroacetic, citric or maleic acid. In addition where the compounds of formula I are sufficiently acidic, pharmaceutically acceptable salts may be formed with an inorganic or organic base which affords a pharmaceutically acceptable cation. Such salts with inorganic or organic bases include for example an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl)amine.

A compound of the formula I, or salt thereof, and other compounds of the invention (as hereinafter defined) may be prepared by any process known to be applicable to the preparation of chemically-related compounds. Such processes include, for example, those illustrated in International Patent Application Publication No. WO 97/34876 and in International Patent Application Publication No. WO 00/47212 (Application No. PCT/GB00/00373). Such processes also include, for example, solid phase synthesis. Such processes, are provided as a further feature of the invention and are as described hereinafter. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

Thus, the following processes (a) to (f) and (i) to (vi) constitute further features of the present invention.

Synthesis of Compounds of Formula I (a) Compounds of the formula I and salts thereof may be prepared by the reaction of a compound of the formula III:

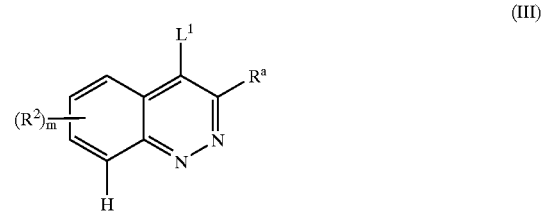

(III)

(wherein $R^a$, $R^2$ and m are as defined hereinbefore and $L^1$ is a displaceable moiety), with a compound of the formula IV:

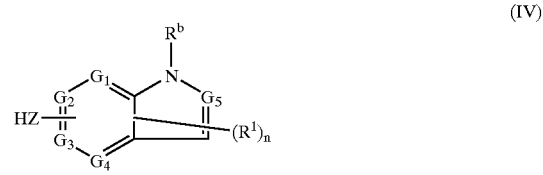

(IV)

(wherein $R^b$, $R^1$, $G_1$, $G_2$, $G_3$, $G_4$, $G_5$, Z and n are as defined hereinbefore) to obtain compounds of the formula I and salts thereof. A convenient displaceable moiety $L^1$ is, for example, a halogeno, alkoxy (preferably $C_{1-4}$alkoxy), aryloxy, alkylsulphanyl, arylsulphanyl, alkoxyalkylsulphanyl or sulphonyloxy group, for example a chloro, bromo, methoxy, phenoxy, methylsulphanyl, 2-methoxyethylsulphanyl, methanesulphonyloxy or toluene-4-sulphonyloxy group.

The reaction is advantageously effected in the presence of a base. When Z is —O— such a base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, tetramethylguanidine or for example, an alkali metal or alkaline earth metal carbonate or hydroxide, for example sodium carbonate, potassium carbonate, cesium carbonate, calcium carbonate, sodium hydroxide or potassium hydroxide. Alternatively such a base is, for example, an alkali metal hydride, for example sodium hydride, or an alkali metal or alkaline earth metal amide, for example sodium amide, sodium bis(trimethylsilyl)amide, potassium amide or potassium bis(trimethylsilyl)amide. The reaction is preferably effected in the presence of an inert solvent or diluent, for example an ether such as tetrahydrofuran or 1,4-dioxan, an aromatic hydrocarbon solvent such as toluene, or a dipolar aprotic solvent such as N,N-dimethylformamide, N,N-dimethylacetamide, N-methylpyrrolidin-2-one or dimethyl sulphoxide. The reaction is conveniently effected at a temperature in the range, for example, 10 to 150° C., preferably in the range 20 to 110° C.

When Z is —NH— the reaction is advantageously effected in the presence of either an acid or a base. Such an acid is for example, an anhydrous inorganic acid such as hydrochloric acid, in the presence of a protic solvent or diluent, for example an alcohol or ester such as methanol, ethanol, 2-propanol, 2-pentanol.

When it is desired to obtain the acid salt, the free base may be treated with an acid such as a hydrogen halide, for example hydrogen chloride, sulphuric acid, a sulphonic acid, for example methane sulphonic acid, or a carboxylic acid, for example acetic or citric acid, using a conventional procedure.

(b) Production of those compounds of formula I and salts thereof wherein at least one $R^2$ is $R^5X^1$ wherein $R^5$ is as defined hereinbefore and $X^1$ is —O—, —S—, —OC(O)— or —NR$^{10}$— (wherein $R^{10}$ independently represents hydrogen, $C_{1-3}$alkyl or $C_{1-3}$alkoxy$C_{2-3}$alkyl) can be achieved by the reaction, conveniently in the presence of a base (as defined hereinbefore in process (a)) of a compound of the formula V:

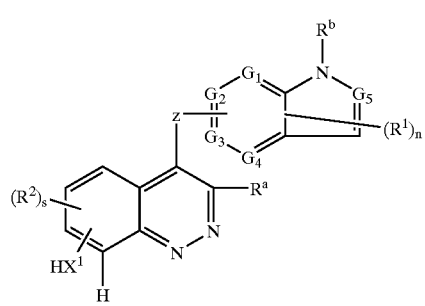

(V)

(wherein $R^a$, $R^b$, Z, $G_1$, $G_2$, $G_3$, $G_4$, $G_5$, $R^1$, $R^2$ and n are as hereinbefore defined and $X^1$ is as hereinbefore defined in this section and s is an integer from 0 to 2) with a compound of formula VI:

$R^5$-$L^1$ (VI)

(wherein $R^5$ and $L^1$ are as hereinbefore defined), $L^1$ is a displaceable moiety for example a halogeno or sulphonyloxy group such as a bromo, methanesulphonyloxy or toluene-4-sulphonyloxy group, or $L^1$ may be generated in situ from an alcohol under standard Mitsunobu conditions ("Organic Reactions", John Wiley & Sons Inc, 1992, vol 42, chapter 2, David L Hughes). The reaction is preferably effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 50° C.

(c) Compounds of the formula I and salts thereof wherein at least one $R^2$ is $R^5X^1$ wherein $R^5$ is as defined hereinbefore and $X^1$ is —O—, —S—, —OC(O)— or —NR$^{10}$— (wherein $R^{10}$ represents hydrogen, $C_{1-3}$alkyl or $C_{1-3}$alkoxy$C_{2-3}$alkyl) may be prepared by the reaction of a compound of the formula VII:

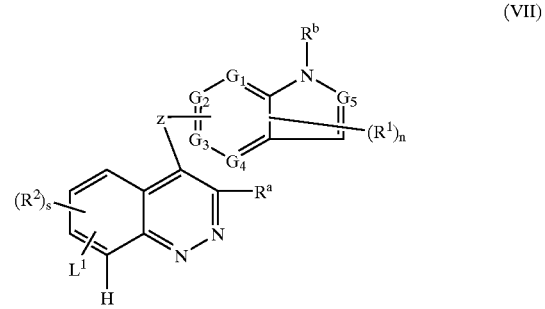

(VII)

with a compound of the formula VIII:

$R^5$—$X^1$—H (VIII)

(wherein $L^1$, $R^a$, $R^b$, $R^1$, $R^2$, $R^5$, $G_1$, $G_2$, $G_3$, $G_4$, $G_5$, Z, n and s are all as hereinbefore defined and $X^1$ is as hereinbefore defined in this section). The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 100° C.

(d) Compounds of the formula I and salts thereof wherein at least one $R^2$ is $R^5X^1$ wherein $X^1$ is as defined hereinbefore and $R^5$ is $C_{1-5}$alkyl$R^{62}$, wherein $R^{62}$ is selected from one of the following nine groups:

1) $X^{10}C_{1-3}$alkyl (wherein $X^{10}$ represents —O—, —S—, —SO$_2$—, —NR$^{63}$C(O)— or —NR$^{64}$SO$_2$— (wherein $R^{63}$ and $R^{64}$ which maybe the same or different are each hydrogen, $C_{1-3}$alkyl or $C_{1-3}$alkoxy$C_{2-3}$alkyl);

2) NR$^{65}$R$^{66}$ (wherein $R^{65}$ and $R^{66}$ which may be the same or different are each hydrogen, $C_{1-3}$alkyl or $C_{1-3}$alkoxy$C_{2-3}$alkyl);

3) $X^{11}C_{1-5}$alkyl$X^5R^{22}$ (wherein $X^{11}$ represents —O—, —S—, —SO$_2$—, —NR$^{67}$C(O)—, —NR$^{68}$SO$_2$— or —NR$^{69}$ (wherein $R^{67}$, $R^{68}$, and $R^{69}$ which may be the same or different are each hydrogen, $C_{1-3}$alkyl or $C_{1-3}$alkoxy$C_{2-3}$alkyl) and $X^5$ and $R^{22}$ are as defined hereinbefore);

4) $R^{28}$ (wherein $R^{28}$ is as defined hereinbefore);

5) $X^{12}R^{29}$ (wherein $X^{12}$ represents —O—, —S—, —SO$_2$—, —NR$^{70}$C(O)—, —NR$^{71}$SO$_2$—, or —NR$^{72}$— (wherein $R^{70}$, $R^{71}$, and $R^{72}$ which may be the same or different are each hydrogen, $C_{1-3}$alkyl or $C_{1-3}$alkoxy$C_{2-3}$alkyl) and $R^{29}$ is as defined hereinbefore); and 6) $X^{13}C_{1-3}$alkyl$R^{29}$ (wherein $X^{13}$ represents —O—, —S—, —SO$_2$—, —NR$^{73}$C(O)—, —NR$^{74}$SO$_2$— or —NR$^{75}$—

(wherein $R^{73}$, $R^{74}$ and $R^{75}$ each independently represents hydrogen, $C_{1-3}$alkyl or $C_{1-3}$alkoxy$C_{2-3}$alkyl) and $R^{29}$ is as defined hereinbefore);

7) $R^{29}$ (wherein $R^{29}$ is as defined hereinbefore);
8) $X^{13}C_{1-4}$alkyl$R^{28}$ (wherein $X^{13}$ and $R^{28}$ are as defined hereinbefore); and
9) $R^{54}(C_{1-4}$alkyl$)_q(X^9)'R^{55}$ (wherein q, r, $X^9$, $R^{54}$ and $R^{55}$ are as defined hereinbefore); may be prepared by reacting a compound of the formula IX:

(IX)

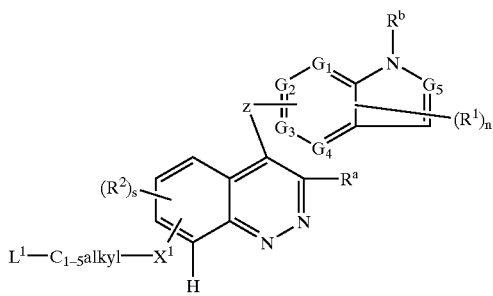

(wherein $L^1$, $X^1$, $R^a$, $R^b$, $R^1$, $R^2$, $G_1$, $G_2$, $G_3$, $G_4$, $G_5$, Z, n and s are as hereinbefore defined) with a compound of the formula X:

$$R^{62}-H \quad (X)$$

(wherein $R^{62}$ is as defined hereinbefore) to give a compound of the formula I or salt thereof. The reaction may conveniently be effected in the presence of a base (as defined hereinbefore in process (a)) and advantageously in the presence of an inert solvent or diluent (as defined hereinbefore in process (a)), and at a temperature in the range, for example 0 to 150° C., conveniently at about 50° C.

Processes (a) and (b) are preferred over processes (c) and (d).

Process (a) is preferred over processes (b), (c) and (d).

(e) The production of those compounds of the formula I and salts thereof wherein one or more of the substituents $(R^2)_m$ is represented by —$NR^{76}R^{77}$ where one (and the other is hydrogen) or both of $R^{76}$ and $R^{77}$ are $C_{1-3}$alkyl, may be effected by the reaction of compounds of formula I wherein the substituent $(R^2)_m$ is an amino group and an alkylating agent, preferably in the presence of a base as defined hereinbefore. Such alkylating agents are $C_{1-3}$alkyl moieties bearing a displaceable moiety as defined hereinbefore such as $C_{1-3}$alkyl halides for example $C_{1-3}$alkyl chloride, bromide or iodide. The reaction is preferably effected in the presence of an inert solvent or diluent (as defined hereinbefore in process (a)) and at a temperature in the range, for example, 10 to 100° C., conveniently at about ambient temperature. The production of compounds of formula I and salts thereof wherein one or more of the substituents $R^2$ is an amino group may be effected by the reduction of a corresponding compound of formula I wherein the substituent(s) at the corresponding position(s) of the cinnoline group is/are a nitro group(s). The reduction may conveniently be effected as described in process (i) hereinafter. The production of a compound of formula I and salts thereof wherein the substituent(s) at the corresponding position(s) of the cinnoline group is/are a nitro group(s) maybe effected by the processes described hereinbefore and hereinafter in processes (a–d) and (i–v) using a compound selected from the compounds of the formulae (I–XXII) in which the substituent(s) at the corresponding position(s) of the cinnoline group is/are a nitro group(s).

(f) Compounds of the formula I and salts thereof wherein $X^1$ is —SO— or —$SO_2$— may be prepared by oxidation from the corresponding compound in which $X^1$ is —S— or —SO— (when $X^1$ is —$SO_2$— is required in the final product). Conventional oxidation conditions and reagents for such reactions are well known to the skilled chemist.

Synthesis of Intermediates (i) The compounds of formula III and salts thereof in which $L^1$ is halogeno may for example be prepared by halogenating a compound of the formula XI:

(XI)

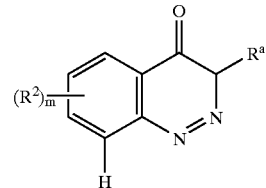

wherein $R^1$, $R^2$ and m are as hereinbefore defined).

Convenient halogenating agents include inorganic acid halides, for example thionyl chloride, phosphorus(III) chloride, phosphorus(V)oxychloride and phosphorus(V) chloride. The halogenation reaction may be effected in the presence of an inert solvent or diluent such as for example a halogenated solvent such as methylene chloride, trichloromethane or carbon tetrachloride, or an aromatic hydrocarbon solvent such as benzene or toluene, or the reaction may be effected without the presence of a solvent. The reaction is conveniently effected at a temperature in the range, for example 10 to 150° C., preferably in the range 40 to 100° C.

The compounds of formula XI and salts thereof may, for example, be prepared by reacting a compound of the formula XII:

(XII)

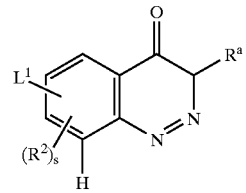

(wherein $R^a$, $R^2$, s and $L^1$ are as hereinbefore defined) with a compound of the formula VIII as hereinbefore defined. The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 110° C.

The compounds of formula XI and salts thereof may also be prepared by cyclising a compound of the formula XIII:

(XIII)

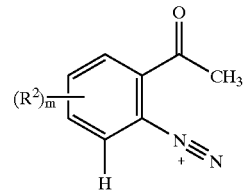

(wherein $R^2$ and m are as hereinbefore defined) whereby to form a compound of formula XI or salt thereof. The cyclisation may be conveniently effected in the presence of a mineral or organic acid, for example sulphuric acid, hydrochloric acid or acetic acid or a mixture thereof, preferably at a temperature in the range 20° C. to 100° C., especially 50–80° C. or if desired under pH-controlled conditions, advantageously at a pH of 4.0 to 8.5. Preferably the pH of the solution is maintained within the range of 6.5 to 8.0. The desired pH is conveniently obtained by the use of an inert base or by the use of an aqueous solution of such a base. Bases which may be used include alkali metal bicarbonates, carbonates or hydroxides or organic amines such as for example pyridine or tertiary amines such as triethylamine, diisopropylethylamine, 2,6-lutidine, collidine, 4-dimethylaminopyridine or methylmorpholine [for example as described in U.S. Pat. No. 4,620,000 (L. R. Denes) or DD 258809 (Hirsch et al.)]

The compounds of formula XIII and salts thereof, may for example be prepared by diazotisation of a compound of the formula XV:

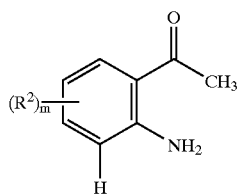

(XIV)

(wherein $R^2$ and m are as hereinbefore defined). The diazotisation is conveniently effected by the use of an alkali metal nitrite, such as sodium nitrite, in the presence of a mineral acid such as hydrochloric or sulphuric acid or in the presence of an organic acid such as acetic acid or in the presence of a mixture of such acids. The diazotisation is advantageously effected at a temperature in the range between the freezing point of the reaction mixture and 20° C., preferably from 0 to 20° C.

Preferably the compounds of formula XI are prepared by diazotisation and in situ cyclisation of the resulting compound of formula XIII for example as described by Borsch W. and Herbert A. Annalen der Chemie, Volume 546, p293–303.

Compounds of formula XIV and salts thereof, may for example be prepared by reduction of the nitro group in a compound of formula XV:

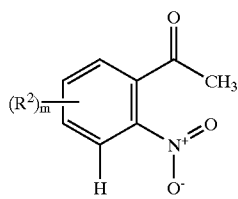

(XV)

(wherein $R^2$ and m are as hereinbefore defined) to yield a compound of formula XIV as hereinbefore defined or salt thereof. The reduction of the nitrogroup may conveniently be effected by any of the procedures known for such a transformation. The reduction may be carried out, for example, by the hydrogenation of a solution of the nitro compound in the presence of an inert solvent or diluent as defined hereinbefore in the presence of a metal effective to catalyse hydrogenation reactions such as palladium or platinum. A further reducing agent is, for example, an activated metal such as activated iron (produced for example by washing iron powder with a dilute solution of an acid such as hydrochloric acid). Thus, for example, the reduction may be effected by heating the nitro compound and the activated metal in the presence of a solvent or diluent such as a mixture of water and alcohol, for example methanol or ethanol, to a temperature in the range, for example 50 to 150° C., conveniently at about 70° C.

Where the reduction is effected in the presence of activated iron, this is advantageously produced in situ, conveniently by the use of iron, generally iron powder, in the presence of acetic acid/water and preferably at about 100° C.

The compounds of formula XV and salts thereof may for example be produced by reacting a compound of formula XVI:

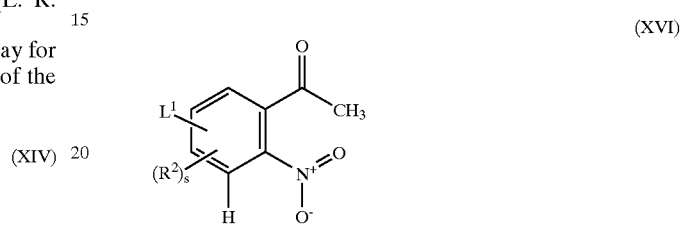

(XVI)

(wherein $R^2$, s and $L^1$ are as hereinbefore defined) with a compound of formula VIII as hereinbefore defined to yield a compound of formula XV as hereinbefore defined or salt thereof. The reaction of the compounds of formula XVI and VIII is conveniently effected under conditions as described for process (c) hereinbefore.

Compounds of formula XVI and salts thereof may for example be prepared by nitration of a compound of the formula XVII:

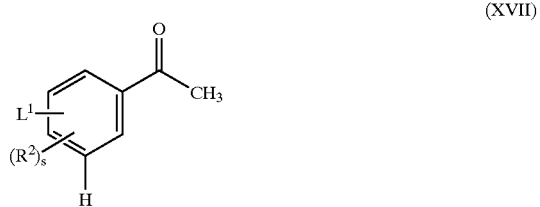

(XVII)

(wherein $R^2$, s and $L^1$ are as hereinbefore defined) whereby to form a compound of formula XVII as hereinbefore defined or a salt thereof. The nitration is conveniently effected in the presence of nitric acid which may be dilute or concentrated, but is preferably about 70% nitric acid. The nitration is conveniently effected at a temperature in the range 0 to 20° C. The nitration may also be effected in the presence of a Lewis acid catalyst such as tin(IV)chloride. Where a Lewis acid catalyst is used the reaction is advantageously effected at a lower temperature, conveniently in the range −50 to 0° C., preferably at about −30° C., preferably in the presence of methylene chloride.

The compounds of formula XV, as defined hereinbefore, and salts thereof may for example be prepared by nitration of compounds of the formula XVII in which the $L^1$ moiety is replaced by $R^2$. The nitration is conveniently effected as described hereinbefore.

The compounds of formula XII, as defined hereinbefore, and salts thereof may for example be prepared from compounds of the formulae XIII and XIV, in which the $R^2$ group(s) is/are replaced by the moiety $L^1$, the reactions may be effected by processes as described above for the preparation of compounds of formula XI from compounds of formulae XIII and XIV. Compounds of the formula XIV in which the $R^2$ group is replaced by the moiety $L^1$ may be prepared by the reduction of the nitro group in compounds of the formula XVI, the reduction may be effected as defined hereinbefore.

The compounds of formula III and salts thereof wherein at least one $R^2$ is $R^5X^1$ and wherein $X^1$ is —O—, —S—, —SO$_2$—, —OC(O)—, —C(O)NR$^7$—, —SO$_2$NR$^8$— or —NR$^{10}$— (wherein $R^7$, $R^8$ and $R^{10}$ each independently represents hydrogen, $C_{1-3}$alkyl or $C_{1-3}$alkoxy$C_{2-3}$alkyl), may also be prepared for example by reacting a compound of the formula XVIII:

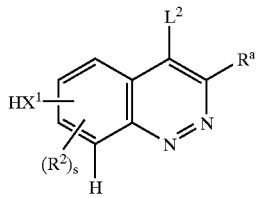

(XVIII)

(wherein $R^a$, $R^2$ and s are as hereinbefore defined, $X^1$ is as hereinbefore defined in this section and $L^2$ represents a displaceable protecting moiety) with a compound of the formula VI as hereinbefore defined, whereby to obtain a compound of formula III in which $L^1$ is represented by $L^2$.

A compound of formula XVIII is conveniently used in which $L^2$ represents a chloro group or a phenoxy group which may if desired carry up to 5 substituents, preferably up to 2 substituents, selected from halogeno, nitro and cyano. The reaction may be conveniently effected under conditions as described for process (b) hereinbefore.

The compounds of formula XVIII and salts thereof may for example be prepared by deprotecting a compound of the formula XIX:

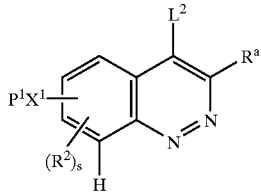

(XIX)

(wherein $R^a$, $R^2$, s and $L^2$ are as hereinbefore defined, $P^1$ is a protecting group and $X^1$ is as hereinbefore defined in the section describing compounds of the formula XVIII). The choice of protecting group $P^1$ is within the standard knowledge of an organic chemist, for example those included in standard texts such as "Protective Groups in Organic Synthesis" T. W. Greene and R. G. M. Wuts, 2nd Ed. Wiley 1991, including N-sulphonyl derivatives (for example, p-toluenesulphonyl), carbamates (for example, t-butyl carbonyl), N-alkyl derivatives (for example, 2-chloroethyl, benzyl) and amino acetal derivatives (for example benzyloxymethyl). The removal of such a protecting group may be effected by any of the procedures known for such a transformation, including those reaction conditions indicated in standard texts such as that indicated hereinbefore, or by a related procedure. Deprotection may be effected by techniques well known in the literature, for example where $P^1$ represents a benzyl group deprotection may be effected by hydrogenolysis or by treatment with trifluoroacetic acid.

One compound of formula III may if desired be converted into another compound of formula III in which the moiety $L^1$ is different. Thus for example a compound of formula III in which $L^1$ is other than halogeno, for example optionally substituted phenoxy, may be converted to a compound of formula III in which $L^1$ is halogeno by hydrolysis of a compound of formula III (in which $L^1$ is other than halogeno) to yield a compound of formula XI as hereinbefore defined, followed by introduction of halide to the compound of formula XI, thus obtained as hereinbefore defined, to yield a compound of formula II in which $L^1$ represents halogen.

(ii) Compounds of formula IV may be prepared by any of the methods known in the art, such as for example those described in "Indoles Part I", "Indoles Part II", 1972 John Wiley & Sons Ltd and "Indoles Part III" 1979, John Wiley & Sons Ltd, edited by W. J. Houlihan. Compounds of formula IV may be prepared by any of the methods described in the Examples hereinafter.

Compounds of formula IV may be prepared by any of the processes described in International Patent Application Publication No. WO 00/47212, the entire content of which is included herein by reference, with particular reference to the processes described in WO 00/47212 in Examples 48, 182 237, 242, 250 and 291 therein.

For example the azaindole 2-methyl-1H-pyrrolo[2,3-b]pyridin-5-ol, may be prepared according to the method described in Reference Example 1 hereinafter.

(iii) Compounds of formula V as hereinbefore defined and salts thereof may be made by deprotecting the compound of formula XX:

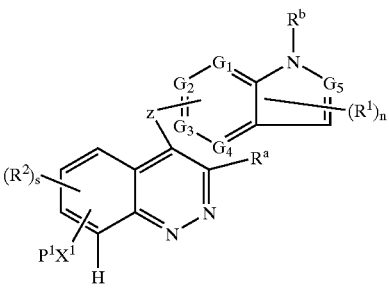

(XX)

(wherein $R^a$, $R^b$, Z, $R^1$, $R^2$, $G_1$, $G_2$, $G_3$, $G_4$, $G_5$, $P^1$, n and s are as hereinbefore defined and $X^1$ is as hereinbefore defined in the section describing compounds of the formula V) by a process for example as described in (i) above.

Compounds of the formula XX and salts thereof may be made by reacting compounds of the formulae XIX and IV as hereinbefore defined, under the conditions described in (a) hereinbefore, to give a compound of the formula XX or salt thereof.

(iv) Compounds of the formula VII and salts thereof may be made by reacting a compound of the formula XXI:

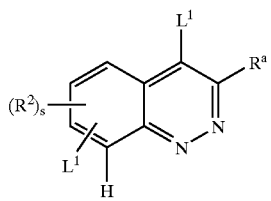

(XXI)

(wherein $R^a$, $R^2$, s and each $L^1$ are as hereinbefore defined and the $L^1$ in the 4-position and the other $L^1$ in a further position on the cinnoline ring may be the same or different)

with a compound of the formula IV as hereinbefore defined, the reaction for example being effected by a process as described in (a) above.

(v) Compounds of formula IX as defined hereinbefore and salts thereof may for example be made by the reaction of compounds of formula V as defined hereinbefore with compounds of the formula XXII:

$$L^1\text{-}C_{1\text{-}5}\text{alkyl-}L^1 \qquad (XXII)$$

(wherein $L^1$ is as hereinbefore defined) to give compounds of formula IX or salts thereof. The reaction may be effected for example by a process as described in (b) above.

(vi) Intermediate compounds wherein $X^1$ is —SO— or —SO$_2$— may be prepared by oxidation from the corresponding compound in which $X^1$ is —S— or —SO— (when $X^1$ is —SO$_2$— is required in the final product). Conventional oxidation conditions and reagents for such reactions are well known to the skilled chemist.

When a pharmaceutically acceptable salt of a compound of the formula I is required, it may be obtained, for example, by reaction of said compound with, for example, an acid using a conventional procedure, the acid having a pharmaceutically acceptable anion.

Many of the intermediates defined herein, for example, those of the formulae IV, V, VII, IX and XX are novel and these are provided as a further feature of the invention. The preparation of these compounds is as described herein and/or is by methods well known to persons skilled in the art of organic chemistry.

The identification of compounds which potently inhibit the tyrosine kinase activity associated with VEGF receptors such as Flt and/or KDR and which inhibit angiogenesis and/or increased vascular permeability is desirable and is the subject of the present invention. These properties may be assessed, for example, using one or more of the procedures set out below:

(a) In Vitro Receptor Tyrosine Kinase Inhibition Test

This assay determines the ability of a test compound to inhibit tyrosine kinase activity. DNA encoding VEGF, FGF or EGF receptor cytoplasmic domains may be obtained by total gene synthesis (Edwards M, International Biotechnology Lab 5(3), 19–25, 1987) or by cloning. These may then be expressed in a suitable expression system to obtain polypeptide with tyrosine kinase activity. For example VEGF, FGF and EGF receptor cytoplasmic domains, which were obtained by expression of recombinant protein in insect cells, were found to display intrinsic tyrosine kinase activity. In the case of the VEGF receptor Flt (Genbank accession number X51602), a 1.7 kb DNA fragment encoding most of the cytoplasmic domain, commencing with methionine 783 and including the termination codon, described by Shibuya et al (Oncogene, 1990, 5: 519–524), was isolated from cDNA and cloned into a baculovirus transplacement vector (for example pAcYM1 (see The Baculovirus Expression System: A Laboratory Guide, L. A. King and R. D. Possee, Chapman and Hall, 1992) or pAc360 or pBlueBacHis (available from Invitrogen Corporation)). This recombinant construct was co-transfected into insect cells (for example *Spodoptera frugiperda* 21 (Sf21)) with viral DNA (eg Pharmingen BaculoGold) to prepare recombinant baculovirus. (Details of the methods for the assembly of recombinant DNA molecules and the preparation and use of recombinant baculovirus can be found in standard texts for example Sambrook et al, 1989, Molecular cloning—A Laboratory Manual, 2nd edition, Cold Spring Harbour Laboratory Press and O'Reilly et al, 1992, Baculovirus Expression Vectors—A Laboratory Manual, W. H. Freeman and Co, New York). For other tyrosine kinases for use in assays, cytoplasmic fragments starting from methionine 806 (KDR, Genbank accession number L04947), methionine 668 (EGF receptor, Genbank accession number X00588) and methionine 399 (FGF R1 receptor, Genbank accession number X51803) may be cloned and expressed in a similar manner.

For expression of cFlt tyrosine kinase activity, Sf21 cells were infected with plaque-pure cFlt recombinant virus at a multiplicity of infection of 3 and harvested 48 hours later. Harvested cells were washed with ice cold phosphate buffered saline solution (PBS) (10 mM sodium phosphate pH7.4, 138 mM sodium chloride, 2.7 mM potassium chloride) then resuspended in ice cold HNTG/PMSF (20 mM Hepes pH7.5, 150 mM sodium chloride, 10% V/V glycerol, 1% v/v Triton X100, 1.5 mM magnesium chloride, 1M ethylene glycol-bis(βaminoethyl ether) N,N,N',N'-tetraacetic acid (EGTA), 1 mM PMSF (phenylmethylsulphonyl fluoride); the PMSF is added just before use from a freshly-prepared 100 mM solution in methanol) using 1 ml HNTG/PMSF per 10 million cells. The suspension was centrifuged for 10 minutes at 13,000 rpm at 4° C., the supernatant (enzyme stock) was removed and stored in aliquots at −70° C. Each new batch of stock enzyme was titrated in the assay by dilution with enzyme diluent (100 MM Hepes pH 7.4, 0.2 mM sodium orthovanadate, 0.1% v/v Triton X100, 0.2 mM dithiothreitol). For a typical batch, stock enzyme is diluted 1 in 2000 with enzyme diluent and 50 µl of dilute enzyme is used for each assay well.

A stock of substrate solution was prepared from a random copolymer containing tyrosine, for example Poly (Glu, Ala, Tyr) 6:3:1 (Sigma P3899), stored as 1 mg/ml stock in PBS at −20° C. and diluted 1 in 500 with PBS for plate coating.

On the day before the assay 100 µl of diluted substrate solution was dispensed into all wells of assay plates (Nunc maxisorp 96-well immunoplates) which were sealed and left overnight at 4° C.

On the day of the assay the substrate solution was discarded and the assay plate wells were washed once with PBST (PBS containing 0.05% v/v Tween 20) and once with 50 mM Hepes pH7.4.

Test compounds were diluted with 10% dimethylsulphoxide (DMSO) and 25 µl of diluted compound was transferred to wells in the washed assay plates. "Total" control wells contained 10% DMSO instead of compound. Twenty five microlitres of 40 mM manganese(II)chloride containing 8 µM adenosine-5'-triphosphate (ATP) was added to all test wells except "blank" control wells which contained manganese(II)chloride without ATP. To start the reactions 50 µl of freshly diluted enzyme was added to each well and the plates were incubated at room temperature for 20 minutes. The liquid was then discarded and the wells were washed twice with PBST. One hundred microlitres of mouse IgG anti-phosphotyrosine antibody (Upstate Biotechnology Inc. product 05-321), diluted 1 in 6000 with PBST containing 0.5% w/v bovine serum albumin (BSA), was added to each well and the plates were incubated for 1 hour at room temperature before discarding the liquid and washing the wells twice with PBST. One hundred microlitres of horse radish peroxidase (HRP)-linked sheep anti-mouse Ig antibody (Amersham product NXA 931), diluted 1 in 500 with PBST containing 0.5% w/v BSA, was added and the plates were incubated for 1 hour at room temperature before discarding the liquid and washing the wells twice with PBST. One hundred microlitres of 2,2'-azino-bis(3-ethylbenzthiazoline-6-sulphonic acid) (ABTS) solution, freshly prepared using one 50 mg ABTS tablet (Boehringer 1204 521) in 50 ml freshly prepared 50 mM phosphate-citrate buffer pH5.0+0.03% sodium perborate (made with 1 phosphate citrate buffer with sodium perborate (PCSB) capsule (Sigma P4922) per 100 ml distilled water), was added to each well. Plates were then incubated for 20–60 minutes at room temperature until the optical density value of the "total" control wells, measured at 405 nm using a plate reading spectrophotometer, was approximately 1.0. "Blank" (no ATP) and "total" (no compound) control values were used to determine the dilution range of test compound which gave 50% inhibition of enzyme activity.

(b) In Vitro HUVEC Proliferation Assay

This assay determines the ability of a test compound to inhibit the growth factor-stimulated proliferation of human umbilical vein endothelial cells (HUVEC).

HUVEC cells were isolated in MCDB 131 (Gibco BRL) +7.5% v/v foetal calf serum (FCS) and were plated out (at passage 2 to 8), in MCDB 131+2% v/v FCS+3 $\mu$g/ml heparin+1 $\mu$g/ml hydrocortisone, at a concentration of 1000 cells/well in 96 well plates. After a minimum of 4 hours they were dosed with the appropriate growth factor (i.e. VEGF 3 ng/ml, EGF 3 ng/ml or b-FGF 0.3 ng/ml) and compound. The cultures were then incubated for 4 days at 37° C. with 7.5% $CO_2$. On day 4 the cultures were pulsed with 1 $\mu$Ci/well of tritiated-thymidine (Amersham product TRA 61) and incubated for 4 hours. The cells were harvested using a 96-well plate harvester (Tomtek) and then assayed for incorporation of tritium with a Beta plate counter. Incorporation of radioactivity into cells, expressed as cpm, was used to measure inhibition of growth factor-stimulated cell proliferation by compounds.

(c) In Vivo Solid Tumour Disease Model

This test measures the capacity of compounds to inhibit solid tumour growth.

CaLu-6 tumour xenografts were established in the flank of female athymic Swiss nu/nu mice, by subcutaneous injection of $1\times10^6$ CaLu-6 cells/mouse in 100 $\mu$l of a 50% (v/v) solution of Matrigel in serum free culture medium. Ten days after cellular implant, mice were allocated to groups of 8–10, so as to achieve comparable group mean volumes. Tumours were measured using vernier calipers and volumes were calculated as: $(l\times w)\times\sqrt{(l\times w)}\times(\pi/6)$, where l is the longest diameter and w the diameter perpendicular to the longest. Test compounds were administered orally once daily for a minimum of 21 days, and control animals received compound diluent. Tumours were measured twice weekly. The level of growth inhibition was calculated by comparison of the mean tumour volume of the control group versus the treatment group using a Student T test and/or a Mann-Whitney Rank Sum Test. The inhibitory effect of compound treatment was considered significant when $p<0.05$.

According to a further aspect of the invention there is provided a pharmaceutical composition which comprises a compound of the formula I as defined hereinbefore or a pharmaceutically acceptable salt thereof, in association with a pharmaceutically acceptable excipient or carrier.

The composition may be in a form suitable for oral administration, for example as a tablet or capsule, for parenteral injection (including intravenous, subcutaneous, intramuscular, intravascular or infusion) for example as a sterile solution, suspension or emulsion, for topical administration for example as an ointment or cream or for rectal administration for example as a suppository. In general the above compositions may be prepared in a conventional manner using conventional excipients.

The compositions of the present invention are advantageously presented in unit dosage form. The compound will normally be administered to a warm-blooded animal at a unit dose within the range 5–5000 mg per square meter body area of the animal, i.e. approximately 0.1–100 mg/kg. A unit dose in the range, for example, 1–100 mg/kg, preferably 1–50 mg/kg is envisaged and this normally provides a therapeutically-effective dose. A unit dose form such as a tablet or capsule will usually contain, for example 1–250 mg of active ingredient.

According to a further aspect of the present invention there is provided a compound of the formula I or a pharmaceutically acceptable salt thereof as defined hereinbefore for use in a method of treatment of the human or animal body by therapy.

We have found that compounds of the present invention inhibit VEGF receptor tyrosine kinase activity and are therefore of interest for their antiangiogenic effects and/or their ability to cause a reduction in vascular permeability.

A further feature of the present invention is a compound of formula I, or a pharmaceutically acceptable salt thereof, for use as a medicament, conveniently a compound of formula I, or a pharmaceutically acceptable salt thereof, for use as a medicament for producing an antiangiogenic and/or vascular permeability reducing effect in a warm-blooded animal such as a human being.

Thus according to a further aspect of the invention there is provided the use of a compound of the formula I, or a pharmaceutically acceptable salt thereof in the manufacture of a medicament for use in the production of an antiangiogenic and/or vascular permeability reducing effect in a warm-blooded animal such as a human being.

According to a further feature of the invention there is provided a method for producing an antiangiogenic and/or vascular permeability reducing effect in a warm-blooded animal, such as a human being, in need of such treatment which comprises administering to said animal an effective amount of a compound of formula I or a pharmaceutically acceptable salt thereof as defined hereinbefore.

As stated above the size of the dose required for the therapeutic or prophylactic treatment of a particular disease state will necessarily be varied depending on the host treated, the route of administration and the severity of the illness being treated. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

The antiangiogenic and/or vascular permeability reducing treatment defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the antiangiogenic and/or vascular permeability reducing treatment defined hereinbefore may be: surgery, radiotherapy or chemotherapy. Such chemotherapy may cover three main categories of therapeutic agent:

(i) other antiangiogenic agents that work by different mechanisms from those defined hereinbefore (for example linomide, inhibitors of integrin $\alpha v\beta 3$ function, angiostatin, razoxin, thalidomide), and including vascular targeting agents (for example combretastatin phosphate and the vascular damaging agents described in International Patent Application Publication No. WO 99/02166 the entire disclosure of which document is incorporated herein by reference, (for example N-acetylcolchinol-O-phosphate), and in International Patent Application Publication No. WO 00/40529 the entire disclosure of which document is incorporated herein by reference);

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincristine and taxoids like taxol, taxotere); topoisomerase inhibitors (for example epipodophyllotoxins like etoposide and teniposide, amsacrine, topotecan, and also irinotecan); also enzymes (for example asparaginase); and thymidylate synthase inhibitors (for example raltitrexed);

and additional types of chemotherapeutic agent include:
(iv) biological response modifiers (for example interferon); and
(v) antibodies (for example edrecolomab).

For example such conjoint treatment may be achieved by way of the simultaneous, sequential or separate administration of a compound of formula I as defined hereinbefore, and a vascular targeting agent described in WO 99/02166 such as N-acetylcolchinol-O-phosphate (Example 1 of WO 99/02166).

As stated above the compounds defined in the present invention are of interest for their antiangiogenic and/or vascular permeability reducing effects. Such compounds of the invention are expected to be useful in a wide range of disease states including cancer, diabetes, psoriasis, rheumatoid arthritis, Kaposi's sarcoma, haemangioma, acute and chronic nephropathies, atheroma, arterial restenosis, autoimmune diseases, acute inflammation, excessive scar formation and adhesions, lynmphoedema, endometriosis, dysfunctional uterine bleeding and ocular diseases with retinal vessel proliferation. In particular such compounds of the invention are expected to slow advantageously the growth of primary and recurrent solid tumours of, for example, the colon, breast, prostate, lungs and skin. More particularly such compounds of the invention are expected to inhibit the growth of those primary and recurrent solid tumours which are associated with VEGF, especially those tumours which are significantly dependent on VEGF for their growth and spread, including for example, certain tumours of the colon, breast, prostate, lung, vulva and skin.

In addition to their use in therapeutic medicine, the compounds of formula I and their pharmaceutically acceptable salts are also useful as pharmacological tools in the development and standardisation of in vitro and in vivo test systems for the evaluation of the effects of inhibitors of VEGF receptor tyrosine kinase activity in laboratory animals such as cats, dogs, rabbits, monkeys, rats and mice, as part of the search for new therapeutic agents.

It is to be understood that where the term "ether" is used anywhere in this specification it refers to diethyl ether.

The invention will now be illustrated in the following non-limiting Examples in which, unless otherwise stated:

(i) evaporations were carried out by rotary evaporation in vacuo and work-up procedures were carried out after removal of residual solids such as drying agents by filtration;

(ii) operations were carried out at ambient temperature, that is in the range 18–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) melting points are uncorrected and were determined using a Mettler SP62 automatic melting point apparatus, an oil-bath apparatus or a Koffler hot plate apparatus.

(vi) the structures of the end-products of the formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;

(vii) intermediates were not generally fully characterised and purity was assessed by thin layer chromatography (TLC), high-performance liquid chromatography (HPLC), infra-red (IR) or NMR analysis;

(viii) HPLC were run under 2 different conditions:
1) on a TSK Gel super ODS 2 $\mu$M 4.6 mm×5 cm column, eluting with a gradient of methanol in water (containing 1% acetic acid) 20 to 100% in 5 minutes. Flow rate 1.4 ml/minute. Detection: U.V. at 254 nm and light scattering detections;
2) on a TSK Gel super ODS 2 $\mu$M 4.6 mm×5 cm column, eluting with a gradient of methanol in water (containing 1% acetic acid) 0 to 100% in 7 minutes. Flow rate 1.4 ml/minute. Detection: U.V. at 254 nm and light scattering detections.

(ix) petroleum ether refers to that fraction boiling between 40–60° C.

(x) the following abbreviations have been used:
DMF N,N-dimethylformamide
DMSO dimethylsulphoxide
TFA trifluoroacetic acid
NMP 1-methyl-2-pyrrolidinone
THF tetrahydrofuran
HMDS 1,1,1,3,3,3-hexamethyldisilazane.

HPLC RT HPLC retention time
DEAD diethyl azodicarboxylate
DMA dimethylacetamide
DMAP 4-dimethylaminopyridine

EXAMPLE 1

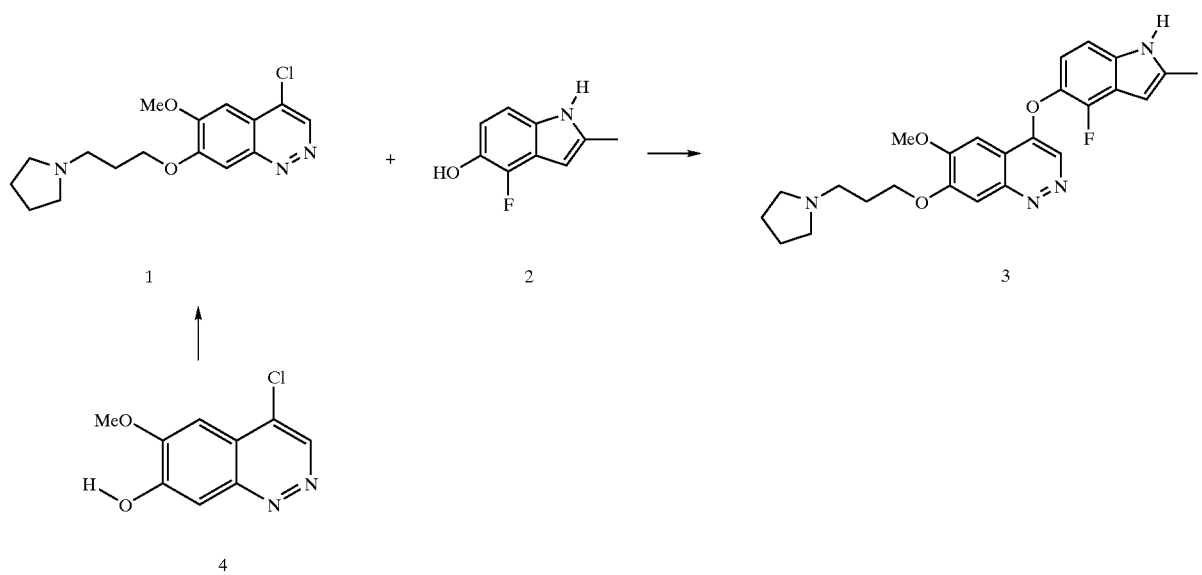

A suspension of 4-chloro-6-methoxy-7-(3-(pyrrolidin-1-yl)propoxy)cinnoline (60 mg, 0.187 mmol), 4-fluoro-5-hydroxy-2-methylindole (46 mg, 0.28 mmol) and cesium carbonate (121 mg, 0.37 mmol) in DMA (2 ml) was heated at 100° C. for 2 hours. The volatiles were removed under vacuum and the residue was purified by column chromatography eluting with methanol/methylene chloride (5/95) followed by methanol saturated with ammonia/methylene chloride (5/95). The fractions containing the expected product were combined and evaporated. The residue was triturated with a mixture of pentane/ether. The solid was filtered, washed with pentane and dried under vacuum to give 4-(4-fluoro-2-methylindol-5-yloxy)-6-methoxy-7-(3-(pyrrolidin-1-yl)propoxy)cinnoline (32 mg, 38%).

$^1$H NMR Spectrum: (DMSOd$_6$, CF$_3$COOD) 1.85–2.0 (m, 2H); 2.0–2.2 (m, 2H); 2.25–2.4 (m, 2H); 2.45 (s,3H); 3.02–3.18 (m, 2H); 3.32–3.45 (m, 2H); 3.68 (m, 2H); 4.16 (s, 3H); 4.46 (t, 2H); 6.35 (s, 0.5 H; partly exchanged); 7.15 (dd, 1H); 7.3 (d, 1H); 7.78 (s, 1H); 7.84 (s, 1H); 8.73 (s, 1H).

MS-ESI: 451 [MH]$^+$.

The starting material was prepared as follows:

To a suspension of sodium hydride (5.42 g, 226 mmol) (prewashed with pentane) in THF (100 ml) cooled at 10° C. was added ethyl acetoacetate (29.4 g, 226 mmol) while keeping the temperature below 15° C. After completion of addition, the mixture was further stirred for 15 minutes and cooled to 5° C. A solution of 1,2,3-trifluoro-4-nitrobenzene (20 g, 113 mmol) in THF (150 ml) was added while keeping the temperature below 5° C. The mixture was then left to warm up to ambient temperature and stirred for 24 hours. The volatiles were removed under vacuum and the residue was partitioned between ethyl acetate and 2N aqueous hydrochloric acid. The organic layer was washed with water, brine, dried (MgSO$_4$) and evaporated. The residue was dissolved in concentrated hydrochloric acid (650 ml) and acetic acid (600 ml) and the mixture was refluxed for 15 hours. After cooling, the volatiles were removed under vacuum and the residue was partitioned between aqueous sodium hydrogen carbonate (5%) and ethyl acetate. The organic layer was washed with sodium hydrogen carbonate, water, brine, dried (MgSO$_4$) and evaporated. The residue was purified by column chromatography eluting with ethyl acetate/petroleum ether (75/25) to give 3-acetylmethyl-1,2-difluoro-4-nitrobenzene (17.5 g, 72%).

$^1$H NMR Spectrum: (CDCl$_3$) 2.4 (s, 3H); 4.25 (s, 2H); 7.25 (dd, 1H); 8.0 (dd, 1H).

A solution of 3-acetylmethyl-1,2-difluoro-4-nitrobenzene (500 mg, 2.3 mmol) in methylene chloride (5 ml) containing montmorillonite K10 (1 g) and trimethyl orthoformate (5 ml) was stirred for 24 hours at ambient temperature. The solid was filtered, washed with methylene chloride and the filtrate was evaporated to give 1,2-difluoro-3-(2,2-dimethoxypropyl)-4-nitrobenzene (534 mg, 88%).

$^1$H NMR Spectrum: (CDCl$_3$) 1.2 (s, 3H); 3.2 (s, 6H); 3.52 (s, 2H); 7.18 (dd, 1H); 7.6 (m, 1H).

To a solution of benzyl alcohol (221 mg, 2.05 mmol) in DMA (1.5 ml) was added 60% sodium hydride (82 mg, 2.05 mmol). The mixture was stirred for 1 hour at ambient temperature. A solution of 1,2-difluoro-3-(2,2-dimethoxypropyl)-4-nitrobenzene (534 mg, 2.05 mmol) in DMA (1.5 ml) was added and the mixture was stirred for 3 hours at ambient temperature. The mixture was diluted with 1N hydrochloric acid (10 ml) and extracted with ethyl acetate. The organic layer was evaporated and the residue was dissolved in TBF (2 ml) and 6N hydrochloric acid (0.3 ml) was added. The mixture was stirred for 1 hour at ambient temperature and the solvents were removed under vacuum. The residue was partitioned between ethyl acetate and water. The organic layer was separated, washed with brine, dried (MgSO$_4$) and evaporated. The solid was triturated with ether, filtered, washed with ether and dried under vacuum to give 3-acetylmethyl-1-benzyloxy-2-fluoro-4-nitrobenzene (350 mg, 56%).

$^1$H NMR Spectrum: (CDCl$_3$) 2.35 (s, 3H); 4.25 (s, 2H); 5.25 (s, 2H); 7.0 (dd, 1H); 7.32–7.5 (m, 5H); 8.0 (dd, 1H).

A solution of 3-acetylmethyl-1-benzyloxy-2-fluoro-4-nitrobenzene (300 mg, 0.99 mmol) in ethanol (10 ml) and acetic acid (1 ml) containing 10% palladium on charcoal (30 mg) was hydrogenated at 2 atmospheres pressure for 2 hours. The mixture was filtered and the filtrate was evaporated. The residue was dissolved in ethyl acetate and the organic layer was washed with aqueous sodium hydrogen carbonate, brine and evaporated to give 4-fluoro-5-hydroxy-2-methylindole. The residue was purified by column chromatography eluting with ethyl acetate/petroleum ether (317) to give 4-fluoro-5-hydroxy-2-methylindole (63 mg, 30%).

MS-ESI: 166 [MH]$^+$.

$^1$H NMR Spectrum: (DMSOd$_6$) 2.35 (s, 3H); 6.05 (s, 1H); 6.65 (dd, 1H); 6.9 (d, 1H); 8.75 (s, 1H); 10.9 (s, 1H).

$^{13}$C NMR Spectrum: (DMSOd$_6$) 13.5 ; 94,0; 106,0; 112; 118.5 (d); 132 (d); 136 (d); 136.5; 142.5 (d).

Alternatively the 4-fluoro-5-hydroxy-2-methylindole may be prepared as follows:

To a solution of 2-fluoro-4-nitroanisole (9.9 g, 58 mmol) and 4-chlorophenoxyacetonitrile (10.7 g, 64 mmol) in DMF (50 ml) cooled at −15° C. was added potassium tert-butoxide (14.3 g, 127 mmol) in DMF (124 ml). After stirring for 30 minutes at −15° C., the mixture was poured onto cooled 1N hydrochloric acid. The mixture was extracted with ethyl acetate. The organic layer was washed with 1N sodium hydroxide, brine, dried (MgSO$_4$) and evaporated. The residue was purified by column chromatography eluting with methylene chloride. The fractions containing the expected product were combined and evaporated. The residue was dissolved in ethanol (180 ml) and acetic acid (24 ml) containing 10% palladium on charcoal (600 mg) and the mixture was hydrogenated under 3 atmospheres pressure for 2 hours. The mixture was filtered, and the volatiles were removed under vacuum. The residue was partitioned between ethyl acetate and water. The organic layer was separated, and washed with saturated sodium hydrogen carbonate followed by brine, dried (MgSO$_4$) and evaporated. The residue was purified by column chromatography eluting with methylene chloride to give a mixture of 4-fluoro-5-methoxyindole and 6-fluoro-5-methoxyindole (5.64 g, 59%) in a ratio 1/2.

$^1$H NMR Spectrum: (DMSOd$_6$) 3.85 (s, 3H); 6.38 (s, 1H, 6-Fluoro); 6.45 (s, 1H; 4-Fluoro); 6.9–7.4 (m, 3H)

A solution of 4-fluoro-5-methoxyindole and 6-fluoro-5-methoxyindole in a ratio 1/2 (496 mg, 3 mmol), di-tertbutyl dicarbonate (720 mg, 3.3 mmol) in acetonitrile (12 ml) containing DMAP (18 mg, 0.15 mmol) was stirred at ambient temperature for 24 hours. The volatiles were removed under vacuum. The residue was dissolved in ethyl acetate, washed with 1N hydrochloric acid, followed by water, brine, dried (MgSO$_4$) and evaporated to give a mixture of 4-fluoro-5-methoxy-1-tert-butoxycarbonylindole and 6-fluoro-5-methoxy-1-tert-butoxycarbonylindole in a ratio 1/2(702 mg, 88%).

$^1$H NMR Spectrum: (DMSOd$_6$) 1.65 (s, 9H); 3.9 (s, 3H); 6.6 (d, 1H, 6-fluoro); 6.72 (d, 1H, 4-fluoro); 7.2 (t, 1H, 6-fluoro); 7.4 (d, 1H, 4-fluoro); 7.62 (d, 1H, 6-fluoro); 7.68 (d, 1H, 4-fluoro); 7.78 (s, 1H, 4-fluoro); 7.85 (s, 1H, 6-fluoro)

To a solution of 4-fluoro-5-methoxy-1-tert-butoxycarbonylindole and 6-fluoro-5-methoxy-1-tert-butoxycarbonylindole in a ratio 1/2 (8.1 g, 30.5 mmol) in TMF (100 ml) cooled at −65° C. was added tert-butyllithium (1.7 M) (23 ml, 35.7 mmol). After stirring for 4 hours at −70° C., methyl iodide (8.66 g, 61 mmol) was added and the mixture was left to warm-up to ambient temperature. Water was added and the mixture was extracted with ether. The organic layer was washed with water, brine, dried (MgSO$_4$) and evaporated and was used directly in the next step.

The crude product was dissolved in methylene chloride (100 ml) and TFA (25 ml) was added. After stirring for 1 hour at ambient temperature, the volatiles were removed under vacuum. The residue was dissolved in ethyl acetate and the organic layer was washed with 1N sodium hydroxide, followed by water, brine, dried (MgSO$_4$) and evaporated. The residue was purified by column chromatography, eluting with ethyl acetate/petroleum ether (3/7) to give 6-fluoro-5-methoxy-2-methylindole (1.6 g) and 4-fluoro-5-methoxy-2-methylindole (0.8 g, 48%)

6-fluoro-5-methoxy-2-methylindole:

MS-ESI: 180 [MH]$^+$.

$^1$H NMR Spectrum: (DMSOd$_6$) 2.35 (s, 3H); 3.8 (s, 3H); 6.05 (s, 1H); 7.1 (s, 1H); 7.12 (s, 1H); 10.8 (s, 1H).

4-fluoro-5-methoxy-2-methylindole:

MS-ESI: 180 [MH]$^+$.

$^1$H NMR Spectrum: (DMSOd$_6$) 2.35 (s, 3H); 3.8 (s, 3H); 6.15 (s, 1H); 6.9 (t, 1H); 7.05 (d, 1H); 11.0 (s, 1H).

To a solution of 4-fluoro-5-methoxy-2-methylindole (709 mg, 3.95 mmol) in methylene chloride (9 ml) cooled at −30° C. was added a solution of boron tribromide (2.18 g, 8.7 mmol) in methylene chloride (1 ml). After stirring for 1 hour at ambient temperature, the mixture was poured onto water and was diluted with methylene chloride. The pH of the aqueous layer was adjusted to 6. The organic layer was separated, washed with water, brine, dried (MgSO$_4$) and evaporated. The residue was purified by column chromatography, eluting with ethyl acetate/petroleum ether (3/7) to give 4-fluoro-5-hydroxy-2-methylindole (461 mg, 70%).

MS-ESI: 166 [MH]$^+$.

$^1$H NMR Spectrum: (DMSOd$_6$) 2.35 (s, 3H); 6.05 (s, 1H); 6.65 (dd, 1H); 6.9 (d, 1H); 8.75 (s, 1H); 10.9 (s, 1H).

$^{13}$C NMR Spectrum: (DMSOd$_6$) 13.5 ; 94.0; 106.0; 112; 118.5 (d); 132 (d); 136 (d); 136.5; 142.5 (d).

Alternatively the 4-fluoro-5-hydroxy-2-methylindole may be prepared as follows:

A solution of sodium methoxide (freshly prepared from sodium (1.71 g) and methanol (35 ml)) was added to a solution of 1,2-difluoro-3-(2,2-dimethoxypropyl)-4-nitrobenzene (16.2 g, 62 mmol), (prepared as described above), in methanol (200 ml) cooled at 5° C. The mixture was left to warm to ambient temperature and was stirred for 3 days. The volatiles were removed under vacuum and the residue was partitioned between ethyl acetate and 2N hydrochloric acid (1 ml). The organic layer was concentrated to a total volume of 100 ml and THF (100 ml) and 6N hydrochloric acid (25 ml) were added. The mixture was stirred for 1 hour at ambient temperature. The volatiles were removed under vacuum and the residue was partitioned between ethyl acetate and water. The organic layer was separated, washed with water, brine, dried (MgSO$_4$) and evaporated. The residue was purified by column chromatography eluting with ethyl acetate/petroleum ether (3/7) to give 3-acetylmethyl-2-fluoro-1-methoxy-4-nitrobenzene (12.7 g, 90%).

MS-ESI: 250 [MNa]+.

$^1$H NMR Spectrum: (CDCl$_3$) 2.38 (s, 3H); 4.0 (s, 3H); 4.25 (s, 2H); 7.0 (dd, 1H); 8.05 (d, 1H).

To a solution of 3-acetylmethyl-2-fluoro-1-methoxy-4-nitrobenzene (11.36 g, 50 mmol) in acetone (200 ml) was added 4M aqueous ammonium acetate (700 ml) followed by a solution of titanium trichloride (15% in water, 340 ml) dropwise. The mixture was stirred for 10 minutes at ambient temperature and the mixture was extracted with ether. The organic layer was washed with 0.5N aqueous sodium hydroxide followed by water, brine, dried (MgSO$_4$) and the volatiles were removed under vacuum. The residue was purified by column chromatography eluting with methylene chloride to give 4-fluoro-5-methoxy-2-methylindole (8.15 g, 90%).

$^1$H NMR Spectrum: (DMSO) 2.35 (s, 3H); 3.8 (s, 3H); 6.1 (s, 1H); 6.85 (dd, 1H); 7.02 (d, 1H).

Cleavage of 4-fluoro-5-methoxy-2-methylindole with boron tribromide to give 4-fluoro-5-hydroxy-2-methylindole is described above.

Pyrrolidine (50 g, 700 mmol), 3-chloropropanol (58.5 ml, 700 mmol) and potassium carbonate (145 g, 1.05 mol) were refluxed in acetonitrile (1 l) for 20 hours. Upon cooling to ambient temperature the precipitate was filtered off and rinsed with acetonitrile. The solvent was evaporated off and the residual oil purified by distillation under vacuum to give 3-(pyrrolidin-1-yl)propan-1-ol (62.1 g, 69%).

$^1$H NMR Spectrum: (CDCl$_3$) 1.75 (m, 6H); 2.55 (m, 4H); 2.75 (t, 2H); 3.85 (t, 2H); 5.50 (br s, 1H).

To a solution of 4-chloro-7-hydroxy-6-methoxycinnoline (300 mg, 1.42 mmol), triphenylphosphine (747 mg, 2.85 mmol) and 3-(pyrrolidin-1-yl)propan-1-ol (276 mg, 2.1 mmol) in methylene chloride (12 ml) was added diethyl azodicarboxylate (449 µl, 2.85 mmol) dropwise and the mixture was stirred for 2 hours at ambient temperature. The volatiles were removed under vacuum and the residue was purified by column chromatography eluting with methylene chloride/methanol (90/10) followed by methylene chloride/methanol/methanol saturated with ammonia (89/10/1 followed by 85/10/5). The fractions containing the expected product were combined and evaporated to give 4-chloro-6-methoxy-7-(3-(pyrrolidin-1-yl)propoxy)cinnoline (80 mg, 18%).

$^1$H NMR Spectrum: (DMSOd$_6$, CF$_3$COOD) 1.8–2.0 (m, 2H); 2.0–2.15 (m, 2H); 2.3 (t, 2H); 3.05–3.15 (m, 2H)); 3.4 (t, 2H); 3.7 (m, 2H); 4.15 (s, 3H); 4.45 (t, 2H); 7.45 (s, 1H); 7.9 (s, 1H); 9.5 (s, 1H).

Mass spectrum: 322 [MH]$^+$.

A solution of 7-benzyloxy-4-chloro-6-methoxycinnoline hydrochloride (3.06 g, 9 mmol), in TFA (30 ml) was heated at reflux for 5 hours. After evaporation of the solvent, the residue was suspended in water and adjusted to pH7 with saturated aqueous sodium hydrogen carbonate solution. The resulting solid was filtered off, washed with water and ether and dried under vacuum to give 4-chloro-7-hydroxy-6-methoxycinnoline as a yellow solid (1.78 g, 94%).

A solution of 4-chloro-7-hydroxy-6-methoxycinnoline (400 mg) was dissolved in methylene chloride (15 ml) and washed with saturated sodium hydrogen carbonate. The organic layer was separated, washed with water, brine, dried (MgSO$_4$) and evaporated to give 4-chloro-7-hydroxy-6-methoxycinnoline free base (300 mg).

The starting material, 7-benzyloxy-4-chloro-6-methoxycinnoline hydrochloride, was obtained by heating a solution of 7-benzyloxy-4-hydroxy-6-methoxycinnoline (11 g, 39 mmol) in thionyl chloride (180 ml) containing DMF (1 ml) at reflux for 1 hour. After cooling, excess thionyl chloride was removed by evaporation and azeotroped with toluene. The residue was triturated with ether, filtered off, washed with ether and dried under vacuum to give 7-benzyloxy-4-chloro-6-methoxycinnoline hydrochloride as a cream solid (13.6 g, quantitative).

The starting material 7-benzyloxy-4-hydroxy-6-methoxycinnoline was obtained by dropwise addition of a solution of sodium nitrite (4.9 g, 0.072 mol) in water (10 ml) to a solution of 2-amino-4-benzyloxy-5-methoxyacetophenone (16.3 g 0.06 mol) in acetic acid (250 ml) and 70% sulphuric acid (7.3 ml). After stirring for 30 minutes, triethylamine (25 ml) was added and stirring was continued for 6 hours. After adjusting to pH3.2 with 2M aqueous sodium hydroxide solution, the solid was filtered off, washed with water, ether and dried under vacuum to give 7-benzyloxy-4-hydroxy-6-methoxycinnoline (12.76 g, 75%) as a brown solid.

m.p. 262–264° C.

The starting material 2-amino-4-benzyloxy-5-methoxyacetophenone was obtained by adding powdered iron (520 mg, 9.3 mmol) to a solution of 2-nitro-4-benzyloxy-5-methoxyacetophenone (1 g, 3.3 mmol) in acetic acid (5 ml) heated at 100° C. After 30 minutes, the reaction mixture was cooled to ambient temperature and diluted with water. After extraction with ethyl acetate the organic layer was washed with water, brine, dried (MgSO$_4$) and the solvent evaporated. The residue was purified by flash chromatography using petroleum ether/ethyl acetate (3/1) as eluent to give 2-amino-4-benzyloxy-5-methoxyacetophenone (629 mg, 70%) as a yellow solid.

m.p. 139–141° C.

The starting material 2-nitro-4-benzyloxy-5-methoxyacetophenone was obtained by, addition of a suspension of tin(IV)chloride (15.8 ml, 0.13 mol) and 69.5% nitric acid (9.1 ml, 0.2 mol) in methylene chloride (10 ml), dropwise over a period of 20 minutes, to a solution of 4-benzyloxy-3-methoxyacetophenone (28.9 g, 0.11 mol) in methylene chloride (400 ml) cooled at −35° C.

After stirring for 20 minutes at −25° C., the mixture was warmed to ambient temperature and poured onto ice/water (1 litre). After extraction with methylene chloride the organic layer was washed with brine, dried (MgSO$_4$) and the solvent evaporated. The residue was purified by flash chromatography using petroleum ether/ethyl acetate (7/3) as eluent to give 2-nitro-4-benzyloxy-5-methoxyacetophenone (27 g, 76%) as a yellow solid.

m.p. 134–136° C.

The starting material, 4-benzyloxy-3-methoxyacetophenone, was obtained by heating a solution of 4-hydroxy-3-methoxyacetophenone (20 g, 0.12 mol), benzyl bromide (15.7 ml, 0.13 mol) and potassium carbonate (49.8 g, 0.36 mol) in DMF (400 ml) at 40° C. overnight. After cooling, the mixture was diluted with water, acidified to approximately pH3 and extracted with ethyl acetate. The organic layer was washed with brine, dried (MgSO$_4$) and the solvent evaporated. The residue was purified by flash chromatography using petroleum ether/ethyl acetate (8/2 followed by 65/35) as eluent to give 4-benzyloxy-3-methoxyacetophenone (30.3 g, 99%).

m.p. 86–88° C.

EXAMPLE 2

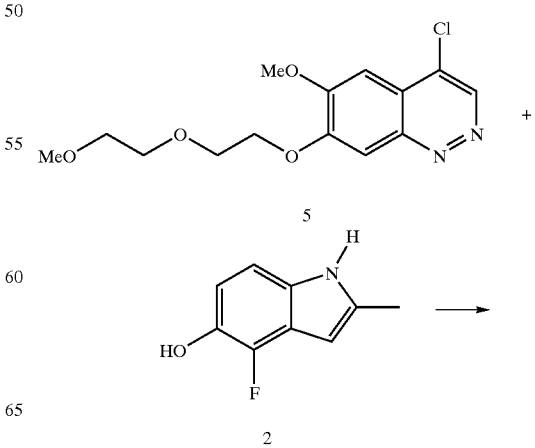

-continued

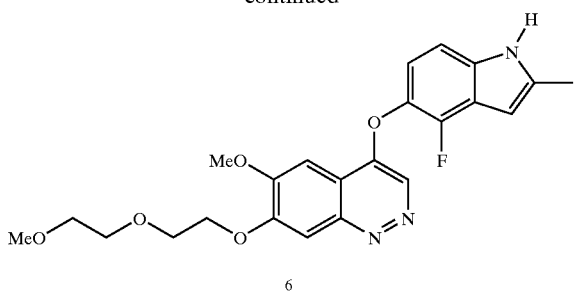

6

Using an analogous procedure to that described in Example 1, 4-chloro-6-methoxy-7-(2-(2-methoxyethoxy)ethoxy)cinnoline (100 mg, 0.32 mmol) was reacted with 4-fluoro-5-hydroxy-2-methylindole (64 mg, 0.38 mmol), (prepared as described for the starting material in Example 1), to give 4-(4-fluoro-2-methylindol-5-yloxy)-6-methoxy-7-(2-(2-methoxyethoxy)ethoxy)cinnoline (26 mg, 19%).

$^1$H NMR Spectrum: (DMSOd$_6$) 2.45 (s, 3H); 3.25 (s, 3H); 3.5 (m, 2H); 3.65 (m, 2H); 3.9 (m, 2H); 4.04 (s, 3H); 4.4 (m, 2H); 6.3 (s, 1H); 7.07 (dd, 1H); 7.24 (d, 1H); 7.55 (s, 1H); 7.79 (s, 1H); 8.3 (s, 1H).

MS-ESI: 442 [MH]$^+$.

The starting compound 4-chloro-6-methoxy-7-(2-(2-methoxyethoxy)ethoxy)cinnoline was obtained by adding triphenylphosphine (995 mg, 3.8 mmol), followed by diethyleneglycol (271 μl, 2.2 mmol) and diethyl azodicarboxylate (598 μl, 3.8 mmol), dropwise, to a suspension of 4-chloro-7-hydroxy-6-methoxycinnoline (0.4 g, 1.9 mmol), (prepared as described for the starting material in Example 1), in methylene chloride (12 ml) under nitrogen and cooled to 10° C. After stirring for 1 hour, the solvent was evaporated and the residue purified by flash chromatography using methylene chloride/ethyl acetate (5/5 followed by 4/6) as eluent to give 4-chloro-6-methoxy-7-(2-(2-methoxyethoxy)ethoxy)cinnoline (366 mg, 91%).

EXAMPLE 3

A mixture of 7-benzyloxy-4-chloro-6-methoxy cinnoline (2 g, 6.66 mmol), (prepared as described for the starting material in Example 1), 4-fluoro-5-hydroxy-2-methylindole (1.32 g, 7.99 mmol), (prepared as described for the starting material in Example 1), and cesium carbonate (3.2 g, 9.98 mmol) in DMF (40 ml) was heated at 95° C. for 1.5 hours. 4-Fluoro-5-hydroxy-2-methylindole (82 mg, 0.5 mmol) and cesium carbonate (3.2 g, 9.98 mmol) were added. The mixture was stirred for 1.5 hours at 115° C. The mixture was cooled, the solid was filtered and the filtrate was evaporated under vacuum. The residue was purified by column chromatography, eluting with methylene chloride/ethyl acetate (90/10 followed by 80/20) followed by methylene chloride/ethyl acetate/methanol (80/18/2). The fractions containing the expected product were combined and evaporated and the residue was triturated with ether/pentane (1/1). The solid was filtered, washed with pentane and dried under vacuum to give 7-benzyloxy-4-(4-fluoro-2-methylindol-5-yloxy)-6-methoxycinnoline (1.1 g, 39%).

$^1$H NMR Spectrum: (DMSOd$_6$) 2.43 (s, 3H); 4.04 (s, 3H); 5.4 (s, 2H); 6.3 (s, 1H); 7.08 (dd, 1H); 7.25 (d, 1H); 7.35–7.5 (m, 3H); 7.55 (d, 2H); 7.57 (s, 1H); 7.9 (s, 1H); 8.33 (s, 1H).

MS-ESI: 430 [MH]$^+$.

EXAMPLE 4

A solution of 7-benzyloxy-4-(4-fluoro-2-methylindol-5-yloxy)-6-methoxycinnoline (500 mg, 1.17 mmol), (prepared as described in Example 3), ammonium formate (740 mg, 11.7 mmol), 10% palladium on charcoal (100 mg) and water (700 μl) in DMF (10 ml) was stirred for 2 hours at ambient temperature. The mixture was filtered on diatomaceous earth and the filtrate was evaporated under vacuum. The residue was triturated with a mixture of ether and pentane (1/1). The solid was filtered, washed with pentane and dried under vacuum to give 4-(4-fluoro-2-methylindol-5-yloxy)-7-hydroxy-6-methoxycinnoline (300 mg, quant.).

$^1$H NMR Spectrum: (DMSOd$_6$) 2.45 (s, 3H); 4.09 (s, 3H); 6.32 (br s, 1H); 7.07 (dd, 1H), 7.25 (d, 1H); 7.55 (s, 1H); 7.62 (s, 1H); 8.28 (s, 1H).

MS-ESI: 340 [MH]$^+$.

EXAMPLE 5

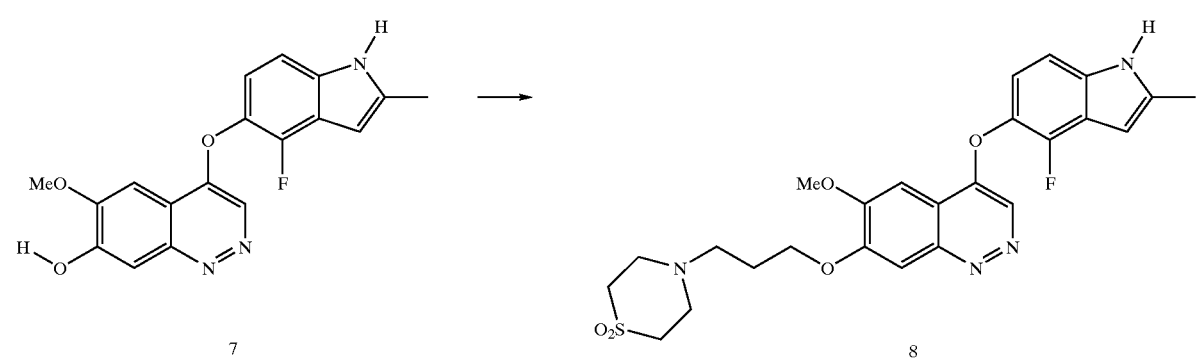

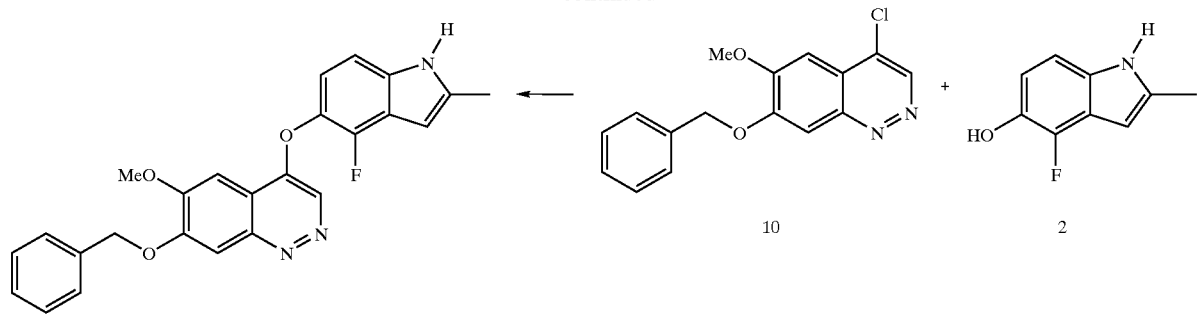

Under nitrogen a suspension of 4-(4-fluoro-2-methylindol-5-yloxy)-7-hydroxy-6-methoxycinnoline (100 mg, 0.295 mmol), (prepared as described in Example 4), 3-(1,1-dioxothiomorpholino)-1-propanoltosylate (123 mg, 0.354 mmol) and potassium carbonate (81 mg, 0.59 mmol) in DMF (6 ml) was stirred for 2.5 hours at 100° C. The mixture was poured onto water and extracted with ethyl acetate. The organic layer was separated, washed with water, brine, dried (MgSO$_4$) and evaporated. The residue was triturated with a mixture of ether/pentane (1/1), filtered, washed with pentane and dried under vacuum to give 7-(3-(1,1-dioxothiomorpholino)propoxy)-4-(4-fluoro-2-methylindol-5-yloxy)-6-methoxycinnoline (63 mg, 42%).

$^1$H NMR Spectrum: (DMSOd$_6$) 2.0 (m, 2H); 2.4 (s, 3H); 2.7 (m, 2H); 2.95 (br s, 4H); 3.15 (br s, 4H); 4.1 (s, 3H); 4.35(m, 2H); 6.4 (s, 1H); 7.05(dd, 1H); 7.3(d, 1H); 7.55 (s, 1H); 7.75 (s, 1H); 7.97 (s, 1H); 8.35 (s, 1H); 11.5 (br s, 1H).

MS-ESI: 515 [MH]$^+$.

The starting material was prepared as follows:

A mixture of 3-amino-1-propanol (650 μl, 8.4 mmol) and vinyl sulphone (1 g, 8.4 mmol) was heated at 110° C. for 45 minutes. The mixture was allowed to cool and was purified by column chromatography eluting with methylene chloride/methanol (95/5) to give 3-(1,1-dioxothiomorpholino)propan-1-ol (800 mg, 90%).

$^1$H NMR Spectrum: (CDCl$_3$) 1.7–1.8(m, 2H); 2.73 (t, 2H); 3.06 (br s, 8H); 3.25 (s, 1H); 3.78 (t,2H).

MS-ESI: 194 [MH]$^+$.

3-(1,1-Dioxothiomorpholino)-1-propanol (12 g, 62 mmol) was dissolved into tert-butylmethyl ether (400 ml). This solution was cooled to 0° C. before the addition of DABCO (1,4-diazabicyclo[2.2.2]octane, 13.93 g, 124 mmol) followed by portionwise addition of tosyl chloride (17.8 g, 93 mmol). The reaction mixture was stirred for 1 hour at 0° C. and for 3 hours at ambient temperature. The solvent was evaporated off and the residue taken up in methylene chloride. The organic salts were removed by filtration and the filtrate was purified by flash chromatography using methanol/methylene chloride (5/95) as eluent. Evaporation of the solvents and trituration with ether gave 3-(1,1-dioxothiomorpholino)-1-propanoltosylate (9.44 g, 44%) as a white solid.

$^1$H NMR Spectrum: (DMSOd$_6$) 1.75 (m, 2H); 2.45 (m, 5H); 2.75 (m, 4H); 3.0 (m, 4H); 4.10 (t, 2H); 7.50 (d, 2H); 7.85 (d, 2H).

EXAMPLE 6

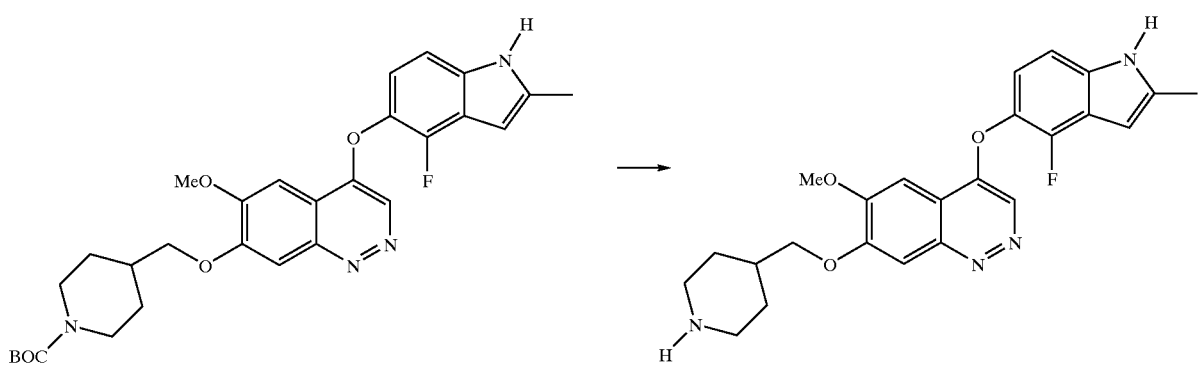

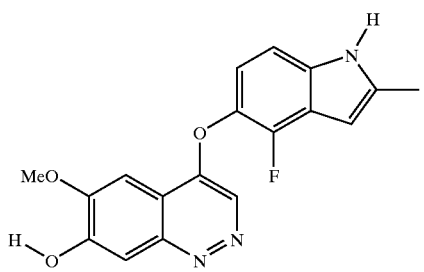

7

A solution of 7-(1-(tert-butoxycarbonyl)piperidin-4-ylmethoxy)-4-(4-fluoro-2-methylindol-5-yloxy)-6-methoxycinnoline (100 mg, 0.186 mmol) in methylene chloride (3 ml) containing TFA (1 ml) was stirred at ambient temperature for 2 hours. The volatiles were removed under vacuum. The residue was partitioned between water and methylene chloride and the pH of the aqueous layer was adjusted to 13 with 6N aqueous sodium hydroxide. The organic layer was separated, washed with water, brine, dried (MgSO$_4$) and evaporated. The residue was triturated with ether/pentane (1/1). The solid was filtered, washed with pentane and dried under vacuum to give 4-(4-fluoro-2-methylindol-5-yloxy)-6-methoxy-7-(piperidin-4-ylmethoxy)cinnoline (50 mg, 62%).

$^1$H NMR Spectrum: (DMSOd$_6$) 1.15–1.3 (m, 2H); 1.78 (d, 2H); 1.9–2.05 (m, 1H); 2.45 (s, 3H); 2.5–2.65 (m, 2H); 3.0 (d, 2H); 4.05 (s, 3H); 4.1 (d, 2H); 6.3 (s, 1H); 7.05 (dd, 1H); 7.25 (d, 1H); 7.55 (s, 1H); 7.75 (s, 1H); 8.32 (s, 1H).

MS-ESI: 436 [MH]$^+$.

The starting material was prepared as follows:

While maintaining the temperature in the range 0–5° C., a solution of di-tert-butyl dicarbonate (41.7 g, 0.19 mol) in ethyl acetate (75 ml) was added in portions to a solution of ethyl 4-piperidinecarboxylate (30 g, 0.19 mol) in ethyl acetate (150 ml) cooled at 5° C. After stirring for 48 hours at ambient temperature, the mixture was poured onto water (300 ml). The organic layer was separated, washed successively with water (200 ml), 0.1N aqueous hydrochloric acid (200 ml), saturated sodium hydrogen carbonate (200 ml) and brine (200 ml), dried (MgSO$_4$) and evaporated to give ethyl 4-(1-(tert-butoxycarbonyl)piperidine)carboxylate (48 g, 98%).

$^1$H NMR Spectrum: (CDCl$_3$) 1.25 (t, 3H); 1.45 (s, 9H); 1.55–1.70 (m, 2H); 1.8–2.0(d, 2H); 2.35–2.5 (m, 1H); 2.7–2.95(t, 2H); 3.9–4.1 (br s, 2H); 4.15 (q, 2H).

A solution of 1M lithium aluminum hydride in THF (133 ml, 0.133 mol) was added in portions to a solution of ethyl 4-(1-(tert-butoxycarbonyl)piperidine)carboxylate (48 g, 0.19 mol) in dry THF (180 ml) cooled at 0° C. After stirring at 0° C. for 2 hours, water (30 ml) was added followed by 2N sodium hydroxide (10 ml). The precipitate was removed by filtration through diatomaceous earth and washed with ethyl acetate. The filtrate was washed with water, brine, dried (MgSO$_4$) and evaporated to give 1-(tert-butoxycarbonyl)-4-hydroxymethylpiperidine (36.3 g, 89%).

MS (EI): 215 [M.]+.

$^1$H NMR Spectrum: (CDCl$_3$) 1.05–1.2(m, 2H); 1.35–1.55 (m, 10H); 1.6–1.8(m, 2H); 2.6–2.8(t, 2H); 3.4–3.6(t, 2H); 4.0–4.2(br s, 2H).

1,4-Diazabicyclo[2.2.2]octane (42.4 g, 0.378 mol) was added to a solution of 1-(tert-butoxycarbonyl)-4-hydroxymethylpiperidine (52.5 g, 0.244 mol) in tert-butyl methyl ether (525 ml). After stirring for 15 minutes at ambient temperature, the mixture was cooled to 5° C. and a solution of toluene sulphonyl chloride (62.8 g, 0.33mmol) in tert-butyl methyl ether (525 ml) was added in portions over 2 hours while maintaining the temperature at 0° C. After stirring for 1 hour at ambient temperature, petroleum ether (11) was added. The precipitate was removed by filtration. The filtrate was evaporated to give a solid. The solid was dissolved in ether and washed successively with 0.5N aqueous hydrochloric acid (2×500 ml), water, saturated sodium hydrogen carbonate and brine, dried (MgSO$_4$) and evaporated to give 1-(tert-butoxycarbonyl)-4-(4-methylphenylsulphonyloxymethyl)piperidine (76.7 g, 85%).

MS (ESI): 392 [MNa]$^+$.

$^1$H NMR Spectrum: (CDCl$_3$) 1.0–1.2(m, 2H); 1.45(s, 9H); 1.65(d, 2H); 1.75–1.9(m, 2H); 2.45(s, 3H); 2.55–2.75 (m, 2H); 3.85(d, 1H); 4.0–4.2(br s, 2H); 7.35(d, 2H); 7.8(d, 2H).

Under nitrogen a mixture of 4-(4-fluoro-2-methylindol-5-yloxy)-7-hydroxy-6-methoxycinnoline (150 mg, 0.44 mmol), (prepared as described in Example 4), 1-(tert-butoxycarbonyl)-4-(4-methylphenylsulfonyloxymethyl) piperidine (196 mg, 0.53 mmol) and potassium carbonate (122 mg, 0.88 mmol) in DMF (6 ml) was stirred at 100° C. for 2.5 hours. The mixture was filtered, and filtrate was evaporated under vacuum. The residue was purified by column chromatography eluting with methylene chloride followed by methylene chloride/methanol (99/1 and 95/5). The fractions containing the expected product were combined and evaporated. The residue was triturated with a mixture of pentane/ether (1/1) and the solid was filtered, washed with pentane and dried under vacuum to give 7-(1-(tert-butoxycarbonyl)piperidin-4-yl)methoxy)-4-(4-fluoro-2-methylindol-5-yloxy)-6-methoxycinnoline (100 mg, 42%).

$^1$H NMR Spectrum: (DMSOd$_6$) 1.2–1.3 (m, 2H); 1.41 (s, 9H); 1.85 (d, 2H); 2.1 (m, 1H); 2.42 (s, 3H); 2.8 (m, 2H); 4.0 (m, 2H); 4.05 (s, 3H); 4.15 (d, 2H); 6.3 (s, 1H); 7.06 (dd, 1H); 7.25 (d, 1H); 7.55 (s, 1H); 7.75 (s, 1H); 8.3 (s, 1H).

MS-ESI: 537 [MH]$^+$.

EXAMPLE 7

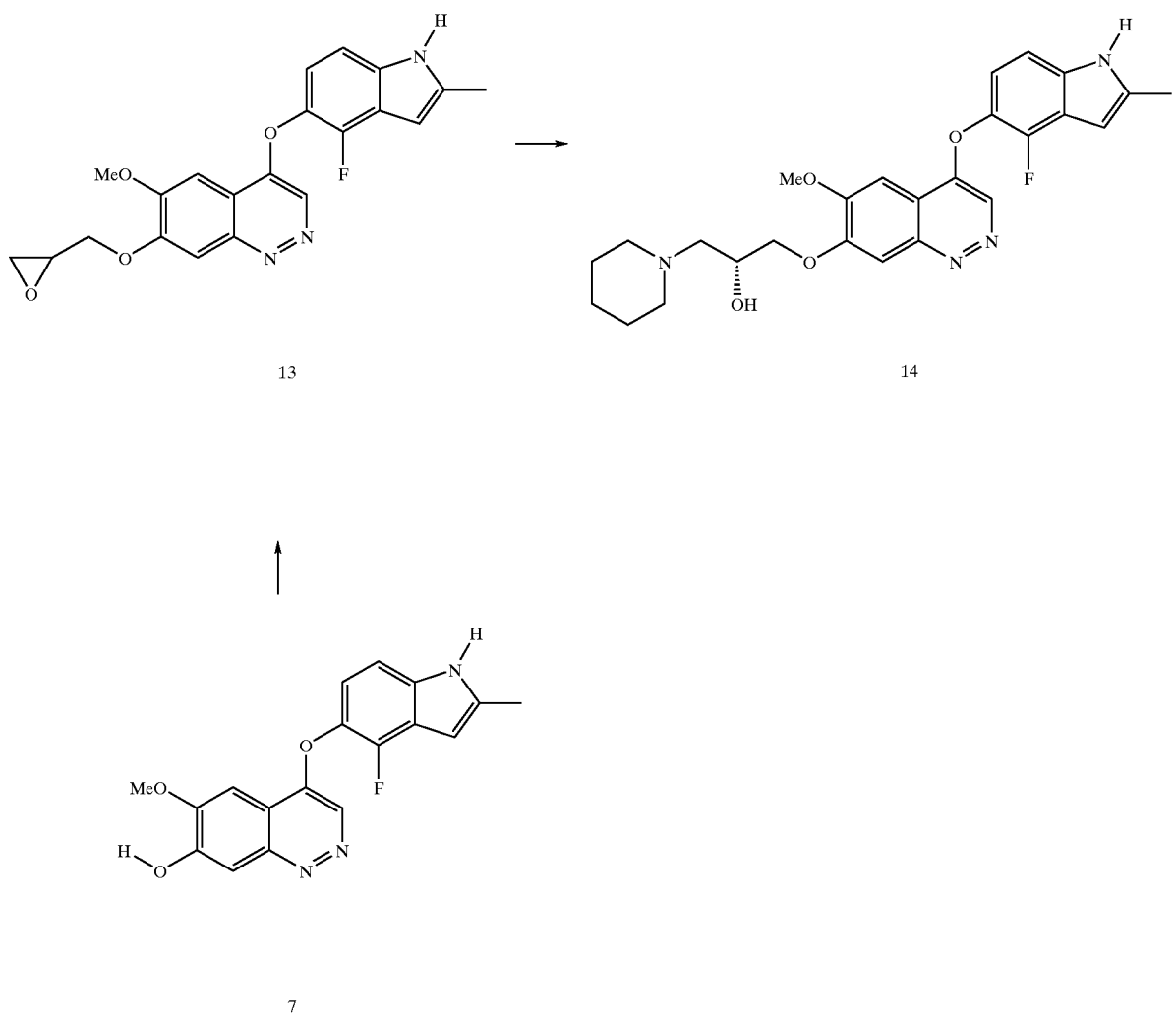

Under nitrogen a solution of 7-(R)-(2,3-epoxypropoxy)-4-(4-fluoro-2-methylindol-5-yloxy)-6methoxycinnoline (110 mg, 0.278 mmol) and piperidine (83 μl, 0.835 mmol) in DMF (2 ml) was stirred at 60° C. for 3 hours. The volatiles were removed under vacuum and the residue was purified by column, chromatography eluting with methylene chloride followed by methylene chloride/methanol (95/5) and methylene chloride/methanol saturated with ammonia (95/5 followed by 90/10). The fractions containing the expected product were combined and evaporated. The residue was triturated with ether, filtered, washed with ether and dried under vacuum to give 4-(4-fluoro-2-methylindol-5-yloxy)-7-(R)-(2-hydroxy-3-(piperidin-1-yl)propoxy)-6-methoxycinnoline (65 mg, 49%).

$^1$H NMR Spectrum: (DMSOd6, CF$_3$COOD) 1.35–1.5 (m, 1H); 1.65–1.9 (m, 5H); 2.45 (s, 3H); 2.9–3.1 (m, 2H); 3.2–3.4 (m, 2H); 3.5–3.6 (m, 2H); 4.15 (s, 3H); 4.35 (br s, 2H); 4.52 (m, 1H); 6.3 (s, 0.3H, partly exchanged); 7.1 (dd, 1H); 7.3 (d, 1H); 7.8 (s, 1H); 7.85 (s, 1H); 8.72 (s, 1H).

MS-ESI: 481 [MH]$^+$.

The starting material was prepared as follows:

Under nitrogen a suspension of 4-(4-fluoro-2-methylindol-5-yloxy)-7-hydroxy-6-methoxycinnoline (150 mg, 0.442 mmol), (prepared as described in Example 4), 2-(R)-glycidyltosylate (121 mg, 0.53 mmol) and potassium carbonate (183 mg, 1.32 mmol) in DMA (3 ml) was stirred at 60° C. for 3 hours. The mixture was then poured onto water and extracted with ethyl acetate. The organic layer was washed with aqueous ammonia, followed by water, brine, dried (MgSO$_4$) and evaporated. The residue was triturated with ether, filtered, washed with ether and dried under vacuum to give 7-(R)-(2,3-epoxypropoxy)-4-(4-fluoro-2-methylindol-5-yloxy)-6-methoxycinnoline (115 mg, 66%).

$^1$H NMR Spectrum: (DMSOd$_6$) 2.45 (s, 3H); 2.8 (dd, 1H); 2.92 (dd, 1H); 3.5 (m, 1H); 4.05 (s, 3H); 4.1 (dd, 1H); 4.68 (dd, 1H); 6.3 (s, 1H), 7.1 (dd, 1H); 7.25 (d, 1H); 7.58 (s, 1H); 7.8 (s, 1H); 8.35 (s, 1H).

MS-ESI: 396 [MH]$^+$.

EXAMPLE 8

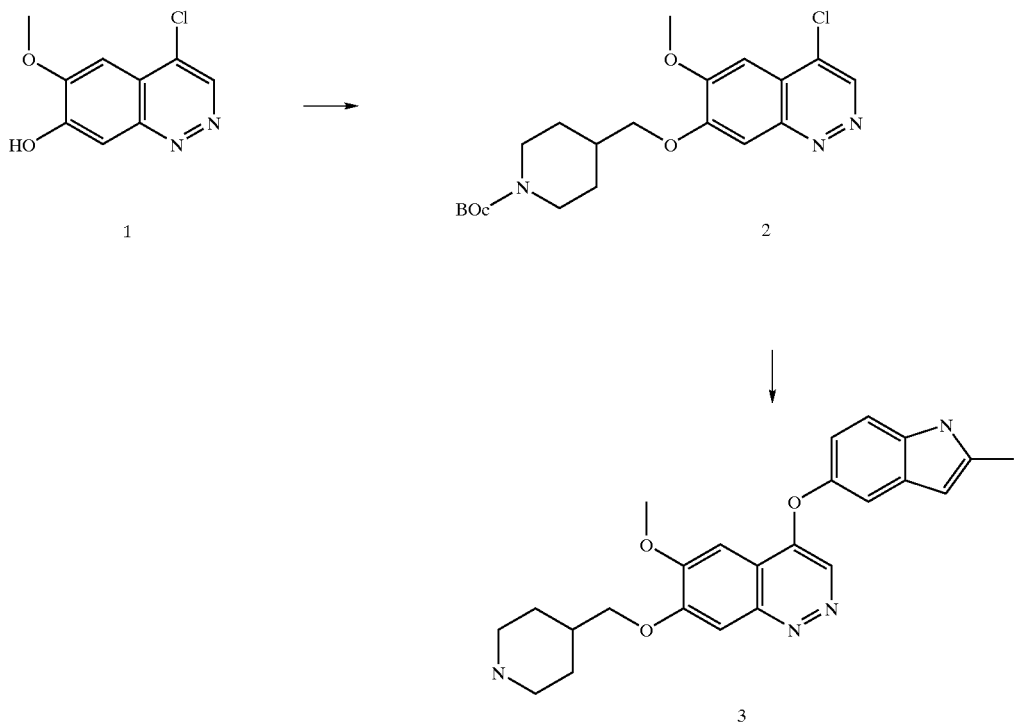

A mixture of 7-(1-(tert-butoxycarbonyl)piperidin-4-ylmethoxy)4chloro-6-methoxycinnoline (204 mg, 0.5 mmol), 5-hydroxy-2-methylindole (81 mg) and cesium carbonate (326 mg, 1 mmol) in DMF (2.5 ml) was stirred at 90° C. for 2 hours. After cooling, the mixture was filtered, washed with DMF and the volatiles were removed under vacuum. The crude product was dissolved in methylene chloride (4 ml) containing TEA (1.5 ml) and was stirred at ambient temperature for 1 hour. The volatiles were removed under vacuum. The residue was partitioned between methylene chloride and 1N aqueous sodium hydroxide. The organic layer was separated, dried (MgSO$_4$), filtered and evaporated. The residue was purified by column chromatography eluting with a gradient of methylene chloride/methanol saturated with ammonia (5/95 to 15/85). The fractions containing the expected product were combined and evaporated. The residue was triturated under diethyl ether and the precipitate was filtered, washed with ether and dried under vacuum to give 7-(1-tert-butoxycarbonylpiperidin-4-ylmethoxy)-6-methoxy-4-(2-methylindol-5yl)cinnoline (42 mg, 20%).

$^1$H NMR Spectrum: (DMSOd$_6$, CF$_3$COOD) 1.58–1.7 (m, 2H); 2.05 (d, 2H); 2.3 (m, 1H); 2.45 (s, 3H); 3.02 (m, 2H); 4.18 (s, 3H); 4.3 (d, 2H); 6.22 (s, 0.5H, partly exchanged); 7.05 (d, 1H); 7.5 (m, 2H); 7.75 (s, 1H); 7.82 (s, 1H); 8.6 (s, 1H).

MS: 419.6 [MH]$^+$.

The starting material was prepared as follows:

DEAD (1.46 g, 8.38 mmol) was added to a suspension of 4-chloro-7-hydroxy-6-methoxycinnoline (1.47 g, 6.98 mmol), (prepared as described for the starting material in Example 1), 1-(tert-butoxycarbonyl)-4-hydroxymethylpiperidine (1.65 g, 7.68 mmol), (prepared as described for the starting material in Example 6), and triphenylphosphine (2.74 g) in methylene chloride (40 ml). The mixture was stirred for 1 hour at ambient temperature then poured onto silica and eluted with a gradient of ethyl, acetate in methylene chloride (30/70 to 50/50). The fractions containing the expected product were combined and evaporated to give 7-(1-tert-butoxycarbonylpiperidin-4-ylmethoxy)-4-chloro-6-methoxycinnoline (561 mg, 58%).

MS (ESI): 408.5 and 410.5 [MH]$^+$.

A solution of boron tribromide (32.5 ml, 341 mmol) in methylene chloride (60 ml) was added in portions to a solution of 5-methoxy-2-methylindole (25 g, 155 mmol) in methylene chloride (250 ml) cooled at –45° C. After stirring for 15 minutes at –30° C., the mixture was warmed up to ambient temperature and stirred for 1 hour. Methylene chloride (300 ml) was added in portions and the mixture was cooled to 0° C. Water was added in portions and the mixture was adjusted to pH6 with 4N sodium hydroxide. The organic layer was separated. The aqueous layer was extracted with methylene chloride and the organic layers were combined, washed with water, brine, dried (MgSO$_4$) and the volatiles were removed by evaporation. The residue was purified by column chromatography eluting with ethyl acetate/methylene chloride (1/9 followed by 15/85) to give 5-hydroxy-2-methylindole (21.2 g, 93%).

EXAMPLE 9

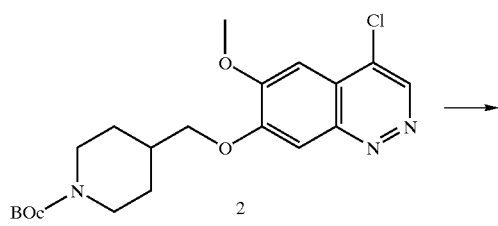

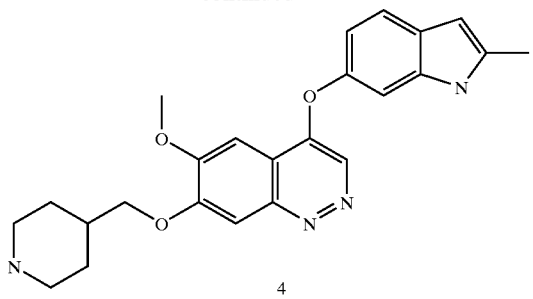

4

Using an analogous procedure to that described in Example 8, 7-(1-tert-butoxycarbonylpiperidin-4-ylmethoxy)-4-chloro-6-methoxycinnoline (204 mg, 0.5 mmol) was reacted with 6-hydroxy-2-methylindole (100 mg, 0.55 mmol) to give 7-(1-(tert-butoxycarbonyl)piperidin-4-ylmethoxy)-6-methoxy-4-(2-methylindol-6-yloxy) cinnoline. The crude product was then treated with TFA to give 6-methoxy-4-(2-methylindol-6-yloxy)-7-(piperidin-4-ylmethoxy)cinnoline (10 mg, 4%).

$^1$H NMR Spectrum: (DMSOd$_6$) 1.5–1.6 (m, 2H); 2.05 (d, 2H); 2.25 (m, 1H); 2.45 (s, 3H); 2.5–2.6 (m, 2H); 2.98 (t, 2H); 4.05 (s, 3H); 4.25 (d, 2H); 6.22 (s, 1H); 6.9 (dd, 1H); 7.22 (s, 1H); 7.55 (s, 1H); 7.8 (s, 1H); 8.4 (s, 1H).

MS: 418.5 [MH]$^+$.

EXAMPLE 10

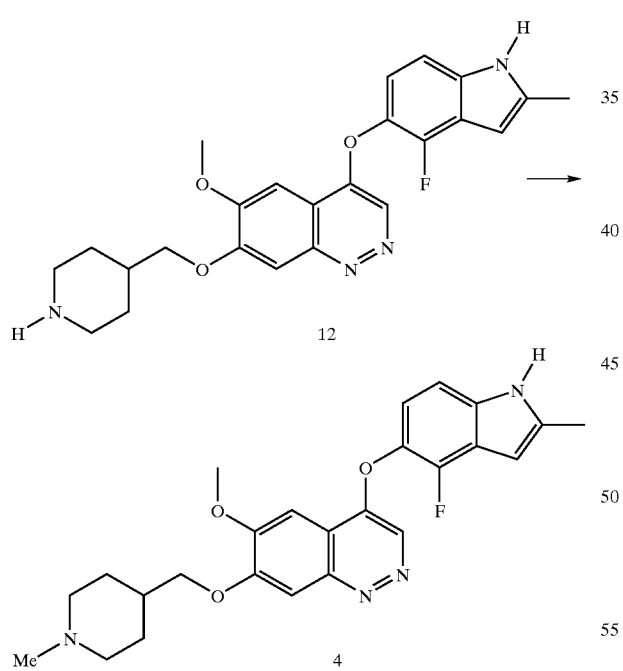

To a solution of 4-(4-fluoro-2-methylindol-5-yloxy)-6-methoxy-7-(piperidin-4-ylmethoxy)cinnoline (170 mg, 0.31 mmol), (prepared as described in Example 6), in methylene chloride (6 ml) and methanol (3 ml) was added a solution of sodium acetate (25 mg, 0.31 mmol). Acetic acid (22 ml) and formaldehyde (37%) (50 ml) were added. The mixture was stirred for 5 minutes and triacetate sodium borohydride (100 mg, 0.46 mmol) was added in portions. The mixture was stirred at ambient temperature for 1 hour. The volatiles were removed under vacuum and the residue was dissolved in water and the pH was adjusted to 10 with 2N aqueous sodium hydroxide. The mixture was extracted with ethyl acetate. The organic layer was washed with brine, dried (MgSO$_4$) and evaporated. The residue was triturated under diethyl ether, filtered, washed with ether and dried under vacuum to give 4-(4-fluoro-2-methylindol-5-yloxy)-6-methoxy-7-(1-methylpiperidin-4-ylmethoxy)cinnoline (75 mg, 43%).

$^1$H NMR Spectrum: (DMSOd$_6$) 1.4–1.5 (m, 2H); 1.75 (d, 2H); 1.7–1.8 (m, 1H); 1.9 (dd, 2H); 2.2 (s, 3H); 2.5 (s, 3H); 2.85 (d, 2H); 4.06 (s, 3H); 4.14 (d, 2H); 6.33 (s, 1H); 7.1 (dd, 1H); 7.26 (d, 1H); 7.57 (s, 1H); 7.76 (s, 1H); 8.34 (s, 1H); 11.5 (br s, 1H).

MS: 449.5 [MH]$^+$.

EXAMPLE 11

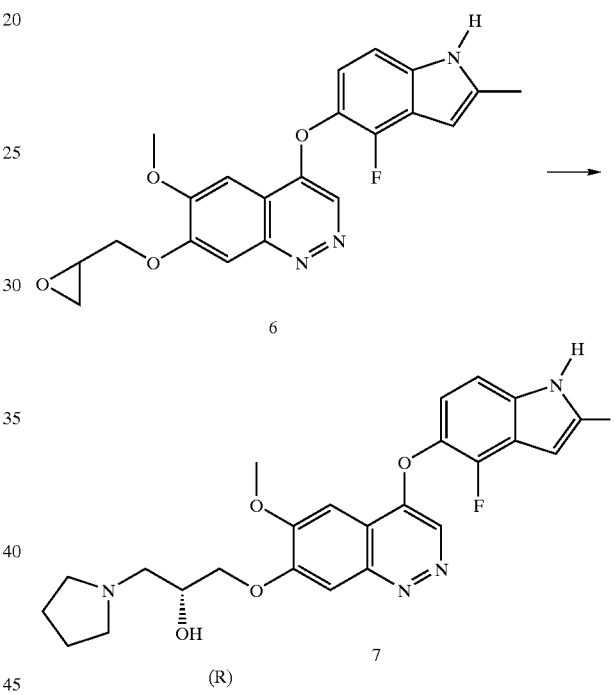

A solution of 7-(R)-(2,3-epoxypropoxy)-4-(4-fluoro-2-methylindol-5-yloxy)-6-methoxycinnoline (400 mg, 1 mmol), (prepared as described for the starting material in Example 7), and pyrrolidine (0.42 ml) in DMF (10 ml) was stirred at 70° C. for 2 hours. After cooling the volatiles were removed under vacuum and the mixture was poured onto silica and eluted with methylene chloride/methanol (95/5 followed by 90/10) followed by methylene chloride/methanol saturated with ammonia (95/5 followed by 90/10). The fractions containing the expected product were combined and evaporated to give 4-(4-fluoro-2-methylindol-5-yloxy)-7-(R)-(2-hydroxy-3-(pyrrolidin-1-yl)propoxy)-6-methoxycinnoline (200 mg, 43%).

$^1$H NMR Spectrum: (DMSOd$_6$) 1.87–2.1 (m, 4H); 2.4 (s, 3H); 3.1–3.2 (m, 2H); 3.3–3.45 (m, 2H); 3.65 (m, 2H); 4.18 (s, 3H); 4.35 (br s, 2H); 4.35–4.45 (m, 1H); 6.3 (s, 0.3H, partly exchanged); 7.1 (dd, 1H); 7.3 (d, 1H); 7.8 (s, 1H); 8.82 (s, 1H); 8.7 (s, 1H).

MS: 467 [MH]$^+$.

EXAMPLE 12

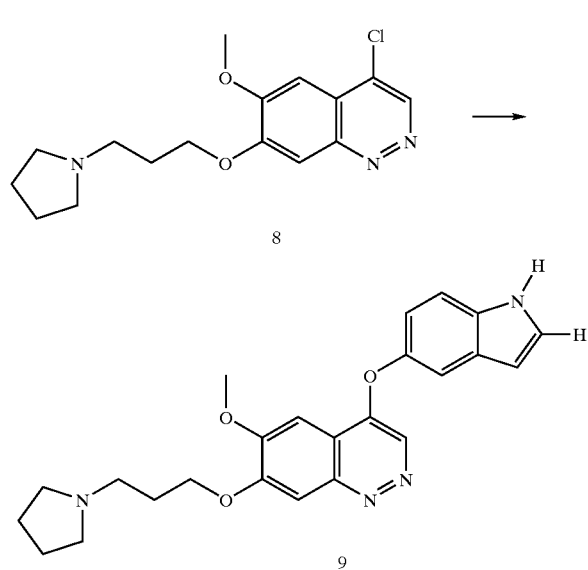

A suspension of 4-chloro-6-methoxy-7-(3-(pyrrolidin-1-yl)propoxy)cinnoline (200 mg, 0.62 mmol), (prepared as described for the starting material in Example 1), 5-hydroxyindole (100 mg, 0.75 mmol) and potassium carbonate (129 mg, 0.93 mmol) in DMF (3 ml) was stirred at 100° C. for 6 hours. After cooling, the volatiles were removed under vacuum and the residue was purified by column chromatography eluting with methylene chloride/ methanol saturated with ammonia (98/2 to 90/10). The fractions containing the expected product were combined and evaporated to give 4-(indol-5-yloxy)-6-methoxy-7-(3-(pyrrolidin-1-yl)propoxy)cinnoline (40 mg, 15%).

$^1$H NMR Spectrum: (DMSOd$_6$) 1.72 (br s, 4H); 2.05 (m, 2H); 2.5 (m, 4H); 2.6 (dd, 2H); 4.05 (s, 3H); 4.32 (dd, 2H); 6.5 (br s, 1H); 7.05 (dd, 1H); 7.45–7.6 (m, 4H); 7.75 (s, 1H); 8.38 (s, 1H).

MS: 419.5 [MH]$^+$.

EXAMPLE 13

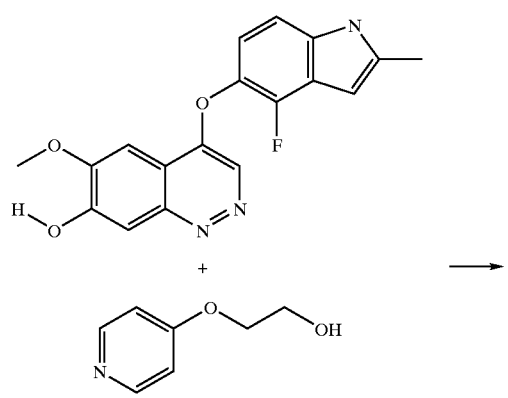

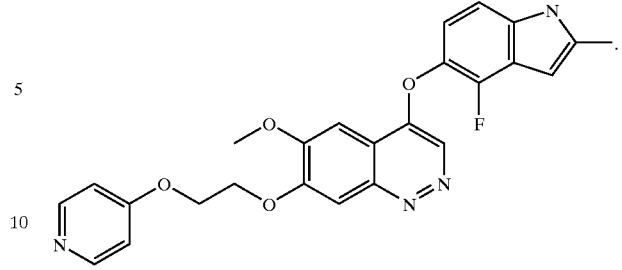

DEAD (0.19 ml, 1.2 mmol) was added dropwise to a solution of 4-(4-fluoro-2-methylindol-5-yloxy)-7-hydroxy-6-methoxycinnoline (0.2 g, 0.6 mmol), (prepared as described in Example 4), 4-(2-hydroxyethoxy)pyridine (0.125 g, 0.9 mmol), (J. Chem. Soc. Perkin II, 1987, 1867), and triphenylphosphine (0.31 g, 1.2 mmol) in DMF (4 ml). After stirring for 2 hours at ambient temperature, the volatiles were removed under vacuum to give an oil that crystallised on standing. The solid was triturated with methylene chloride, filtered, washed with methylene chloride and dried under vacuum to give 4-(4-fluoro-2-methylindol-5-yloxy)-6-methoxy-7-(2-(4-pyridyloxy)ethoxy)cinnoline (90 mg, 33%).

$^1$H NMR Spectrum: (DMSO d$_6$) 2.45 (s, 3H); 4.08 (s, 3H); 4.6 (m, 2H); 4.7 (m, 2H); 6.32 (s, 1H); 7.05–7.12 (m, 3H); 7.26 (d, 1H); 7.6 (s, 1H); 7.9 (s, 1H); 8.36 (s, 1H); 8.45 (d, 2H).

MS: 461.5 [M+H]$^+$.

EXAMPLE 14

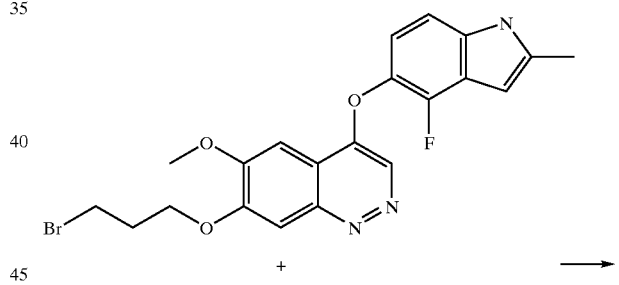

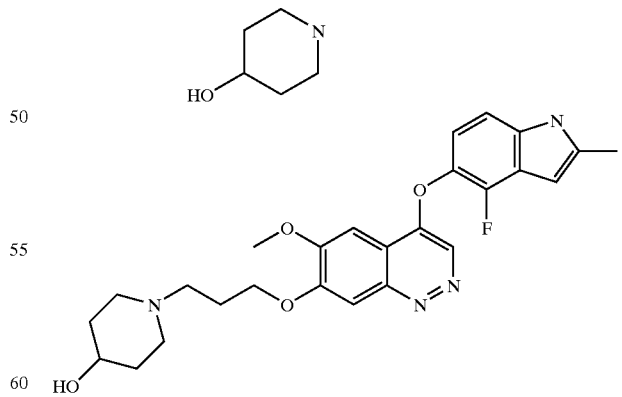

A solution of 4-hydroxypiperidine (0.5 g, 4.95 mmol) and 7-(3-bromopropoxy)-4-(4-fluoro-2-methylindol-5-yloxy)-6-methoxycinnoline (0.3 g, 0.65 mmol) in DMF (4 ml) was stirred at 60° C. for 30 minutes. The volatiles were removed under vacuum and the residue was purified by column chromatography eluting with ethyl acetate/methylene chloride (1/1) followed by ethyl acetate/methanol/methylene chloride (4/1/5) followed by methylene chloride/methanol saturated with ammonia (9/1). The fractions containing the expected product were combined and evaporated to give 4-(4-fluoro-2-methylindol-5-yloxy)-7-(3-(4-hydroxypiperidin-1-yl)propoxy)-6-methoxycinnoline (25 mg, 8%).

MS: 481.6 [M+H]⁺.

The starting material was prepared as follows:

DEAD (0.47 ml, 2.95 mmol) was added dropwise to a solution of 4-(4-fluoro-2-methylindol-5-yloxy)-7-hydroxy-6-methoxycinnoline (0.5 g, 1.47 mmol), (prepared as described in Example 4), 3-bromopropan-1-ol (0.2 ml, 2.21 mmol) and triphenylphosphine (0.78 g, 2.95 mmol) in DMF (10 ml). The mixture was stirred for 1 hour at ambient temperature and the volatiles were removed under vacuum. The residue was purified by column chromatography eluting with ethyl acetate/methylene chloride (1/1). The fractions containing the expected product were combined and evaporated to give 7-(3-bromopropoxy)-4-(4-fluoro-2-methylindol-5-yloxy)-6-methoxycinnoline (0.6 g, 88%) (purity 80%; contaminated by some triphenylphosphine oxide).

¹H NMR Spectrum: (DMSO d₆) 2.4 (m, 2H); 2.42 (s, 3H); 3.75 (dd, 2H); 4.05 (s, 3H); 4.4 (m, 2H); 6.32 (s, 1H); 7.08 (dd, 1H); 7.28 (d, 1H); 7.55 (m, 1H); 7.8 (s, 1H); 8.35 (s, 1H).

MS: 460–462 [M+H]⁺.

EXAMPLE 15

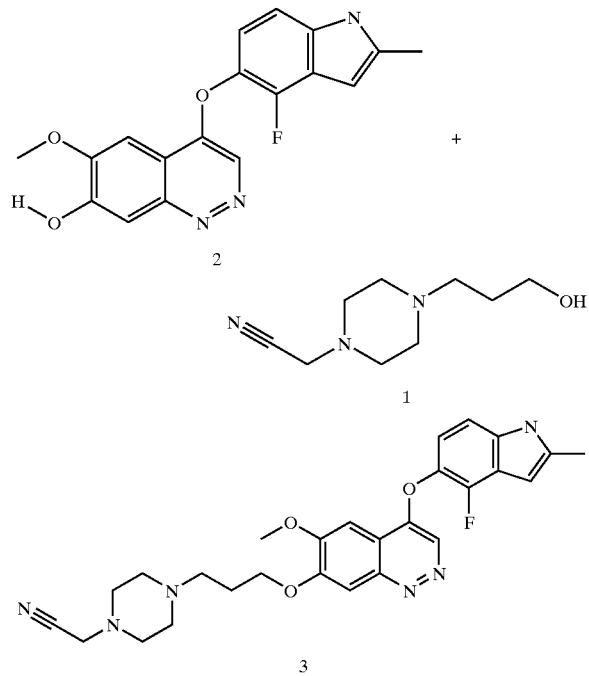

Diethyl azodicarboxylate (0.095 ml, 0.6 mmol) was added dropwise to a suspension of 4-(4-fluoro-2-methylindol-5-yloxy)-7-hydroxy-6-methoxycinnoline (0.1 g, 0.3 mmol), prepared as described in Example 4), 3-(4-cyanomethylpiperazin-1-yl)propan-1-ol (0.085 g, 0.45 mmol) and triphenylphosphine (0.155 g, 0.6 mmol) in methylene chloride (2.5 ml). The mixture was stirred for 30 minutes at ambient temperature. Further 3-(4-cyanomethylpiperazin-1-yl)propan-1-ol (0.085 g, 0.45 mmol), triphenylphosphine (0.155 g, 0.6 mmol) and diethyl azodicarboxylate (0.095 ml, 0.6 mmol) were added. The mixture was stirred for 30 minutes and the volatiles were removed under vacuum. The residue was purified by column chromatography eluting with ethylacetate/methylene chloride (1/1) followed by methanol/ethyl acetate/methylene chloride (5/45/50 followed by 10/40/50 and 10/0/90). The fractions containing the expected product were combined and evaporated to give 7-(3-(4-cyanomethylpiperazin-1-yl)propoxy)-4-(4-fluoro-2-methylindol-5-yloxy)-6-methoxycinnoline (0.035 g, 24%).

¹H NMR Spectrum: (DMSOd₆, CF₃COOD) 2.3–2.4 (m, 2H), 2.45 (s, 3H), 2.55–2.7 (m, 2H), 3.0–3.2 (m, 4H), 3.4 (m, 2H), 3.6–3.75 (m, 2H), 3.95 (s, 2H), 4.2 (s, 3H), 4.42 (m, 2H), 6.35 (s, 0.5H, partly exchanged), 7.08 (dd, 1H), 7.3 (d, 1H), 7.8 (s, 1H); 7.9 (s, 1H), 8.75 (s, 1H).

MS: 505.6 (M+H)⁺.

The starting material was prepared as follows:

A solution of 1-piperazinecarboxaldehyde (25 g, 0.219 mol), 3-bromo-1-propanol (33.5 g, 0.241 mol) and potassium carbonate (38 g, 0.273 mol) in methanol (33 ml) was heated at reflux for 5 hours. After cooling, the solid was filtered, washed with methanol and the filtrate was evaporated. The residue was dissolved in methylene chloride and washed with a small amount of water. The organic layer was washed with brine, dried (MgSO₄), filtered and evaporated. The residue was purified by column chromatography eluting with methylene chloride/methanol (90/10 followed by 80/20) to give 4-(3-hydroxypropyl)-1-piperazinecarboxaldehyde (4.5 g, 12%).

¹H NMR Spectrum: (DMSOd₆) 1.55–1.7 (m, 2H), 2.2–2.4 (m, 6H), 3.3–3.5 (m, 6H), 4.45 (br s, 1H), 8.0 (s, 1H).

A solution of 4-(3-hydroxypropyl)-1-piperazinecarboxaldehyde (4.45 g) in methanol (10 ml) and 4N aqueous hydrogen chloride (15 ml) was stirred at ambient temperature for 3 hours. The volatiles were removed under vacuum and the residue was partitioned between trichloromethane and aqueous sodium hydroxide (40%). The organic layer was separated, washed with brine, dried (MgSO₄) and evaporated to give 3-(piperazin-1-yl)propan-1-ol (2.35 g).

A solution of 3-(piperazin-1-yl)propan-1-ol (0.93 g, 6.45 mmol), chloroacetonitrile (0.58 g, 7.75 mmol), potassium carbonate (1.79 g, 12.9 mmol) and sodium iodide (0.32 g, 1.93 mmol) in DMF (10 ml) was stirred at ambient temperature overnight. The volatiles were removed under vacuum and the residue was purified by column chromatography eluting with ethylene chloride/methanol (95/5) to give 3-(4-cyanomethylpiperazin-1-yl)propan-1-ol (0.84 g, 71%).

¹H NMR Spectrum: (DMSOd₆) 1.5–1.65 (m, 2H), 2.25–2.6 (m, 10H), 3.45 (t, 2H), 3.7 (s, 2H), 4.45 (br s, 1H).

MS: 184 (M+H)⁺.

EXAMPLE 16

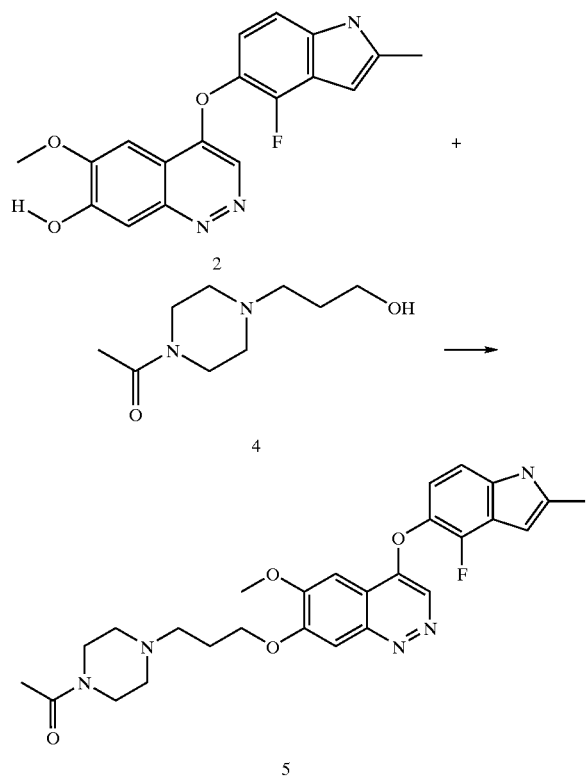

Under nitrogen, diethyl azodicarboxylate (0.19 ml, 1.2 mmol) was added dropwise to a suspension of 4-(4-fluoro-2-methylindol-5-yloxy)-7-hydroxy-6-methoxycinnoline (0.2 g, 0.6 mmol), (prepared as described in Example 4), in DMF (4 ml) containing triphenylphosphine (0.31 g, 1.2 mmol) and 3-(4-acetylpiperazin-1-yl)propan-1-ol (0.15 g, 0.9 mmol). After stirring for 2 hours at ambient temperature, the volatiles were removed under vacuum. The residue was purified by column chromatography eluting with methylene chloride, followed by ethyl acetate/methylene chloride (1/1) followed by methanol/ethyl acetate/methylene chloride (1/4/5) followed by methanol/methylene chloride (1/9). The fractions containing the expected product were combined and evaporated to give 7-(3-(4-acetylpiperazin-1-yl)propoxy)-4-(4-fluoro-2-methylindol-5-yloxy)-6-methoxycinnoline (0.11 g, 37%).

$^1$H NMR Spectrum: (DMSOd$_6$, CF$_3$COOD) 2.07 (s, 3H), 2.4 (m, 2H), 2.44 (s, 3H), 2.85–3.25 (m, 3H), 3.3–3.5 (m, 3H); 3.6 (d, 2H)); 4.1 (d, 2H); 4.17 (s, 3H); 4.45–4.55 (m, 3H); 6.34 (s, 0.5H, partly exchanged), 7.2 (dd, 1H), 7.35 (d, 1H), 7.79 (s, 1H), 7.84 (s, 1H), 8.75 (s, 1H).

MS: 508 (M+H)$^+$.

The starting material was prepared as follows:

A suspension of 1-acetylpiperazine (3.85 g, 0.03 mol) and 3-bromopropan-1-ol (4 ml) containing potassium carbonate (8.3 g, 60 mmol) in acetonitrile (30 ml) was stirred at 80° C. for 5 hours. The solid was filtered and the filtrate was evaporated. The residue was purified by column chromatography eluting with ethanol/methylene chloride (1/9 followed by 3/7) to give 3-(4-acetylpiperazin-1-yl)propan-1-ol (3.15 g, 56%).

$^1$H NMR Spectrum: (CDCl$_3$) 1.75 (m, 2H), 2.05 (s, 3H), 2.4–2.5 (m, 4H), 2.6 (t, 2H), 3.45 (t, 2H), 3.6 (m, 2H), 3.8 (t, 2H), 4.6 (br s, 1H).

MS: 187.4 (M+H)$^+$.

EXAMPLE 17

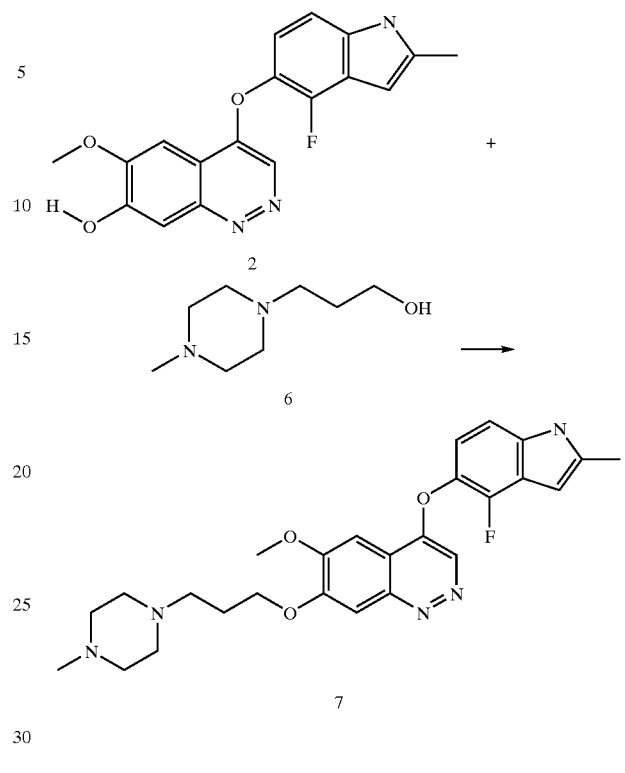

Using an analogous procedure to that described in Example 16, 4-(4-fluoro-2-methylindol-5-yloxy)-7-hydroxy-6-methoxycinnoline (0.2 g, 0.6 mmol), (prepared as described in Example 4), was reacted with 1-(3-hydroxypropyl)-4-methylpiperazine (0.14 g, 0.9 mmol) to give 4-(4-fluoro-2-methylindol-5-yl)oxy-6-methoxy-7-(3-(4-methylpiperazin-1-yl)propoxy)cinnoline (80 mg, 28%).

$^1$H NMR Spectrum: (DMSOd$_6$, CF$_3$COOD 75° C.) 2.35 (m, 2H), 2.45 (s, 3H), 2.98 (s, 3H), 3.43 (m, 2H), 3.6 (m, 8H), 4.19 (s, 3H), 4.5 (m, 2H), 6.35 (br s, 0.3H partly exchanged), 7.15 (m, 1H), 7.3 (d, 1H), 7.8 (s, 2H), 8.65 (s, 1H).

MS: 480.6 (M+H)$^+$.

The starting material was prepared as follows:

3-Bromopropan-1-ol (20 ml, 20 mmol) was added dropwise to a solution of 1-methylpiperazine (29 ml, 26 mmol) in ethanol (200 ml). Potassium carbonate (83 gr, 60 mmol) was added and the mixture was refluxed for 20 hours. After cooling, the solid was filtered and the filtrate was evaporated. The residue was triturated with ether, filtrate and evaporated. The residue was distilled at about 60–70° C. under about 0.2 mm Hg to give 1-(3-hydroxypropyl)-4-methylpiperazine (17 g, 53%).

$^1$H NMR Spectrum: (CDCl$_3$) 1.72 (m, 2H); 2.3 (s, 3H); 2.2–2.8 (m, 8H); 2.6 (t, 2H); 3.8 (t, 2H); 5.3 (br s, 1H).

EXAMPLE 18

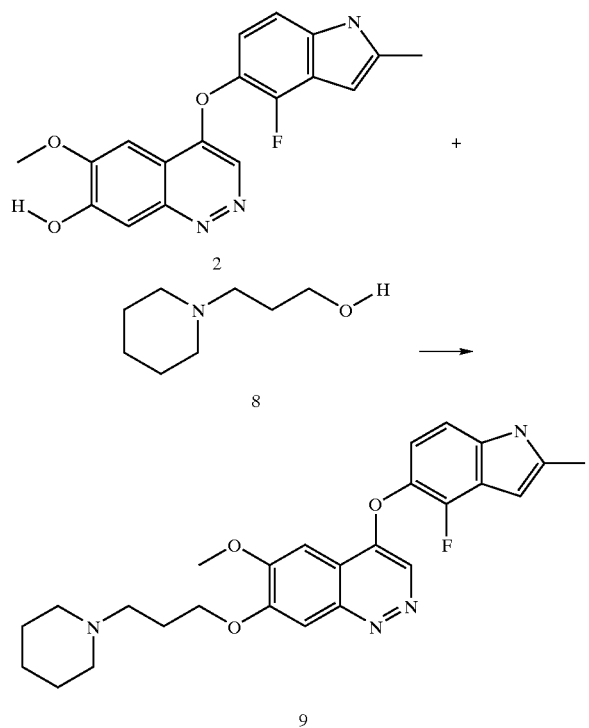

A suspension of 4-(4-fluoro-2-methylindol-5-yloxy)-7-hydroxy-6-methoxycinnoline (0.2 g, 0.6 mmol), (prepared as described in Example 4), 1-(3-chloropropyl)piperidine (0.12 g, 0.72 mmol) and potassium carbonate (0.125 g, 0.9 mmol) in DMF (5 ml) was stirred at 95° C. for 2 hours. After cooling, the precipitate was filtered. The filtrate was diluted with methylene chloride and purified by column chromatography eluting with methanol/ethyl acetate/methylene chloride (1/4/5) followed by methanol/methylene chloride (1/9) followed by methanol saturated with ammonia/methylene chloride (1/9). The fractions containing the expected product were combined and evaporated to give 4-(4-fluoro-2-methylindol-5-yloxy)-6-methoxy-7-(3-(piperidin-1-yl)propoxy)cinnoline (27 mg, 10%).

$^1$H NMR Spectrum: (DMSOd$_6$, CF$_3$COOD) 1.35–1.5 (m, 1H), 1.6–1.8 (m, 3H), 1.8–1.9 (m, 2H), 2.32 (m, 2H), 2.45 (s, 3H), 2.95 (dd, 2H), 3.3 (m, 2H), 3.55 (d, 2H), 4.18 (s, 3H), 4.45 (m, 2H), 6.35 (s, 1H), 7.15 (dd, 1H), 7.3 (d, 1H), 7.78 (s, 1H), 7.82 (s, 1H), 8.75 (s, 1H).

MS: 465.6 (M+H)$^+$.

EXAMPLE 19

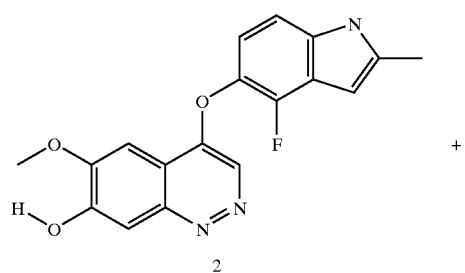

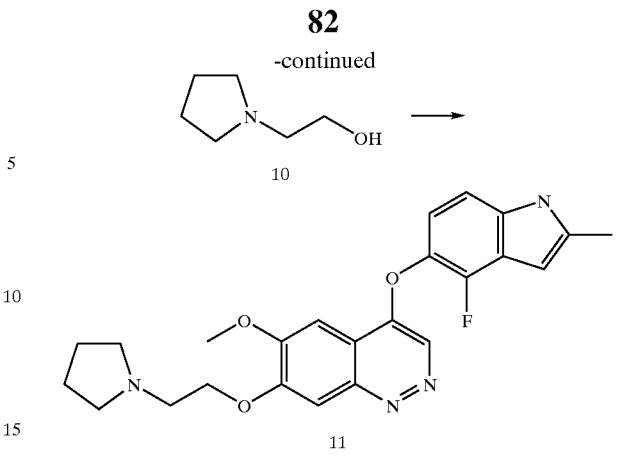

Using an analogous procedure to that described in Example 15, 4-(4-fluoro-2-methylindol-5-yloxy)-7-hydroxy-6-methoxycinnoline (0.2 g, 0.6 mmol), (prepared as described in Example 4), was reacted with 1-(2-hydroxyethyl)pyrrolidine (0.11 ml, 0.9 mmol) to give 4-(4-fluoro-2-methylindol-5-yloxy)-6-methoxy-7-(2-(pyrrolidin-1-yl)ethoxy)cinnoline (30 mg, 12%).

$^1$H NMR Spectrum: (DMSOd$_6$, CF$_3$COOD) 1.8–2.0 (br s, 2H), 2.1 (br s, 2H), 2.45 (s, 3H), 3.12 (br s, 2H), 3.7 (br s, 2H), 3.82 (s, 2H), 4.17 (s, 3H), 4.7 (br s, 2H), 6.35 (s, 0.5H, partly exchanged), 7.15 (dd, 1H), 7.3 (d, 1H), 7.8 (s, 1H), 7.85 (s, 1H), 8.75 (s, 1H).

MS: 437.5 (M+H)$^+$.

EXAMPLE 20

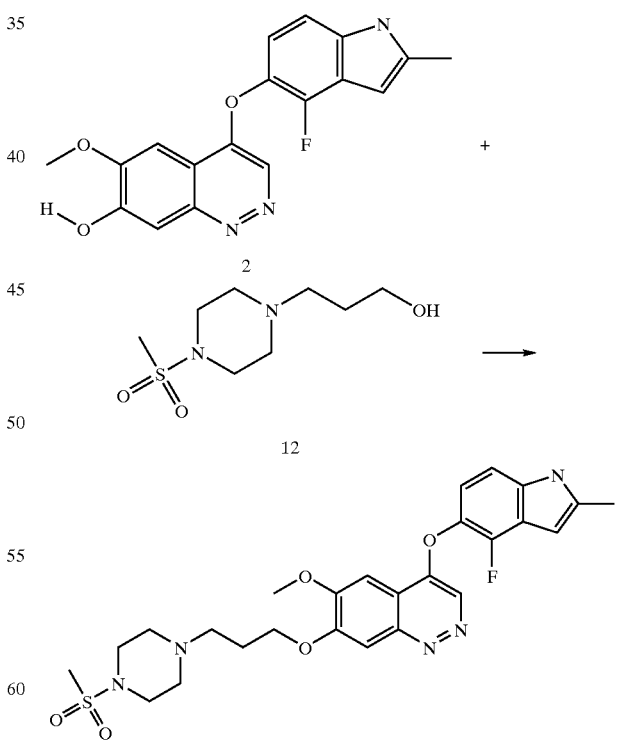

Under nitrogen, diethyl azodicarboxylate (0.19 ml, 1.2 mmol) was added dropwise to a suspension of 4-(4-fluoro- 2-methylindol-5-yloxy)-7-hydroxy-6-methoxycinnoline (0.2 g, 0.6 mmol), (prepared as described in Example 4), triphenylphosphine (0.31 g, 1.2 mmol) and 3-(4-methylsulfonylpiperazin-1-yl)propan-1-ol (0.2 g, 0.9 mmol) in DMF (4 ml). The mixture was stirred for 2 hours at ambient temperature. Methylene chloride was added and the mixture was poured onto silica and eluted with ethyl acetate/methylene chloride (1/1) followed by methanol/ethyl acetate/methylene chloride (1/4/4) followed by methanol/methylene chloride (1/9). The fractions containing the expected product were combined and evaporated. The residue was triturated with diethyl ether and filtered. The solid was washed with ether and dried under vacuum to give 4-(4-fluoro-2-methylindol-5-yl)oxy-6-methoxy-7-(3-(4-methylsulfonylpiperazin-1-yl)propoxy)cinnoline (90 mg, 28%).

$^1$H NMR Spectrum: (DMSOd$_6$, CF$_3$COOD) 2.3–2.4 (m, 2H), 2.45 (s, 3H), 3.05 (s, 3H), 3.1–3.3 (m, 4H), 3.45 (m, 2H), 3.7–3.85 (m, 4H), 4.07 (s, 3H), 4.45 (t, 2H), 6.35 (s, 0.5H, partly exchanged), 7.15 (dd, 1H), 7.32 (d, 1H), 7.8 (s, 1H), 7.85 (s, 1H), 8.75 (s, 1H).

MS: 544.5 (M+H)$^+$.

The starting material was prepared as follows:

Methanesulfonyl chloride (966 μl, 12.5 mmol) was added dropwise to a solution of 1-benzylpiperazine (2 g, 11.3 mmol) and triethylamine (1.74 ml, 12.5 mmol) in dry methylene chloride (30 ml) cooled at 0° C. After stirring for 1 hour at ambient temperature, the mixture was partitioned between water and methylene chloride. The organic layer was separated, washed with water, brine, dried (MgSO$_4$) and evaporated. The residue was purified by column chromatography eluting with methylene chloride/ethyl acetate (7/3) to give 1-benzyl-4-methylsulfonylpiperazine (2.5 g, 87%).

$^1$H NMR Spectrum: (CDCl$_3$) 2.6 (m, 4H), 2.8 (s, 3H), 3.3 (m, 4H), 3.6 (s, 2H), 7.25–7.4 (m, 5H).

MS: 255 (M+H)$^+$.

A suspension of 1-benzyl-4-methylsulfonylpiperazine (2.5 g, 9.8 mmol) and cyclohexane (30 ml) in ethanol (70 ml) containing 20% palladium hydroxide on carbon (500 mg) was stirred at 80° C. for 4 hours. The mixture was cooled, filtered and the filtrate was evaporated to give 1-methylsulfonylpiperazine (1.58 g, 98%).

$^1$H NMR Spectrum: (CDCl$_3$) 2.8 (s, 3H), 4.0 (m, 4H), 3.2 (m, 4H).

MS: 165.3 (M+H)$^+$.

A suspension of 1-methylsulfonylpiperazine (1.58 g, 9.6 mmol), 3-bromo-1-propanol (1.13 ml, 12 mmol) and potassium carbonate (1.73 g, 12 mmol) in acetonitrile (10 ml) was stirred at 40° C. for 4 hours followed by 2 hours at 70° C. The mixture was cooled, filtered and the filtrate was evaporated under vacuum. The residue was purified by column chromatography eluting with methylene chloride/methanol (97/3 followed by 95/5) to give 3-(4-methylsulfonylpiperazin-1-yl)propan-1-ol (1.95 g, 91%).

$^1$H NMR Spectrum: (CDCl$_3$) 1.8 (m, 2H), 2.7 (m, 6H), 2.8 (s, 3H), 3.3 (m, 4H), 3.82 (t, 2H), 4.5 (br s, 1H).

MS: 223.4 (M+H)$^+$.

EXAMPLE 21

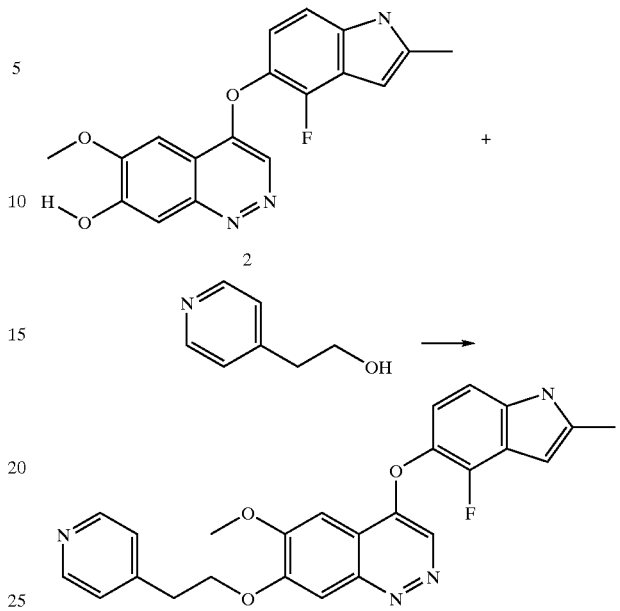

Using an analogous procedure to that described in Example 20, 4-(4-fluoro-2-methylindol-5-yloxy)-7-hydroxy-6-methoxycinnoline (0.2 g, 0.6 mmol), (prepared as described in Example 4), was reacted with 4-(2-hydroxyethyl)pyridine (0.11 g, 0.9 mmol), (Zhur. Obshchei. Khim. 1958, 28, 103–110), to give 4-(4-fluoro-2-methylindol-5-yloxy)-6-methoxy-7-(2-(4-pyridyl)ethoxy)cinnoline (0.15 g, 57%).

$^1$H NMR Spectrum: (DMSOd$_6$) 2.45 (s, 3H), 3.25 (t, 2H), 4.05 (s, 3H), 4.6 (t, 2H), 6.32 (s, 1H), 7.1 (dd, 1H), 7.28 (d, 1H), 7.45 (d, 2H), 7.57 (s, 1H), 7.85 (s, 1H), 8.35 (s, 1H), 8.55 (d, 2H).

MS: 445.5 (M+H)$^+$.

EXAMPLE 22

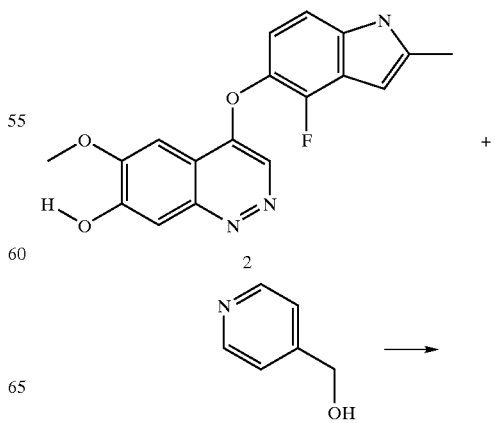

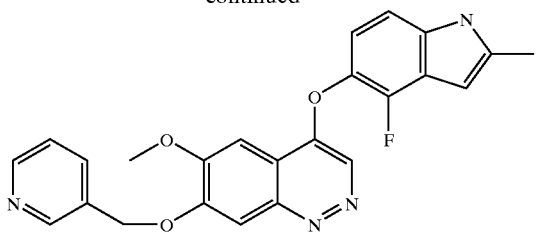

Using an analogous procedure to that described in Example 20, 4-(4-fluoro-2-methylindol-5-yloxy)-7-hydroxy-6-methoxycinnoline (0.2 g, 0.5 mol), (prepared as described in Example 4), was reacted with 3-(hydroxymethyl)pyridine (60 µl, 0.9 mmol) to give 4-(4-fluoro-2-methylindol-5-yloxy)-6-methoxy-7-(3-pyridylmethoxy)cinnoline (80 mg, 32%).

$^1$H NMR Spectrum: (DMSOd$_6$) 2.45 (s, 3H), 4.08 (s, 3H), 5.5 (s, 2H), 6.32 (s, 1H), 7.1 (dd, 1H), 7.28 (d, 1H), 7.5 (dd, 1H), 7.6 (s, 1H), 7.95 (s, 1H), 8.0 (d, 1H), 8.35 (s, 1H), 8.62 (d, 1H), 8.8 (s, 1H).

MS: 431 (M+H)$^+$.

EXAMPLE 23

The following illustrate representative pharmaceutical dosage forms containing the compound of formula I, or a pharmaceutically acceptable salt thereof hereafter compound X), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph.Eur | 223.75 |
| Croscarmellose sodium | 6.0 |
| Maize statch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph.Eur | 488.5 |
| Magnesium stearate | 1.5 |

| (e) Injection I | (50 mg/ml) |
|---|---|
| Compound X | 5.0% w/v |
| 1N Sodium hydroxide solution | 15.0% v/v |
| 0.1N Hydrochloric acid (to adjust pH to 7.6) | |
| Polyethylene glycol 400 | 4.5% w/v |
| Water for injection to 100% | |

| (f) Injection II | 10 mg/ml) |
|---|---|
| Compound X | 1.0% w/v |
| Sodium phosphate BP | 3.6% w/v |
| 0.1N Sodium hydroxide solution | 15.0% v/v |
| Water for injection to 100% | |

| (g) Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

Note

The above formulations may be obtained by conventional procedures well known in the pharmaceutical art. The tablets (a)–(c) may be enteric coated by conventional means, for example to provide a coating of cellulose acetate phthalate.

REFERENCE EXAMPLE 1

2-methyl-1H-pyrrolo[2,3-b]pyridin-5-ol

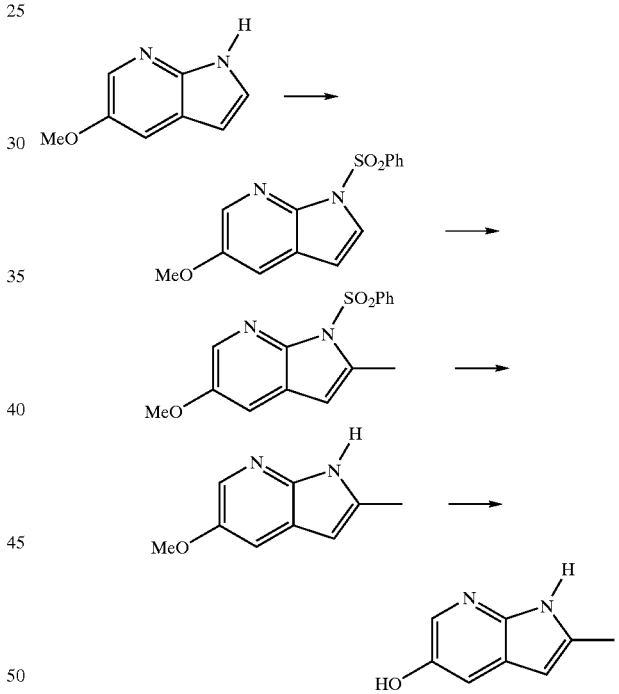

To a solution of 5-methoxy-1H-pyrrolo[2,3-b]pyridine (920 mg, 6.2 mmol) (Heterocycles 50, (2) 1065–1080, 1999) in methylene chloride (20 ml) was added benzyltriethylammonium chloride (37 mg, 0.16 mmol) followed by sodium hydroxide powder (771 mg, 19.2 mmol). The mixture was cooled to 0° C. and benzylsulfonyl chloride (991 µl, 7.77 mmol) was added dropwise. The mixture was stirred at 0° C. for 15 minutes followed by 2 hours at ambient temperature. The mixture was filtered over diatomaceous earth and the filtrate was evaporated under vacuum. The residue was purified by column chromatography eluting with ethyl acetate/petroleum ether (20/80 followed by 30/70). The fractions containing the expected product were combined and evaporated to give 5-methoxy-1-(phenylsulfonyl)-1H-pyrrolo[2,3-b]pyridine (1.69 g; 94%)

$^1$H NMR Spectrum: (DMSO d$_6$) 3.86 (s, 3H); 6.78 (d, 1H); 7.6–7.7 (m, 3H); 7.72 (dd, 1H); 7.88 (d, 1H); 8.02–8.12 (m, 3H).

MS: 289.47 [M+H]$^+$.

A solution of 5-methoxy-1-(phenylsulfonyl)-1H-pyrrolo [2,3-b]pyridine (900 mg, 3.12 mmol) in THF (22.5 ml) was added dropwise to a solution of lithium diisopropylamide (prepared from nBu-Li (2.5M in hexane); 2.5 ml) and diisopropylamine (874 μl) in THF (13.5 ml)) cooled at −25° C. and the mixture was stirred for 30 minutes. Methyl iodide (215 μl, 3.44 mmol) in THF (9 ml) was then added dropwise and the mixture was stirred for 10 minutes at −25° C., left to warm up to ambient temperature and stirred for 15 minutes. The mixture was then poured onto ice/water. The mixture was then extracted with ethyl acetate. The organic layer was separated, washed with water, brine, dried (MgSO$_4$), filtered and evaporated. The residue was purified by column chromatography, eluting with ethyl acetate/ petroleum ether (20/80 followed by 30/70). The fractions containing the expected product were combined and evaporated to give 5-methoxy-2-methyl-1-(phenylsulfonyl)-1H-pyrrolo[2,3-b]pyridine (805 mg, 85%).

$^1$H NMR Spectrum: (DMSOd$_6$) 2.7 (s, 3H); 3.82 (s, 3H); 6.51 (d, 1H); 7.49 (d, 1H); 7.59 (dd, 2H); 7.7 (m, 1H); 8.0–8.1 (m, 3H).

MS: 303.5 [M+H]$^+$.

A solution of 5-methoxy-2-methyl-1-(phenylsulfonyl)-1H-pyrrolo[2,3-b]pyridine (950 mg, 3.14 mmol) and 40% aqueous sodium hydroxide (106 ml) in methanol (160 ml) was heated at reflux for 30 minutes. After cooling, the mixture was poured onto cooled water and extracted with ethyl acetate. The organic layer was separated, washed with water, brine, dried (MgSO$_4$), filtered and evaporated. The residue was purified by column chromatography eluting with ethyl acetate/petroleum ether (1/1). The fractions containing the expected product were combined and evaporated to give 5-methoxy-2-methyl-1H-pyrrolo[2,3-b]pyridine (462 mg, 91%).

$^1$H NMR Spectrum: (DMSO d$_6$) 2.38 (s, 3H); 3.8 (s, 3H); 6.06 (d, 1H); 7.39 (d, 1H); 7.82 (d, 1H).

MS: 163.3 [M+H]$^+$.

A solution of boron tribromide (64 μl, 0.68 mmol) in methylene chloride (200 l) was added to a solution of 5-methoxy-2-methyl-1H-pyrrolo[2,3-b]pyridine (50 mg, 0.308 mmol) in methylene chloride (4 ml) cooled at −30° C. The mixture was left to warm up to ambient temperature and further stirred for 3 hours. The mixture was poured onto ice. The pH was adjusted to 6.2 with 6N aqueous sodium hydroxide followed by 2 N aqueous hydrogen chloride. The mixture was extracted with ethyl acetate. The organic layer was washed with water, followed by brine and dried (MgSO$_4$), filtered and the filtrate was evaporated. The residue was purified by column chromatography, eluting with with methylene chloride followed by methylene chloride/ methanol (98/2 followed by 95/5). The fractions containing the expected product were combined and evaporated to give 2-methyl-1H-pyrrolo[2,3-b]pyridin-5-ol (45 mg, quantitative). $^1$H NMR Spectrum: (DMSO d$_6$) 2.4 (s, 3H); 5.96 (s, 1H); 7.12 (d, 1H); 7.69 (d, 1H); 8.9 (s, 1H); 11.07 (br s, 1H).

MS: 149.2 [M+H]$^+$.

What is claimed is:
1. A compound of the formula I:

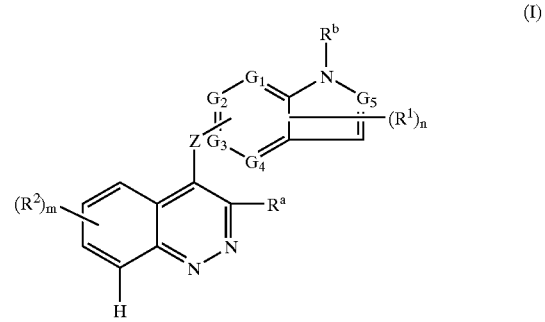

(I)

wherein:
either any one of $G_1$, $G_2$, $G_3$, $G_4$ and $G_5$ is nitrogen and the other four are —CH—, or $G_1$, $G_2$, $G_3$, $G_4$ and $G_5$ are all —CH—;

Z is —O—, —NH—, —S—, —CH$_2$— or a direct bond; Z is linked to any one of $G_1$, $G_2$, $G_3$ and $G_4$ which is a free carbon atom;

n is an integer from 0 to 5; any of the substituents $R^1$ may be attached at any free carbon atom of the indole, azaindole or indazole group, such free carbon atoms may be $G_1$, $G_2$, $G_3$, $G_4$ or $G_5$ or may be at the 3-position of the indole, azaindole or indazole group;

m is an integer from 0 to 3;

$R^a$ represents hydrogen;

$R^b$ represents hydrogen, $C_{1-4}$alkyl, $C_{1-4}$alkoxy$C_{1-4}$alkyl, amino$C_{1-4}$alkyl, $C_{1-3}$alkylamino$C_{1-4}$alkyl, di($C_{1-3}$alkyl)amino$C_{1-4}$alkyl, $C_{2-5}$alkenylamino $C_{1-4}$alkyl, $C_{2-5}$alkynylamino$C_{1-4}$alkyl, —$C_{1-5}$alkyl (ring A) wherein ring A is selected from azetidinyl, pyrrolidinyl, piperidinyl, piperazinyl, morpholino and thiomorpholino and wherein ring A may bear one or more substituents selected from $C_{1-4}$alkyl, $C_{2-5}$alkenyl, $C_{2-5}$alkynyl, hydroxy, oxo, halogeno, cyano, cyano $C_{1-4}$alkyl, $C_{1-4}$alkylsulphonyl and $C_{1-4}$alkanoyl;

$R^1$ represents hydrogen, oxo, hydroxy, halogeno, $C_{1-4}$alkyl, $C_{1-4}$alkoxy, $C_{1-4}$alkoxy$C_{1-4}$alkyl, amino $C_{1-4}$alkyl, $C_{1-3}$alkylamino$C_{1-4}$alkyl, di($C_{1-3}$alkyl) amino$C_{1-4}$alkyl, —$C_{1-5}$alkyl(ring B) wherein ring B is selected from azetidinyl, pyrrolidinyl, piperidinyl, piperazinyl, N-methylpiperazinyl, N-ethylpiperazinyl, morpholino and thiomorpholino;

$R^2$ represents hydrogen, hydroxy, halogeno, cyano, nitro, trifluoromethyl, $C_{1-3}$alkyl, $C_{1-3}$alkoxy, $C_{1-3}$alkylsulphanyl, —NR$^3$R$^4$ (wherein R$^3$ and R$^4$, which may be the same or different, each represents hydrogen or $C_{1-3}$alkyl), or R$^5$X$^1$— (wherein X$^1$ represents a direct bond, —O—, —CH$_2$—, —OC(O)—, —C(O)—, —S—, —SO—, —SO$_2$—, —NR$^6$C(O)—, —C(O)NR$^7$—, —SO$_2$NR$^8$—, —NR$^9$SO$_2$— or —13 NR$^{10}$— (wherein R$^6$, R$^7$, R$^8$, R$^9$ and R$^{10}$ each independently represents hydrogen, $C_{1-3}$alkyl or $C_{1-3}$alkoxy$C_{2-3}$alkyl), and R$^5$ is selected from one of the following twenty-two groups:

1) hydrogen, oxiranyl$C_{1-4}$alkyl or $C_{1-5}$alkyl which may be unsubstituted or which may be substituted with one or more groups selected from hydroxy, fluoro, chloro, bromo and amino;

2) $C_{1-5}$alkylX$^2$C(O)R$^{11}$ (wherein X$^2$ represents —O— or —NR$^{12}$— (in which R$^{12}$ represents hydrogen, $C_{1-3}$alkyl or $C_{1-3}$alkoxy$C_{2-3}$alkyl) and R$^{11}$ $C_{1-3}$alkyl, —NR$^{13}$R$^{14}$ or —OR$^{15}$ (wherein R$^{13}$, R$^{14}$ and R$^{15}$ which may be the same or different each represents hydrogen, C$_{1-5}$alkyl or C$_{1-3}$alkoxyC$_{2-3}$alkyl));

3) C$_{1-5}$alkylX$^3$R$^{16}$ (wherein X$^3$ represents —O—, —S—, —SO—, —SO$_2$—, —OC(O)—, —NR$^{17}$C(O)—, —C(O)NR$^{18}$, —SO$_2$NR$^{19}$—, —NR$^{20}$SO$_2$— or —NR$^{21}$— (wherein R$^{17}$, R$^{18}$, R$^{19}$, R$^{20}$ and R$^{21}$ each independently represents hydrogen, C$_{1-3}$alkyl or C$_{1-3}$alkoxyC$_{2-3}$alkyl) and R$^{16}$ represents hydrogen, C$_{1-3}$alkyl, cyclopentyl, cyclohexyl or a 4-, 5- or 6-membered saturated heterocyclic group with 1–2 heteroatoms, selected independently from O, S and N, which C$_{1-3}$alkyl group may bear 1 or 2 substituents selected from oxo, hydroxy, halogeno and C$_{1-4}$alkoxy and which cyclic group may bear 1 or 2 substituents selected from oxo, hydroxy, halogeno, cyano, C$_{1-4}$cyanoalkyl, C$_{1-4}$alkyl, C$_{1-4}$hydroxyalkyl, C$_{1-4}$alkoxy, C$_{1-4}$alkoxyC$_{1-4}$alkyl, C$_{1-4}$alkylsulphonylC$_{1-4}$alkyl, C$_{1-4}$alkoxycarbonyl, C$_{1-4}$aminoalkyl, C$_{1-4}$alkylamino, di(C$_{1-4}$alkyl)amino, C$_{1-4}$alkylaminoC$_{1-4}$alkyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy and a group —(—O—)$_f$(C$_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from C$_{1-4}$alkyl));

4) C$_{1-5}$alkylX$^4$C$_{1-5}$alkylX$^5$R$^{22}$ (wherein X$^4$ and X$^5$ which may be the same or different are each —O—, —S—, —SO—, —SO$_2$—, —NR$^{23}$C(O)—, —C(O)NR$^{24}$—, —SO$_2$NR$^{25}$—, —NR$^{26}$SO$_2$ or —NR$^{27}$— (wherein R$^{23}$, R$^{24}$, R$^{25}$, R$^{26}$ and R$^{27}$ each independently represents hydrogen, C$_{1-3}$alkyl or C$_{1-3}$alkoxyC$_{2-3}$alkyl) and R$^2$ represents hydrogen, C$_{1-3}$alkyl or C$_{1-3}$alkoxyC$_{2-3}$alkyl);

5) R$^{28}$ (wherein R$^{28}$ is a 4-, 5- or 6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, cyano, C$_{1-4}$cyanoalkyl, C$_{1-4}$alkyl, C$_{1-4}$hydroxyalkyl, C$_{1-4}$alkoxy, C$_1$alkanoyl, C$_{1-4}$alkoxyC$_{1-4}$alkyl, C$_{1-4}$alkylsulphonyl, C$_{1-4}$alkylsulphonylC$_{1-4}$alkyl, C$_{1-4}$alkoxycarbonyl, C$_{1-4}$aminoalkyl, C$_{1-4}$alkylamino, di(C$_{1-4}$alkyl)amino, C$_{1-4}$alkylaminoC$_{1-4}$alkyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy and a group —(—O—)$_f$(C$_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from C$_{1-4}$alkyl));

6) C$_{1-5}$alkylR$^{28}$ (wherein R$^{28}$ is as defined herein);
7) C$_{2-5}$alkenylR$^{28}$ (wherein R$^{28}$ is as defined herein);
8) C$_{2-5}$alkynylR$^{28}$ (wherein R$^{28}$ is as defined herein);
9) R$^{29}$ (wherein R$^{29}$ represents a pyridone group, a phenyl group or a 5–6-membered aromatic heterocyclic group (linked via carbon or nitrogen) with 1–3 heteroatoms selected from O, N and S, which pyridone, phenyl or aromatic heterocyclic group may carry up to 5 substituents selected from hydroxy, halogeno, amino, C$_{1-4}$alkyl, C$_{1-4}$alkoxy, C$_{1-4}$hydroxyalkyl, C$_{1-4}$aminoalkyl, C$_{1-4}$alkylamino, C$_{1-4}$hydroxyalkoxy, carboxy, trifluoromethyl, cyano, —C(O)NR$^{30}$R$^{31}$, —NR$^{32}$C(O)R$^{33}$ (wherein R$^{30}$, R$^{31}$, R$^{32}$ and R$^{33}$, which may be the same or different, each represents hydrogen, C$_{1-4}$alkyl or C$_{1-3}$alkoxyC$_{2-3}$alkyl) and a group —(—O—)$_f$(C$_{1-4}$alkyl)$_g$ringD (wherein f is 0 or 1, is 0 or 1 and ring D is a 4-, 5- or 6-membered saturated heterocyclic group with 1–2 heteroatoms, selected independently from O, S and N, which cyclic group may bear one or more substituents selected from C$_{1-4}$alkyl));

10) C$_{1-5}$alkylR$^{29}$ (wherein R$^{29}$ is as defined herein);
11) C$_{2-5}$alkenylR$^{29}$ (wherein R$^{29}$ is as defined herein);
12) C$_{2-5}$alkynylR$^{29}$ (wherein R$^{29}$ is as defined herein);
13) C$_{1-5}$alkylX$^6$R$^{29}$ (wherein X$^6$ represents —O—, —S—, —SO—, —SO$_2$—, —NR$^{34}$C(O)—, —C(O)NR$^{35}$—, —SO$_2$NR$^{36}$—, —NR$^{37}$SO$_2$— or —NR$^{38}$— (wherein R$^{34}$, R$^{35}$, R$^{36}$, R$^{37}$ and R$^{38}$ each independently represents hydrogen, C$_{1-3}$alkyl or C$_{1-3}$alkoxyC$_{2-3}$alkyl) and R$^{29}$ is as defined herein);
14) C$_{2-5}$alkenylX$^7$R$^{29}$ (wherein X$^7$ represents —O—, —S—, —SO—, —SO$_2$—, —NR$^{39}$C(O)—, —C(O)NR$^{40}$—, —SO$_2$NR$^{41}$—, —NR$^{42}$SO$_2$— or —NR$^{43}$— (wherein R$^{39}$, R$^{40}$, R$^{41}$, R$^{42}$ and R$^{43}$ each independently represents hydrogen, C$_{1-3}$alkyl or C$_{1-3}$alkoxyC$_{2-3}$alkyl) and R$^{29}$ is as defined herein);
15) C$_{2-5}$alkynylX$^8$R$^{29}$ (wherein X$^8$ represents —O—, —S—, —SO—, —SO$_2$—, —NR$^{44}$C(O)—, —C(O)NR$^{45}$—, —SO$_2$NR$^{46}$—, —NR$^{47}$SO$_2$— or —NR$^{48}$— (wherein R$^{44}$, R$^{45}$, R$^{46}$, R$^{47}$ and R$^{48}$ each independently represents hydrogen, C$_{1-3}$alkyl or C$_{1-3}$alkoxyC$_{2-3}$alkyl) and R$^{29}$ is as defined herein);
16) C$_{1-4}$alkylX$^9$C$_{1-4}$alkylX$^{29}$ (wherein X$^9$ represents —O—, —S—, —SO—, —SO$_2$—, —NR$^{49}$C(O)—, —C(O)NR$^{50}$—, —SO$_2$NR$^{51}$, —NR$^{52}$SO$_2$— or —NR$^{53}$— (wherein R$^{49}$, R$^{50}$, R$^{51}$, R$^{52}$ and R$^{53}$ each independently represents hydrogen, C$_{1-3}$alkyl or C$_{1-3}$alkoxyC$_{2-3}$alkyl) and R$^{29}$ is as defined herein);
17) C$_{1-4}$alkylX$^9$C$_{1-4}$alkylR$^{28}$ (wherein X$^9$ and R$^{28}$ are as defined herein);
18) C$_{2-5}$alkenyl which may be unsubstituted or which may be substituted with one or more groups selected from hydroxy, fluoro, amino, C$_{1-4}$alkylamino, N,N-di(C$_{1-4}$alkyl)amino, aminosulphonyl, N-C$_{1-4}$alkylaminosulphonyl and N,N-di(C$_{1-4}$alkyl)aminosulphonyl;
19) C$_{2-5}$alkynyl which may be unsubstituted or which may be substituted with one or more groups selected from hydroxy, fluoro, amino, C$_{1-4}$alkylamino, N,N-di(C$_{1-4}$alkyl)amino, aminosulphonyl, N-C$_{1-4}$alkylaminosulphonyl and N,N-di(C$_{1-4}$alkyl)aminosulphonyl;
20) C$_{2-5}$alkenylX$^9$C$_{1-4}$alkylR$^{28}$ (wherein X$^9$ and R$^{28}$ are as defined herein);
21) C$_{2-5}$alkynylX$^9$C$_{1-4}$alkylR$^{28}$ (wherein X$^9$ and R$^{28}$ are as defined herein); and
22) C$_{1-4}$alkylR$^{54}$(C$_{1-4}$alkyl)$_q$(X$^9$)$_r$R$^{55}$ (wherein X$^9$ is as defined herein, q is 0 or 1, r is 0 or 1, and R$^{54}$ and R$^{55}$ are each independently selected from hydrogen, C$_{1-3}$alkyl, cyclopentyl, cyclohexyl and a 4-, 5- or 6-membered saturated heterocyclic group with 1–2 heteroatoms, selected independently from O, S and N, which C$_{1-3}$alkyl group may bear 1 or 2 substituents selected from oxo, hydroxy, halogeno and C$_{1-4}$alkoxy and which cyclic group may bear 1 or 2 substituents selected from oxo, hydroxy, halogeno, cyano, C$_{1-4}$cyanoalkyl, C$_{1-4}$alkyl, C$_{1-4}$hydroxyalkyl, C$_{1-4}$alkoxy, C$_{1-4}$alkoxyC$_{1-4}$alkyl, C$_{1-4}$alkylsulphonylC$_{1-4}$alkyl, C$_{1-4}$alkoxycarbonyl, C$_{1-4}$aminoalkyl, C$_{1-4}$alkylamino, di(C$_{1-4}$alkyl)

amino, $C_{1-4}$alkylamino$C_{1-4}$alkyl, di($C_{1-4}$alkyl)amino$C_4$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from $C_{1-4}$alkyl), with the proviso that $R^{54}$ cannot be hydrogen);

and additionally wherein any $C_{1-5}$alkyl, $C_{2-5}$alkenyl or $C_{2-5}$alkynyl group in $R^5X^1$— may bear one or more substituents selected from hydroxy, halogeno and amino);

or a salt thereof.

2. A compound according to claim 1 wherein Z is —O— or —NH—.

3. A compound according to claim 1 wherein $G_1$, $G_2$, $G_3$, $G_4$ and $G_5$ are all —CH— which may be substituted as defined in claim 1.

4. A compound according to claim 3 wherein the optionally substituted indole moiety of formula $II^1$:

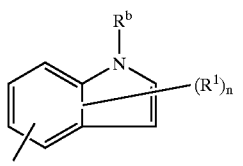

(II$^1$)

wherein $R^1$, $R^b$ and n are as defined in claim 1, is selected from 4-fluoro-2-methylindol-5-yl, 2-methylindol-5-yl, 2-methylindol-6-yl, 2,3-dimethylindol-5-yl, 1-methylindol-5-yl, 1,2-dimethylindol-5-yl, 4-fluoroindol-5-yl, 6-fluoroindol-5-yl and indol-5-yl.

5. A compound according to claim 1 wherein $R^b$ is hydrogen.

6. A compound according to claim 1 wherein $R^1$ represents methyl, ethyl, trifluoromethyl or halogeno.

7. A compound according to claim 1 wherein
$R^2$ represents hydroxy, halogeno, nitro, trifluoromethyl, $C_{1-3}$alkyl, cyano, amino or $R^5X^1$— [wherein $X^1$ is as defined in claim 1 and $R^5$ is selected from one of the following twenty groups:

1) $C_{1-3}$alkyl which may be unsubstituted or which may be substituted with one or more groups selected from fluoro, chloro and bromo, or $C_{2-3}$alkyl which may be unsubstituted or substituted with one or more groups selected from hydroxy and amino;

2) 2-(3,3-dimethylureido)ethyl, 3-(3,3-dimethylureido) propyl, 2-(3-methylureido)ethyl, 3-(3-methylureido) propyl, 2-ureidoethyl, 3-ureidopropyl, 2-(N,N-dimethylcarbamoyloxy)ethyl, 3-N,N-dimethylcarbamoyloxy)propyl, 2-(N-methylcarbamoyloxy)ethyl, 3-(N-methylcarbamoyloxy)propyl, 2-(carbamoyloxy)ethyl, 3-(carbamoyloxy)propyl, or 2-(N-methyl-N-(butoxycarbonyl)amino)ethyl;

3) $C_{2-3}$alkyl$X^3R^{16}$ (wherein $X^3$ is as defined in claim 1 and $R^{16}$ is a group selected from $C_{1-3}$alkyl, cyclopentyl, cyclohexyl, pyrrolidinyl, piperidinyl, piperazinyl, azetidinyl, imidazolidinyl and tetrahydropyranyl which group is linked to $X^3$ through a carbon atom and which $C_{1-3}$alkyl group may bear 1 or 2 substituents selected from hydroxy, halogeno and $C_{1-2}$alkoxy and which cyclopentyl, cyclohexyl, pyrrolidinyl, piperidinyl, piperazinyl, azetidinyl, imidazolidinyl or tetrahydropyranyl group may bear one substituent selected from oxo, hydroxy, halogeno, cyano, $C_{1-2}$cyanoalkyl, $C_{1-2}$alkyl, $C_{1-2}$hydroxyalkyl, $C_{1-2}$alkoxy, $C_{1-2}$alkoxy$C_{1-3}$alkyl, $C_{1-2}$alkylsulphonyl$C_{1-3}$alkyl, $C_{1-2}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino $C_{1-3}$alkyl, $C_{1-3}$alkylamino$C_{1-3}$alkoxy, di($C_{1-3}$alkyl) amino$C_{1-3}$alkoxy and a group —(—O—)$_f$($C_{1-3}$ alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino));

4) $C_{2-3}$alkyl$X^4C_{2-3}$alkyl$X^5R^{22}$ (wherein $X^4$ and $X^5$ are as defined in claim 1 and $R^{22}$ represents hydrogen or $C_{1-2}$alkyl);

5) $R^{28}$ (wherein $R^{28}$ is as defined in claim 1);

6) $C_{1-3}$alkyl$R^{59}$ (wherein $R^{59}$ is a group selected from pyrrolidinyl, piperazinyl, piperidinyl, azetidinyl, imidazolidinyl, 1,3-dioxolan-2-yl, 1,3-dioxan-2-yl, 1,3-dithiolan-2-yl and 1,3-dithian-2-yl, which group is linked to $C_{1-3}$alkyl through a carbon atom and which group may bear 1 or 2 substituents selected from oxo, hydroxy, halogeno, cyano, $C_{1-2}$cyanoalkyl, $C_{1-2}$alkyl, $C_{1-2}$hydroxyalkyl, $C_{1-2}$alkoxy, $C_{1-2}$alkanoyl, $C_{1-2}$alkoxy$C_{1-3}$alkyl, $C_{1-2}$alkylsulphonyl, $C_{1-2}$alkylsulphonyl$C_{1-3}$alkyl, $C_{1-2}$alkoxycarbonyl, $C_{1-3}$alkylamino, di($C_{1-3}$alkyl) amino, $C_{1-3}$alkylamino$C_{1-3}$alkyl, di($C_{1-3}$alkyl) amino$C_{1-3}$alkyl, $C_{1-3}$alkylamino$C_{1-3}$alkoxy, di($C_{1-3}$alkyl)amino$C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino)) or $C_{2-3}$alkyl$R^{60}$ (wherein $R^{60}$ is a group selected from morpholino, thiomorpholino, azetidin-1-yl, pyrrolidin-1-yl, piperazin-1-yl and piperidino which group may bear 1 or 2 substituents selected from oxo, hydroxy, halogeno, cyano, $C_{1-2}$cyanoalkyl, $C_{1-2}$alkyl, $C_{1-2}$hydroxyalkyl, $C_{1-2}$alkoxy, $C_{1-2}$alkanoyl, $C_{1-2}$alkoxy$C_{1-3}$alkyl, $C_{1-2}$alkylsulphonyl, $C_{1-2}$alkylsulphonyl$C_{1-3}$alkyl, $C_{1-2}$alkoxycarbonyl, $C_{1-3}$alkylamino, di($C_{1-3}$alkyl) amino, $C_{1-3}$alkylamino$C_{1-3}$alkyl, di($C_{1-3}$alkyl) amino$C_{1-3}$alkyl, $C_{1-3}$alkylamino$C_{1-3}$alkoxy, di($C_{1-3}$alkyl)amino$C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino));

7) $R^{29}$ (wherein $R^{29}$ is as defined in claim 1);

8) $C_{1-4}$alkyl$R^{29}$ (wherein $R^{29}$ is as defined in claim 1);

9) 1-$R^{29}$but-2-en-4-yl (wherein $R^{29}$ is as defined in claim 1);

10) 1-$R^{29}$but-2-yn-4-yl (wherein $R^{29}$ is as defined in claim 1);

11) $C_{1-3}$alkyl$X^6R^{29}$ (wherein $X^6$ and $R^{29}$ are as defined in claim 1);

12) 1-($R^{29}X^7$)but-2-en-4-yl (wherein $X^7$ and $R^{29}$ are as defined in claim 1);

13) 1-($R^{29}X^8$)but-2-yn-4-yl (wherein $X^8$ and $R^{29}$ are as defined in claim 1);

14) $C_{2-3}$alkyl$X^9C_{1-3}$alkyl$R^{29}$ (wherein $X^9$ and $R^{29}$ are as defined in claim 1);

15) $C_{2-3}$alkyl$X^9C_{1-3}$alkyl$R^{28}$ (wherein $X^9$ and $R^{29}$ are as defined in claim 1);

16) $C_{2-5}$alkenyl which may be unsubstituted or which may be substituted with one or more fluorine atoms or with one or two groups selected from hydroxy, fluoro, amino, $C_{1-4}$alkylamino, N,N-di($C_{1-4}$alkyl)amino, aminosulphonyl, N-$C_{1-4}$alkylaminosulphonyl and N,N-di($C_{1-4}$alkyl)aminosulphonyl;

17) $C_{2-5}$alkynyl which may be unsubstituted or which may be substituted with one or more fluorine atoms or with one or two groups selected from hydroxy, fluoro, amino, $C_{1-4}$alkylamino, N,N-di($C_{1-4}$alkyl)amino, aminosulphonyl, N-$C_{1-4}$alkylaminosulphonyl and N,N-di($C_{1-4}$alkyl)aminosulphonyl;

18) $C_{2-3}$alkenyl$X^9C_{1-3}$alkyl$R^{28}$ (wherein $X^9$ and $R^{28}$ are as defined in claim 1);

19) $C_{2-3}$alkynyl$X^9C_{1-3}$alkyl$R^{28}$ (wherein $X^9$ and $R^{28}$ are as defined in claim 1); and 20) $C_{1-3}$alkyl$R^{54}(C_{1-3}$alkyl$)_q(X^9)_rR^{55}$ (wherein $X^9$, q, r, $R^{54}$ and $R^{55}$ are as defined in claim 1);

and additionally wherein any $C_{1-5}$alkyl, $C_{2-5}$alkenyl or $C_{2-5}$alkynyl group in $R^5X^1$— may bear one or more substituents selected from hydroxy, halogeno and amino].

8. A compound according to claim 1 wherein one of the $R^2$ substituents is $R^5X^1$—, wherein $R^5$ and $X^1$ are as defined in claim 1, and the substituent $R^5X^1$—, is at the 7-position of the cinnoline ring.

9. A compound according to claim 7 wherein one of the $R^2$ substituents is $R^5X^1$—, wherein $R^5$ and $X^1$ are as defined in claim 7, and the substituent $R^5X^1$— is at the 7-position of the cinnoline ring.

10. A compound according to claim 8 wherein the $R^2$ substituent at the 6-position of the cinnoline ring is hydrogen, methoxy or cyano.

11. A compound selected from:

4-(4-fluoro-2-methylindol-5-yloxy)-6-methoxy-7-(3-(pyrrolidin-1-yl)propoxy)cinnoline, 4-(4-fluoro-2-methylindol-5-yloxy)-6-methoxy-7-(piperidin-4-ylmethoxy)cinnoline, 4-(4-fluoro-2-methylindol-5-yloxy)-7-(R)-(2-hydroxy-3-(piperidin-1-yl)propoxy)-6-methoxycinnoline, 4-(4-fluoro-2-methylindol-5-yloxy)-6-methoxy-7-(1-methylpiperidin-4-ylmethoxy)cinnoline, 7-benzyloxy-4-(4-fluoro-2-methylindol-5-yloxy)-6-methoxycinnoline, 4-(4-fluoro-2-methylindol-5-yloxy)-7-(R)-(2-hydroxy-3-(pyrrolidin-1-yl)propoxy)-6-methoxycinnoline, 4-(4-fluoro-2-methylindol-5-yl)oxy-6-methoxy-7-(3-(4-methylpiperazin-1-yl)propoxy)cinnoline, and 4-(4-fluoro-2-methylindol-5-yloxy)-6-methoxy-7-(3-(piperidin-1-yl)propoxy)cinnoline, or a salt thereof.

12. A compound according to any one of claims 1 to 11 in the form of a pharmaceutically acceptable salt.

13. A process for the preparation of a compound of formula I or salt thereof which comprises:

(a) the reaction of a compound of the formula III:

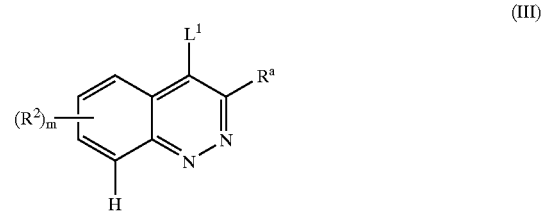

(III)

(wherein $R^a$, $R^2$ and m are as defined in claim 1 and $L^1$ is a displaceable moiety), with a compound of the formula IV:

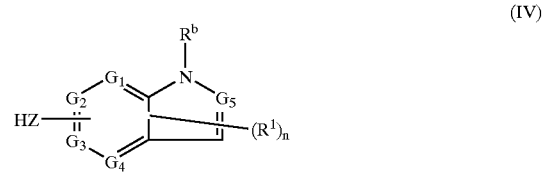

(IV)

(wherein $R^b$, $R^1$, $G_1$, $G_2$, $G_3$, $G_4$, $G_5$, Z and n are as defined in claim 1);

(b) a compound of formula I or a salt thereof wherein at least one $R^2$ is $R^5X^1$ wherein $R^5$ is as defined in claim 1 and $X^1$ is —O—, —S—, —OC(O)— or —NR$^{10}$— (wherein $R^{10}$ independently represents hydrogen, $C_{1-3}$alkyl or $C_{1-3}$alkoxy$C_{2-3}$alkyl) may be prepared by the reaction of a compound of the formula V:

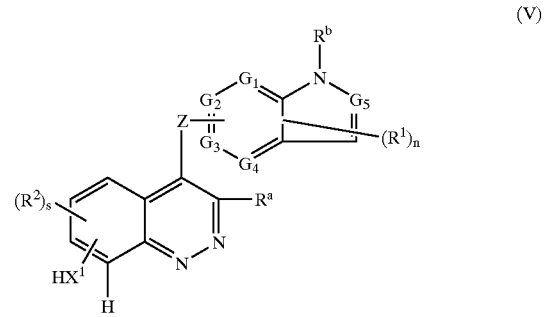

(V)

(wherein $R^a$, $R^b$, Z, $G_1$, $G_2$, $G_3$, $G_4$, $G_5$, $R^1$, $R^2$ and n are as defined in claim 1 and $X^1$ is as herein defined in this section and s is an integer from 0 to 2) with a compound of formula VI:

$R^5$-$L^1$ (I)

(wherein $R^5$ is as defined in claim 1 and $L^1$ is as defined herein);

(c) a compound of the formula I or a salt thereof wherein at least one $R^2$ is $R^5X^1$ wherein $R^5$ is as defined in claim 1 and $X^1$ is —O—, —S—, —OC(O)— or —NR$^{10}$— (wherein $R^{10}$ represents hydrogen, $C_{1-3}$alkyl or $C_{1-3}$alkoxy$C_{2-3}$alkyl) may be prepared by the reaction of a compound of the formula VII:

(VII)

with a compound of the formula VII:

$$R^5—X^1—H \quad (VIII)$$

(wherein $R^a$, $R^b$, $R^1$, $R^2$, $R^5$, $G_1$, $G_2$, $G_3$, $G_4$, $G_5$, Z and n are as defined in claim 1 and $L^1$ and s are as defined herein and $X^1$ is as defined herein in this section);

(d) a compound of the formula I or a salt thereof wherein at least one $R^2$ is $R^5X^1$ wherein $X^1$ is as defined in claim 1 and $R^5$ is $C_{1-5}$alkyl$R^{62}$, wherein $R^{62}$ is selected from one of the following nine groups:

1) $X^{10}C_{1-3}$alkyl (wherein $X^{10}$ represents —O—, —S—, —SO$_2$—, —NR$^{63}$C(O)— or —NR$^{64}$SO$_2$— (wherein $R^{63}$ and $R^{64}$ which may be the same or different are each hydrogen, $C_{1-3}$alkyl or $C_{1-3}$alkoxy$C_{2-3}$alkyl);

2) NR$^{65}$R$^{66}$ (wherein $R^{65}$ and $R^{66}$ which may be the same or different are each hydrogen, $C_{1-3}$alkyl or $C_{1-3}$alkoxy$C_{2-3}$alkyl);

3) $X^{11}C_{1-5}$alkyl$X^5R^{22}$ (wherein $X^{11}$ represents —O—, —S—, —SO$_2$—, —NR$^{67}$C(O)—, —NR$^{68}$SO$_2$— or —NR$^{69}$— (wherein $R^{67}$, $R^{68}$, and $R^{69}$ which may be the same or different are each hydrogen, $C_{1-3}$alkyl or $C_{1-3}$alkoxy$C_{2-3}$alkyl) and $X^5$ and $R^{22}$ are as defined in claim 1);

4) $R^{28}$ (wherein $R^{28}$ is as defined in claim 1);

5) $X^{12}R^{29}$ (wherein $X^{12}$ represents —O—, —S—, —SO$_2$—, —NR$^{70}$C(O)—, —NR$^{71}$SO$_2$—, or —NR$^{72}$— (wherein $R^{70}$, $R^{71}$, and $R^{72}$ which may be the same or different are each hydrogen, $C_{1-3}$alkyl or $C_{1-3}$alkoxy$C_{2-3}$alkyl) and $R^{29}$ is as defined in claim 1); and 6) $X^{13}C_{1-3}$alkyl$R^9$ (wherein $X^{13}$ represents —O—, —S—, —SO$_2$—, —NR$^{73}$C(O)—, —NR$^{74}$SO$_2$— or —NR$^{75}$— (wherein $R^{73}$, $R^{74}$ and $R^{75}$ each independently represents hydrogen, $C_{1-3}$alkyl or $C_{1-3}$alkoxy$C_{2-3}$alkyl) and $R^{29}$ is as defined in claim 1);

7) $R^{29}$ (wherein $R^{29}$ is as defined in claim 1);

8) $X^{13}C_{1-4}$alkyl$R^{28}$ (wherein $X^{13}$ and $R^{28}$ are as defined in claim 1); and 9) $R^{54}(C_{1-4}\text{alkyl})_q(X^9)_rR^{55}$ (wherein q, r, $X^9$, $R^{54}$ and $R^{55}$ are as defined in claim 1);

maybe prepared by reacting a compound of the formula IX:

(IX)

(wherein $X^1$, $R^a$, $R^b$, $R^1$, $R^2$, $G_1$, $G_2$, $G_3$, $G_4$, $G_5$, Z and n are as defined in claim 1 and $L^1$ and s are as defined herein) with a compound of the formula X:

$$R^{62}—H \quad (X)$$

(wherein $R^{62}$ is as defined herein) to give a compound of the formula I or salt thereof, (e) a compound of the formula I or a salt thereof wherein one or more of the substituents $(R^2)_m$ is represented by —NR$^{76}$R$^{77}$, where one (and the other is hydrogen) or both of $R^{76}$ and $R^{77}$ are $C_{1-3}$alkyl, may be effected by the reaction of a compound of formula I wherein the substituent $(R^2)_m$ is an amino group and an alkylating agent;

(f) a compound of the formula I or a salt thereof wherein $X^1$ is —SO— or —SO$_2$— may be prepared by oxidation from the corresponding compound in which $X^1$ is —S— or —SO— (when $X^1$ is —SO$_2$— is required in the final product);

and when a salt of a compound of formula I is required, reaction of the compound obtained with an acid or base whereby to obtain the desired salt.

14. A pharmaceutical composition which comprises a compound of the formula I as defined in any one of claims 1–11, or a pharmaceutically acceptable salt thereof, in association with a pharmaceutically acceptable excipient or carrier.

15. A method for producing an antiangiogenic and/or vascular permeability reducing effect in a warm-blooded animal in need thereof which comprises administering to said animal an effective amount of a compound of formula I as defined in any one of claims 1–11, or a pharmaceutically acceptable salt thereof.

* * * * *